United States Patent [19]
Goodman et al.

[11] Patent Number: 5,639,856
[45] Date of Patent: Jun. 17, 1997

[54] SEMAPHORIN GENE FAMILY

[75] Inventors: Corey S. Goodman; Alex L. Kolodkin; David Matthes; David R. Bentley; Timothy O'Connor, all of Berkeley, Calif.

[73] Assignee: The Regents of the University of California, Oakland, Calif.

[21] Appl. No.: 121,713

[22] Filed: Sep. 13, 1993

[51] Int. Cl.$^6$ .................... A61K 38/04; A61K 38/16; C07K 14/005; C07K 14/435

[52] U.S. Cl. ................ 530/326; 514/12; 514/14; 514/15; 514/16; 514/17; 514/21; 530/327; 530/328; 530/329; 530/330; 530/350

[58] Field of Search ................... 530/326, 327, 530/328, 329, 330, 350; 514/14, 15, 16, 17, 12, 21

[56] References Cited

U.S. PATENT DOCUMENTS

5,416,197  5/1995  Raper et al. .................. 530/387.9

OTHER PUBLICATIONS

Hames et al, Nucleic acid hybridisation, a practical approach, published 1985 by IRL Press (Oxford), pp. 81, 82, 93–95.

J. Gen. Virol., vol. 73, issued Nov. 1992, Aguado et al, "Nucleotide sequence of 21.8 kbp ... ", pp. 2887–2902.

J. Gen. Virol., vol. 72, issued 1991, Smith et al, "Nucleotide sequence of 42 kbp of vaccinia ... ", pp. 1349–1376.

Goodman and Shatz, "Developmental Mechanisms that Generate Precise Patterns of Neuronal Connectivity", Cell, vol. 72/Neuron, vol. 10 (Suppl.), 77–98 (1993).

Raper, "Repulsive Cues in Axonal Guidance", an abstract presented at the GIBCO–BRL Symposium on Genes and Development/Function of Brain on Jul. 26, 1993.

Kolodkin et al., "Fasciclin IV: Sequence, Expression, and Function during Growth Cone Guidance in the Grasshopper Embryo", Neuron, 9:831–845 (1992).

Luo et al., "Collapsin: A Protein in Brain that Induces the Collapse and Paralysis of Neuronal Growth Cones", Cell, 75:217–227 (1993).

Raper and Kapfhammer, "The Enrichment of a Neuronal Growth Cone Collapsing Activity from Embryonic Chick Brain", Neuron, 2:21–29 (1990).

Schnell and Schwab, "Axonal Regeneration in the Rat Spinal Cord Produced by an Antibody Against Myelin–associated Neurite Growth Inhibitors", Nature, 343:269–272 (1990).

Schwab and Caroni, "Oligodendrocytes and CNS Myelin are Nonpermissive Substrates for Neurite Growth and Fibroblast Spreading in vitro", J. Neuroscience, 8(7):2381–2393 (1988).

Kolodkin et al., Cell, vol. 75 (1993) 1389–1399.

Jessell et al., Principles of Neural Science (3rd edition)(1991) chapter 18.

Saneto et al., Neuro chemistry (Chap. 2) (1987) pp. 27–63.

Patel, Biochem. Soc. Trans. (1989) 17(5) 931.

McMartin, Biochem. Soc. Trans (1989) 17(5) pp. 931–934.

Bundgaard et al., Biochem. Soc. Trans., (1989) 17(5) pp. 947–949.

*Primary Examiner*—Jeffrey E. Russel
*Attorney, Agent, or Firm*—Richard Aron Osman

[57] ABSTRACT

A novel class of proteins, semaphorins, nucleic acids encoding semaphorins, semaphorin peptides, and methods of using semaphorins and semaphorin-encoding nucleic acids are disclosed. Semaphorin peptides and receptor agonists and antagonists provide potent modulators of nerve cell growth and regeneration. The invention provides pharmaceutical compositions, methods for screening chemical libraries for regulators of cell growth/differentiation; semaphorin gene-derived nucleic acids for use in genetic mapping, as probes for related genes, and as diagnostic reagents for genetic neurological disease; specific cellular and animal systems for the development of neurological disease therapy.

23 Claims, No Drawings

SEQUENCE LISTING ( 1 ) GENERAL INFORMATION:

( i i i ) NUMBER OF SEQUENCES: 100

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ01
            / note= "Xaa denotes D or E at residue #1; Q,K,R,A
            or N at residue #3; and Y,F or V at residue #5"

( x i ) SEQUENCE DESCRIPTION: SEQ ID NO:1:

Xaa  Cys  Xaa  Asn  Xaa  Ile
    1                          5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ02
            / note= "Xaa denotes Q,K,R,A or N at residue #2;
            Y,F or V at residue #4; and R,K,Q or T at residue
            # 6"

( x i ) SEQUENCE DESCRIPTION: SEQ ID NO:2:

Cys  Xaa  Asn  Xaa  Ile  Xaa
    1                          5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ03
            / note= "Xaa denotes N or G at residue #4; A,S or N
            at residue #5; Y,F,H or G at residue #6; and
            K,R,H,N or Q at residue #7"

( x i ) SEQUENCE DESCRIPTION: SEQ ID NO:3:

Cys  Gly  Thr  Xaa  Xaa  Xaa  Xaa
    1                          5

( 2 ) INFORMATION FOR SEQ ID NO:4:

( i ) SEQUENCE CHARACTERISTICS:
: ( A ) LENGTH: 8 amino acids
: ( B ) TYPE: amino acid
: ( C ) STRANDEDNESS: single
: ( D ) TOPOLOGY: linear ( i i ) MOLECULE TYPE: peptide ( i x ) FEATURE:
: ( A ) NAME/KEY: Peptide
: ( B ) LOCATION: 1..8
: ( D ) OTHER INFORMATION: /label=SEQ04
: / note= "Xaa denotes N or G at residue #4; and A,S or N at residue #5"

( x i ) SEQUENCE DESCRIPTION: SEQ ID NO:4:

```
Cys Gly Thr Xaa Xaa Xaa Xaa Pro
1               5
```

( 2 ) INFORMATION FOR SEQ ID NO:5:

( i ) SEQUENCE CHARACTERISTICS:
: ( A ) LENGTH: 10 amino acids
: ( B ) TYPE: amino acid
: ( C ) STRANDEDNESS: single
: ( D ) TOPOLOGY: linear ( i i ) MOLECULE TYPE: peptide ( i x ) FEATURE:
: ( A ) NAME/KEY: Peptide
: ( B ) LOCATION: 1..10
: ( D ) OTHER INFORMATION: /label=SEQ05
: / note= "Xaa denotes N or G at residue #4; and C or D at residue #10"

( x i ) SEQUENCE DESCRIPTION: SEQ ID NO:5:

```
Cys Gly Thr Xaa Xaa Xaa Xaa Pro Xaa Xaa
1               5                       10
```

( 2 ) INFORMATION FOR SEQ ID NO:6:

( i ) SEQUENCE CHARACTERISTICS:
: ( A ) LENGTH: 13 amino acids
: ( B ) TYPE: amino acid
: ( C ) STRANDEDNESS: single
: ( D ) TOPOLOGY: linear ( i i ) MOLECULE TYPE: peptide ( i x ) FEATURE:
: ( A ) NAME/KEY: Peptide
: ( B ) LOCATION: 1..13
: ( D ) OTHER INFORMATION: /label=SEQ06
: / note= "Xaa denotes C or D at residue #10; and Y or I at residue #13"

( x i ) SEQUENCE DESCRIPTION: SEQ ID NO:6:

```
Cys Gly Thr Xaa Xaa Xaa Xaa Pro Xaa Xaa Xaa Xaa Xaa
1               5                       10
```

( 2 ) INFORMATION FOR SEQ ID NO:7:

( i ) SEQUENCE CHARACTERISTICS:
: ( A ) LENGTH: 7 amino acids
: ( B ) TYPE: amino acid
: ( C ) STRANDEDNESS: single
: ( D ) TOPOLOGY: linear ( i i ) MOLECULE TYPE: peptide ( i x ) FEATURE:
: ( A ) NAME/KEY: Peptide (B) LOCATION: 1..7
(D) OTHER INFORMATION: /label=SEQ07
    / note= "Xaa denotes R,I,Q or V at residue #1; G or
    A at residue #2; L,V or K at residue #3; C or S at
    residue #4; F or Y at residue #6; and D or N at
    residue #7"

(xi) SEQUENCE DESCRIPTION: SEQ ID NO:7:

Xaa Xaa Xaa Xaa Pro Xaa Xaa
1                 5

(2) INFORMATION FOR SEQ ID NO:8:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=SEQ08
        / note= "Xaa denotes C or S at residue #1; F or Y
        at residue #3; D or N at residue #4; D,E,R or K at
        residue #6; and H,L or D at residue #7"

(xi) SEQUENCE DESCRIPTION: SEQ ID NO:8:

Xaa Pro Xaa Xaa Pro Xaa Xaa
1                 5

(2) INFORMATION FOR SEQ ID NO:9:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..9
    (D) OTHER INFORMATION: /label=SEQ09
        / note= "Xaa denotes G or A at residue #3; C or S
        at residue #5; and D or N at residue #8"

(xi) SEQUENCE DESCRIPTION: SEQ ID NO:9:

Gly Xaa Xaa Xaa Xaa Pro Tyr Xaa Pro
1                 5

(2) INFORMATION FOR SEQ ID NO:10:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=SEQ10
        / note= "Xaa denotes F or Y at residue #2; G or A
        at residue #4; and V,N or A at residue #6"

(xi) SEQUENCE DESCRIPTION: SEQ ID NO:10:

Leu Xaa Ser Xaa Thr Xaa Ala ( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=SEQ11
          / note= "Xaa denotes F or Y at residue #2; D or E
          at residue #8; and F or Y at residue #9"

( x i ) SEQUENCE DESCRIPTION: SEQ ID NO:11:

Leu Xaa Ser Xaa Thr Xaa Ala Xaa Xaa
1               5

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ12
          / note= "Xaa denotes F or Y at residue #1; G or A
          at residue #3; V,N or A at residue #5; D or E at
          residue #7; and F or Y at residue #8"

( x i ) SEQUENCE DESCRIPTION: SEQ ID NO:12:

Xaa Ser Xaa Thr Xaa Ala Xaa Xaa
1               5

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ13
          / note= "Xaa denotes N or D at residue #2; and A or
          K at residue #3"

( x i ) SEQUENCE DESCRIPTION: SEQ ID NO:13:

Leu Xaa Xaa Pro Asn Phe Val
1               5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Phe Phe Phe Arg Glu
1               5

( 2 ) INFORMATION FOR SEQ ID NO:15:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=SEQ15
        / note= "Xaa denotes F or Y at residue #3; and T or
        N at residue #6"

( x i ) SEQUENCE DESCRIPTION: SEQ ID NO:15:

Phe Phe Xaa Arg Glu Xaa
1               5

( 2 ) INFORMATION FOR SEQ ID NO:16:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=SEQ16
        / note= "Xaa denotes T or N at residue #5"

( x i ) SEQUENCE DESCRIPTION: SEQ ID NO:16:

Phe Phe Arg Glu Xaa Ala
1               5

( 2 ) INFORMATION FOR SEQ ID NO:17:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=SEQ17
        / note= "Xaa denotes F or Y at residue #2; and T or
        N at residue #5"

( x i ) SEQUENCE DESCRIPTION: SEQ ID NO:17:

Phe Xaa Arg Glu Xaa Ala
1               5

( 2 ) INFORMATION FOR SEQ ID NO:18:

( i ) SEQUENCE CHARACTERISTICS:

(A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION: 1..6
                (D) OTHER INFORMATION: /label=SEQ18
                        / note= "Xaa denotes F or Y at residue #4"

(xi) SEQUENCE DESCRIPTION: SEQ ID NO:18:

Tyr  Phe  Phe  Xaa  Arg  Glu
        1                   5

(2) INFORMATION FOR SEQ ID NO:19:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION: 1..6
                (D) OTHER INFORMATION: /label=SEQ19
                        / note= "Xaa denotes F or Y at residue #1; and F or
                        Y at residue #4"

(xi) SEQUENCE DESCRIPTION: SEQ ID NO:19:

Xaa  Phe  Phe  Xaa  Arg  Glu
        1                   5

(2) INFORMATION FOR SEQ ID NO:20:

(i) SEQUENCE CHARACTERISTICS:
                (A) LENGTH: 7 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION: 1..7
                (D) OTHER INFORMATION: /label=SEQ20
                        / note= "Xaa denotes F or Y at residue #1; F or Y
                        at residue #2; F or Y at residue #3; and T or N at
                        residue #6"

(xi) SEQUENCE DESCRIPTION: SEQ ID NO:20:

Xaa  Xaa  Xaa  Arg  Glu  Xaa  Ala
        1                   5

(2) INFORMATION FOR SEQ ID NO:21:

(i) SEQUENCE CHARACTERISTICS:
                (A) LENGTH: 7 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION: 1..7
                (D) OTHER INFORMATION: /label=SEQ21

/ note= "Xaa denotes I or V at residue #1; F or Y
at residue #2; F or Y at residue #4; and F or Y at
residue #5"

( x i ) SEQUENCE DESCRIPTION: SEQ ID NO:21:

Xaa Xaa Phe Xaa Xaa Arg Glu
1               5

( 2 ) INFORMATION FOR SEQ ID NO:22:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..7
( D ) OTHER INFORMATION: /label=SEQ22
/ note= "Xaa denotes K,F or Y at residue #2; F or Y
at residue #4; F,Y,I or L at residue #5; F,Y,I or
L at residue #6; and F or Y at residue #7"

( x i ) SEQUENCE DESCRIPTION: SEQ ID NO:22:

Asp Xaa Val Xaa Xaa Xaa Xaa
1               5

( 2 ) INFORMATION FOR SEQ ID NO:23:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..8
( D ) OTHER INFORMATION: /label=SEQ23
/ note= "Xaa denotes V or I at residue #1; F or Y
at residue #2; F,Y,I or L at residue #3; F,Y,I or
L at residue #4; R or T at residue #6; and T or N
at residue #8"

( x i ) SEQUENCE DESCRIPTION: SEQ ID NO:23:

Xaa Xaa Xaa Xaa Phe Xaa Xaa Xaa
1               5

( 2 ) INFORMATION FOR SEQ ID NO:24:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..8
( D ) OTHER INFORMATION: /label=SEQ24
/ note= "Xaa denotes V or I at residue #1; F or Y
at residue #2; F,Y,I or L at residue #3; F,Y,I or
L at residue #4; F or Y at residue #5; R or T at
residue #6; E,D or V at residue #7; and T or N at
residue #8"

( x i ) SEQUENCE DESCRIPTION: SEQ ID NO:24:

```
    Xaa  Xaa  Xaa  Xaa  Xaa  Xaa  Xaa  Xaa
    1                 5
```

( 2 ) INFORMATION FOR SEQ ID NO:25:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..7
  ( D ) OTHER INFORMATION: /label=SEQ25
   / note= "Xaa denotes F or Y at residue #2; and C or
   S at residue #5"

( x i ) SEQUENCE DESCRIPTION: SEQ ID NO:25:

```
    Glu  Xaa  Ile  Asn  Xaa  Gly  Lys
    1                 5
```

( 2 ) INFORMATION FOR SEQ ID NO:26:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..7
  ( D ) OTHER INFORMATION: /label=SEQ26
   / note= "Xaa denotes F or Y at residue #1; and A,V
   or I at residue #7"

( x i ) SEQUENCE DESCRIPTION: SEQ ID NO:26:

```
    Xaa  Ile  Asn  Cys  Gly  Lys  Xaa
    1                 5
```

( 2 ) INFORMATION FOR SEQ ID NO:27:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..7
  ( D ) OTHER INFORMATION: /label=SEQ27
   / note= "Xaa denotes V or I at residue #2; A or G
   at residue #3; R or Q at residue #4; and V or I at
   residue #5"

( x i ) SEQUENCE DESCRIPTION: SEQ ID NO:27:

```
    Arg  Xaa  Xaa  Xaa  Xaa  Cys  Lys
    1                 5
```

( 2 ) INFORMATION FOR SEQ ID NO:28:

( i ) SEQUENCE CHARACTERISTICS:
  ( A ) LENGTH: 9 amino acids
  ( B ) TYPE: amino acid (C) STRANDEDNESS: single
(D) TOPOLOGY: linear (i i) MOLECULE TYPE: peptide (i x) FEATURE:
    (A) NAME/KEY: Peptide
    (B) LOCATION: 1..9
    (D) OTHER INFORMATION: /label=SEQ28
        / note= "Xaa denotes V or I at residue #2; R or Q
        at residue #4; and V or I at residue #5"

(x i) SEQUENCE DESCRIPTION: SEQ ID NO:28:

Arg Xaa Xaa Xaa Xaa Cys Xaa Xaa Asp
1                  5

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..13
        (D) OTHER INFORMATION: /label=SEQ29
            / note= "Xaa denotes V,A or I at residue #3; and
            V,A or I at residue #8"

(x i) SEQUENCE DESCRIPTION: SEQ ID NO:29:

Gly Lys Xaa Xaa Xaa Xaa Arg Xaa Xaa Xaa Xaa Cys Lys
1                  5                                  10

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..7
        (D) OTHER INFORMATION: /label=SEQ30
            / note= "Xaa denotes R,K or N at residue #1; T,A or
            S at residue #3; T,A or S at residue #4; F,Y or L
            at residue #5; and K or R at residue #7"

(x i) SEQUENCE DESCRIPTION: SEQ ID NO:30:

Xaa Trp Xaa Xaa Xaa Leu Xaa
1                  5

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..8
        (D) OTHER INFORMATION: /label=SEQ31
            / note= "Xaa denotes F or Y at residue #1; K or R at residue #3; A or S at residue #4; and N or I at
residue #7"

( x i ) SEQUENCE DESCRIPTION: SEQ ID NO:31:

Xaa Leu Xaa Xaa Arg Leu Xaa Cys
1               5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ32
            / note= "Xaa denotes N or I at residue #1; I or V
            at residue #4; and P or S at residue #5"

( x i ) SEQUENCE DESCRIPTION: SEQ ID NO:32:

Xaa Cys Ser Xaa Xaa Gly
1               5

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=SEQ33
            / note= "Xaa denotes T,A or S at residue #2; T,A or
            S at residue #3; F,Y or L at residue #4; and
            A,S,V,I or L at residue #7"

( x i ) SEQUENCE DESCRIPTION: SEQ ID NO:33:

Trp Xaa Xaa Xaa Leu Lys Xaa Xaa Leu
1               5

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /label=SEQ34
            / note= "Xaa denotes T,A or S at residue #2; and
            T,A or S at residue #3"

( x i ) SEQUENCE DESCRIPTION: SEQ ID NO:34:

Trp Xaa Xaa Xaa Leu Lys Xaa Xaa Leu Xaa Cys
1               5                       10

( 2 ) INFORMATION FOR SEQ ID NO:35:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..11
    ( D ) OTHER INFORMATION: /label=SEQ35
        / note= "Xaa denotes T or S at residue #3"

( x i ) SEQUENCE DESCRIPTION: SEQ ID NO:35:

Trp Xaa Xaa Xaa Leu Lys Xaa Xaa Leu Xaa Cys
1               5                       10

( 2 ) INFORMATION FOR SEQ ID NO:36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ36
            / note= "Xaa denotes F or Y at residue #1; F or Y
            at residue #2; and N or D at residue #3"

( x i ) SEQUENCE DESCRIPTION: SEQ ID NO:36:

Xaa Xaa Xaa Glu Ile Gln Ser
1               5

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ37
            / note= "Xaa denotes F or Y at residue #1; F or Y
            at residue #3; F or Y at residue #4; F or Y at
            residue #5; and N or D at residue #6"

( x i ) SEQUENCE DESCRIPTION: SEQ ID NO:37:

Xaa Pro Xaa Xaa Xaa Xaa Glu
1               5

( 2 ) INFORMATION FOR SEQ ID NO:38:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide (B) LOCATION: 1..7
(D) OTHER INFORMATION: /label=SEQ38
/ note= "Xaa denotes V,I or L at residue #4; and F or Y at residue #7"

(xi) SEQUENCE DESCRIPTION: SEQ ID NO:38:

Gly Ser Ala Xaa Cys Xaa Xaa
1               5

(2) INFORMATION FOR SEQ ID NO:39:

(i) SEQUENCE CHARACTERISTICS:
  (A) LENGTH: 8 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..8
  (D) OTHER INFORMATION: /label=SEQ39
    / note= "Xaa denotes V,I or L at residue #3; and F or Y at residue #6"

(xi) SEQUENCE DESCRIPTION: SEQ ID NO:39:

Ser Ala Xaa Cys Xaa Xaa Xaa Met
1               5

(2) INFORMATION FOR SEQ ID NO:40:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..7
  (D) OTHER INFORMATION: /label=SEQ40
    / note= "Xaa denotes N or A at residue #3; and P or A at residue #6"

(xi) SEQUENCE DESCRIPTION: SEQ ID NO:40:

Asn Ser Xaa Trp Leu Xaa Val
1               5

(2) INFORMATION FOR SEQ ID NO:41:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..7
  (D) OTHER INFORMATION: /label=SEQ41
    / note= "Xaa denotes V,L or I at residue #1; and E,D,Y,S or F at residue #3"

(xi) SEQUENCE DESCRIPTION: SEQ ID NO:41:

Xaa Pro Xaa Pro Arg Pro Gly
1               5

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=SEQ42
            / note= "Xaa denotes V,L or I at residue #1; and R
            or A at residue #5"

( x i ) SEQUENCE DESCRIPTION: SEQ ID NO:42:

Xaa Pro Xaa Pro Xaa Pro Gly Xaa Cys
1               5

( 2 ) INFORMATION FOR SEQ ID NO:43:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ43
            / note= "Xaa denotes E,D,Y,S or F at residue #2;
            and T,Q or S at residue #7"

( x i ) SEQUENCE DESCRIPTION: SEQ ID NO:43:

Pro Xaa Pro Arg Pro Gly Xaa Cys
1               5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ44
            / note= "Xaa denotes H,F or Y at residue #3; and A
            or G at residue #5"

( x i ) SEQUENCE DESCRIPTION: SEQ ID NO:44:

Asp Pro Xaa Cys Xaa Trp
1               5

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

(A) NAME/KEY: Peptide
(B) LOCATION: 1..6
(D) OTHER INFORMATION: /label=SEQ45
/ note= "Xaa denotes H,F or Y at residue #2; and A
or G at residue #4"

(xi) SEQUENCE DESCRIPTION: SEQ ID NO:45:

Pro Xaa Cys Xaa Trp Asp
1               5

(2) INFORMATION FOR SEQ ID NO:46:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..7
(D) OTHER INFORMATION: /label=SEQ46
/ note= "Xaa denotes A or G at residue #5"

(xi) SEQUENCE DESCRIPTION: SEQ ID NO:46:

Asp Pro Xaa Cys Xaa Trp Asp
1               5

(2) INFORMATION FOR SEQ ID NO:47:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:47:

Cys Xaa Xaa Xaa Xaa Asp Pro Xaa Cys Xaa Trp Asp
1               5                   10

(2) INFORMATION FOR SEQ ID NO:48:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:48:

Cys Xaa Xaa Xaa Asp Pro Xaa Cys Xaa Trp Asp
1               5                   10

(2) INFORMATION FOR SEQ ID NO:49:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:49:

Cys Xaa Xaa Asp Pro Xaa Cys Xaa Trp Asp
1               5                   10

(2) INFORMATION FOR SEQ ID NO:50:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Cys Xaa Xaa Cys Xaa Xaa Xaa Xaa Asp Xaa Xaa Cys Xaa Trp Asp
 1               5                  10                  15
```

(2) INFORMATION FOR SEQ ID NO:51:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Cys Xaa Xaa Cys Xaa Xaa Xaa Asp Xaa Xaa Cys Xaa Trp Asp
 1               5                  10
```

(2) INFORMATION FOR SEQ ID NO:52:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Cys Xaa Xaa Cys Xaa Xaa Asp Xaa Xaa Cys Xaa Trp Asp
 1               5                  10
```

(2) INFORMATION FOR SEQ ID NO:53:

(i) SEQUENCE CHARACTERISTICS:
        (A) LENGTH: 2601 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..2331

(xi) SEQUENCE DESCRIPTION: SEQ ID NO:53:

```
GGAATTCCCT GCAGC ATG GGC TGG TTA ACT AGG ATT GTC TGT CTT TTC TGG        51
                 Met Gly Trp Leu Thr Arg Ile Val Cys Leu Phe Trp
                  1               5                  10

GGA GTA TTA CTT ACA GCA AGA GCA AAC TAT CAG AAT GGG AAG AAC AAT         99
Gly Val Leu Leu Thr Ala Arg Ala Asn Tyr Gln Asn Gly Lys Asn Asn
            15                  20                  25

GTG CCA AGG CTG AAA TTA TCC TAC AAA GAA ATG TTG GAA TCC AAC AAT        147
Val Pro Arg Leu Lys Leu Ser Tyr Lys Glu Met Leu Glu Ser Asn Asn
        30                  35                  40

GTG ATC ACT TTC AAT GGC TTG GCC AAC AGC TCC AGT TAT CAT ACC TTC        195
```

| | | | | | | | | | | | | | | | | |
|---|---|---|---|---|---|---|---|---|---|---|---|---|---|---|---|---|
| Val | Ile | Thr | Phe | Asn | Gly | Leu | Ala | Asn | Ser | Ser | Ser | Tyr | His | Thr | Phe | |
| 45 | | | | | 50 | | | | 55 | | | | | | 60 | |
| CTT | TTG | GAT | GAG | GAA | CGG | AGT | AGG | CTG | TAT | GTT | GGA | GCA | AAG | GAT | CAC | 243 |
| Leu | Leu | Asp | Glu | Glu | Arg | Ser | Arg | Leu | Tyr | Val | Gly | Ala | Lys | Asp | His | |
| | | | | 65 | | | | | 70 | | | | | 75 | | |
| ATA | TTT | TCA | TTC | GAC | CTG | GTT | AAT | ATC | AAG | GAT | TTT | CAA | AAG | ATT | GTG | 291 |
| Ile | Phe | Ser | Phe | Asp | Leu | Val | Asn | Ile | Lys | Asp | Phe | Gln | Lys | Ile | Val | |
| | | | 80 | | | | | 85 | | | | | 90 | | | |
| TGG | CCA | GTA | TCT | TAC | ACC | AGA | AGA | GAT | GAA | TGC | AAG | TGG | GCT | GGA | AAA | 339 |
| Trp | Pro | Val | Ser | Tyr | Thr | Arg | Arg | Asp | Glu | Cys | Lys | Trp | Ala | Gly | Lys | |
| | | 95 | | | | | 100 | | | | | 105 | | | | |
| GAC | ATC | CTG | AAA | GAA | TGT | GCT | AAT | TTC | ATC | AAG | GTA | CTT | AAG | GCA | TAT | 387 |
| Asp | Ile | Leu | Lys | Glu | Cys | Ala | Asn | Phe | Ile | Lys | Val | Leu | Lys | Ala | Tyr | |
| | 110 | | | | | 115 | | | | | 120 | | | | | |
| AAT | CAG | ACT | CAC | TTG | TAC | GCC | TGT | GGA | ACG | GGG | GCT | TTT | CAT | CCA | ATT | 435 |
| Asn | Gln | Thr | His | Leu | Tyr | Ala | Cys | Gly | Thr | Gly | Ala | Phe | His | Pro | Ile | |
| 125 | | | | | 130 | | | | | 135 | | | | | 140 | |
| TGC | ACC | TAC | ATT | GAA | ATT | GGA | CAT | CAT | CCT | GAG | GAC | AAT | ATT | TTT | AAG | 483 |
| Cys | Thr | Tyr | Ile | Glu | Ile | Gly | His | His | Pro | Glu | Asp | Asn | Ile | Phe | Lys | |
| | | | | 145 | | | | | 150 | | | | | 155 | | |
| CTG | GAG | AAC | TCA | CAT | TTT | GAA | AAC | GGC | CGT | GGG | AAG | AGT | CCA | TAT | GAC | 531 |
| Leu | Glu | Asn | Ser | His | Phe | Glu | Asn | Gly | Arg | Gly | Lys | Ser | Pro | Tyr | Asp | |
| | | | 160 | | | | | 165 | | | | | 170 | | | |
| CCT | AAG | CTG | CTG | ACA | GCA | TCC | CTT | TTA | ATA | GAT | GGA | GAA | TTA | TAC | TCT | 579 |
| Pro | Lys | Leu | Leu | Thr | Ala | Ser | Leu | Leu | Ile | Asp | Gly | Glu | Leu | Tyr | Ser | |
| | | 175 | | | | | 180 | | | | | 185 | | | | |
| GGA | ACT | GCA | GCT | GAT | TTT | ATG | GGG | CGA | GAC | TTT | GCT | ATC | TTC | CGA | ACT | 627 |
| Gly | Thr | Ala | Ala | Asp | Phe | Met | Gly | Arg | Asp | Phe | Ala | Ile | Phe | Arg | Thr | |
| | 190 | | | | | 195 | | | | | 200 | | | | | |
| CTT | GGG | CAC | CAC | CAC | CCA | ATC | AGG | ACA | GAG | CAG | CAT | GAT | TCC | AGG | TGG | 675 |
| Leu | Gly | His | His | His | Pro | Ile | Arg | Thr | Glu | Gln | His | Asp | Ser | Arg | Trp | |
| 205 | | | | | 210 | | | | | 215 | | | | | 220 | |
| CTC | AAT | GAT | CCA | AAG | TTC | ATT | AGT | GCC | CAC | CTC | ATC | TCA | GAG | AGT | GAC | 723 |
| Leu | Asn | Asp | Pro | Lys | Phe | Ile | Ser | Ala | His | Leu | Ile | Ser | Glu | Ser | Asp | |
| | | | | 225 | | | | | 230 | | | | | 235 | | |
| AAT | CCT | GAA | GAT | GAC | AAA | GTA | TAC | TTT | TTC | TTC | CGT | GAA | AAT | GCA | ATA | 771 |
| Asn | Pro | Glu | Asp | Asp | Lys | Val | Tyr | Phe | Phe | Phe | Arg | Glu | Asn | Ala | Ile | |
| | | | 240 | | | | | 245 | | | | | 250 | | | |
| GAT | GGA | GAA | CAC | TCT | GGA | AAA | GCT | ACT | CAC | GCT | AGA | ATA | GGT | CAG | ATA | 819 |
| Asp | Gly | Glu | His | Ser | Gly | Lys | Ala | Thr | His | Ala | Arg | Ile | Gly | Gln | Ile | |
| | | 255 | | | | | 260 | | | | | 265 | | | | |
| TGC | AAG | AAT | GAC | TTT | GGA | GGG | CAC | AGA | AGT | CTG | GTG | AAT | AAA | TGG | ACA | 867 |
| Cys | Lys | Asn | Asp | Phe | Gly | Gly | His | Arg | Ser | Leu | Val | Asn | Lys | Trp | Thr | |
| | 270 | | | | | 275 | | | | | 280 | | | | | |
| ACA | TTC | CTC | AAA | GCT | CGT | CTG | ATT | TGC | TCA | GTG | CCA | GGT | CCA | AAT | GGC | 915 |
| Thr | Phe | Leu | Lys | Ala | Arg | Leu | Ile | Cys | Ser | Val | Pro | Gly | Pro | Asn | Gly | |
| 285 | | | | | 290 | | | | | 295 | | | | | 300 | |
| ATT | GAC | ACT | CAT | TTT | GAT | GAA | CTG | CAG | GAT | GTA | TTC | CTA | ATG | AAC | TTT | 963 |
| Ile | Asp | Thr | His | Phe | Asp | Glu | Leu | Gln | Asp | Val | Phe | Leu | Met | Asn | Phe | |
| | | | 305 | | | | | 310 | | | | | 315 | | | |
| AAA | GAT | CCT | AAA | AAT | CCA | GTT | GTA | TAT | GGA | GTG | TTT | ACG | ACT | TCC | AGT | 1011 |
| Lys | Asp | Pro | Lys | Asn | Pro | Val | Val | Tyr | Gly | Val | Phe | Thr | Thr | Ser | Ser | |
| | | | 320 | | | | | 325 | | | | | 330 | | | |
| AAC | ATT | TTC | AAG | GGA | TCA | GCC | GTG | TGT | ATG | TAT | AGC | ATG | AGT | GAT | GTG | 1059 |
| Asn | Ile | Phe | Lys | Gly | Ser | Ala | Val | Cys | Met | Tyr | Ser | Met | Ser | Asp | Val | |
| | | 335 | | | | | 340 | | | | | 345 | | | | |
| AGA | AGG | GTG | TTC | CTT | GGT | CCA | TAT | GCC | CAC | AGG | GAT | GGA | CCC | AAC | TAT | 1107 |
| Arg | Arg | Val | Phe | Leu | Gly | Pro | Tyr | Ala | His | Arg | Asp | Gly | Pro | Asn | Tyr | |
| | 350 | | | | | 355 | | | | | 360 | | | | | |
| CAA | TGG | GTG | CCT | TAT | CAA | GGA | AGA | GTC | CCC | TAT | CCA | CGG | CCA | GGA | ACT | 1155 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| Gln | Trp | Val | Pro | Tyr | Gln | Gly | Arg | Val | Pro | Tyr | Pro | Arg | Pro | Gly | Thr |      |
| 365 |     |     |     |     | 370 |     |     |     |     | 375 |     |     |     |     | 380 |      |
| TGT | CCC | AGC | AAA | ACA | TTT | GGT | GGT | TTT | GAC | TCT | ACA | AAG | GAC | CTT | CCT | 1203 |
| Cys | Pro | Ser | Lys | Thr | Phe | Gly | Gly | Phe | Asp | Ser | Thr | Lys | Asp | Leu | Pro |      |
|     |     |     |     | 385 |     |     |     |     | 390 |     |     |     |     | 395 |     |      |
| GAT | GAT | GTT | ATA | ACC | TTT | GCA | AGA | AGT | CAT | CCA | GCC | ATG | TAC | AAT | CCA | 1251 |
| Asp | Asp | Val | Ile | Thr | Phe | Ala | Arg | Ser | His | Pro | Ala | Met | Tyr | Asn | Pro |      |
|     |     |     | 400 |     |     |     |     | 405 |     |     |     |     | 410 |     |     |      |
| GTG | TTT | CCT | ATG | AAC | AAT | CGC | CCA | ATA | GTG | ATC | AAA | ACG | GAT | GTA | AAT | 1299 |
| Val | Phe | Pro | Met | Asn | Asn | Arg | Pro | Ile | Val | Ile | Lys | Thr | Asp | Val | Asn |      |
|     |     | 415 |     |     |     |     | 420 |     |     |     |     | 425 |     |     |     |      |
| TAT | CAA | TTT | ACA | CAA | ATT | GTC | GTA | GAC | CGA | GTG | GAT | GCA | GAA | GAT | GGA | 1347 |
| Tyr | Gln | Phe | Thr | Gln | Ile | Val | Val | Asp | Arg | Val | Asp | Ala | Glu | Asp | Gly |      |
|     | 430 |     |     |     |     | 435 |     |     |     |     | 440 |     |     |     |     |      |
| CAG | TAT | GAT | GTT | ATG | TTT | ATC | GGA | ACA | GAT | GTT | GGG | ACC | GTT | CTT | AAA | 1395 |
| Gln | Tyr | Asp | Val | Met | Phe | Ile | Gly | Thr | Asp | Val | Gly | Thr | Val | Leu | Lys |      |
| 445 |     |     |     |     | 450 |     |     |     |     | 455 |     |     |     |     | 460 |      |
| GTA | GTT | TCA | ATT | CCT | AAG | GAG | ACT | TGG | TAT | GAT | TTA | GAA | GAG | GTT | CTG | 1443 |
| Val | Val | Ser | Ile | Pro | Lys | Glu | Thr | Trp | Tyr | Asp | Leu | Glu | Glu | Val | Leu |      |
|     |     |     |     | 465 |     |     |     |     | 470 |     |     |     |     | 475 |     |      |
| CTG | GAA | GAA | ATG | ACA | GTT | TTT | CGG | GAA | CCG | ACT | GCT | ATT | TCA | GCA | ATG | 1491 |
| Leu | Glu | Glu | Met | Thr | Val | Phe | Arg | Glu | Pro | Thr | Ala | Ile | Ser | Ala | Met |      |
|     |     |     | 480 |     |     |     |     | 485 |     |     |     |     | 490 |     |     |      |
| GAG | CTT | TCC | ACT | AAG | CAG | CAA | CAA | CTA | TAT | ATT | GGT | TCA | ACG | GCT | GGG | 1539 |
| Glu | Leu | Ser | Thr | Lys | Gln | Gln | Gln | Leu | Tyr | Ile | Gly | Ser | Thr | Ala | Gly |      |
|     |     | 495 |     |     |     |     | 500 |     |     |     |     | 505 |     |     |     |      |
| GTT | GCC | CAG | CTC | CCT | TTA | CAC | CGG | TGT | GAT | ATT | TAC | GGG | AAA | GCG | TGT | 1587 |
| Val | Ala | Gln | Leu | Pro | Leu | His | Arg | Cys | Asp | Ile | Tyr | Gly | Lys | Ala | Cys |      |
|     | 510 |     |     |     |     | 515 |     |     |     |     | 520 |     |     |     |     |      |
| GCT | GAG | TGT | TGC | CTC | GCC | CGA | GAC | CCT | TAC | TGT | GCT | TGG | GAT | GGT | TCT | 1635 |
| Ala | Glu | Cys | Cys | Leu | Ala | Arg | Asp | Pro | Tyr | Cys | Ala | Trp | Asp | Gly | Ser |      |
| 525 |     |     |     |     | 530 |     |     |     |     | 535 |     |     |     |     | 540 |      |
| GCA | TGT | TCT | CGC | TAT | TTT | CCC | ACT | GCA | AAG | AGA | CGC | ACA | AGA | CGA | CAA | 1683 |
| Ala | Cys | Ser | Arg | Tyr | Phe | Pro | Thr | Ala | Lys | Arg | Arg | Thr | Arg | Arg | Gln |      |
|     |     |     |     | 545 |     |     |     |     | 550 |     |     |     |     | 555 |     |      |
| GAT | ATA | AGA | AAT | GGA | GAC | CCA | CTG | ACT | CAC | TGT | TCA | GAC | TTA | CAC | CAT | 1731 |
| Asp | Ile | Arg | Asn | Gly | Asp | Pro | Leu | Thr | His | Cys | Ser | Asp | Leu | His | His |      |
|     |     |     | 560 |     |     |     |     | 565 |     |     |     |     | 570 |     |     |      |
| GAT | AAT | CAC | CAT | GGC | CAC | AGC | CCT | GAA | GAG | AGA | ATC | ATC | TAT | GGT | GTA | 1779 |
| Asp | Asn | His | His | Gly | His | Ser | Pro | Glu | Glu | Arg | Ile | Ile | Tyr | Gly | Val |      |
|     |     | 575 |     |     |     |     | 580 |     |     |     |     | 585 |     |     |     |      |
| GAG | AAT | AGT | AGC | ACA | TTT | TTG | GAA | TGC | AGT | CCG | AAG | TCG | CAG | AGA | GCG | 1827 |
| Glu | Asn | Ser | Ser | Thr | Phe | Leu | Glu | Cys | Ser | Pro | Lys | Ser | Gln | Arg | Ala |      |
|     | 590 |     |     |     |     | 595 |     |     |     |     | 600 |     |     |     |     |      |
| CTG | GTC | TAT | TGG | CAA | TTC | CAG | AGG | CGA | AAT | GAA | GAG | CGA | AAA | GAA | GAG | 1875 |
| Leu | Val | Tyr | Trp | Gln | Phe | Gln | Arg | Arg | Asn | Glu | Glu | Arg | Lys | Glu | Glu |      |
| 605 |     |     |     |     | 610 |     |     |     |     | 615 |     |     |     |     | 620 |      |
| ATC | AGA | GTG | GAT | GAT | CAT | ATC | ATC | AGG | ACA | GAT | CAA | GGC | CTT | CTG | CTA | 1923 |
| Ile | Arg | Val | Asp | Asp | His | Ile | Ile | Arg | Thr | Asp | Gln | Gly | Leu | Leu | Leu |      |
|     |     |     |     | 625 |     |     |     |     | 630 |     |     |     |     | 635 |     |      |
| CGT | AGT | CTA | CAA | CAG | AAG | GAT | TCA | GGC | AAT | TAC | CTC | TGC | CAT | GCG | GTG | 1971 |
| Arg | Ser | Leu | Gln | Gln | Lys | Asp | Ser | Gly | Asn | Tyr | Leu | Cys | His | Ala | Val |      |
|     |     |     | 640 |     |     |     |     | 645 |     |     |     |     | 650 |     |     |      |
| GAA | CAT | GGG | TTC | ATA | CAA | ACT | CTT | CTT | AAG | GTA | ACC | CTG | GAA | GTC | ATT | 2019 |
| Glu | His | Gly | Phe | Ile | Gln | Thr | Leu | Leu | Lys | Val | Thr | Leu | Glu | Val | Ile |      |
|     |     | 655 |     |     |     |     | 660 |     |     |     |     | 665 |     |     |     |      |
| GAC | ACA | GAG | CAT | TTG | GAA | GAA | CTT | CTT | CAT | AAA | GAT | GAT | GAT | GGA | GAT | 2067 |
| Asp | Thr | Glu | His | Leu | Glu | Glu | Leu | Leu | His | Lys | Asp | Asp | Asp | Gly | Asp |      |
|     | 670 |     |     |     |     | 675 |     |     |     |     | 680 |     |     |     |     |      |
| GGC | TCT | AAG | ACC | AAA | GAA | ATG | TCC | AAT | AGC | ATG | ACA | CCT | AGC | CAG | AAG | 2115 |

| | | | | | | | | | | | | | | | |
|---|---|---|---|---|---|---|---|---|---|---|---|---|---|---|---|
|Gly|Ser|Lys|Thr|Lys|Glu|Met|Ser|Asn|Ser|Met|Thr|Pro|Ser|Gln|Lys|
|685| | | |690| | | |695| | | | | |700| |

| | | | | | | | | | | | | | | | | |
|---|---|---|---|---|---|---|---|---|---|---|---|---|---|---|---|---|
|GTC|TGG|TAC|AGA|GAC|TTC|ATG|CAG|CTC|ATC|AAC|CAC|CCC|AAT|CTC|AAC|2163|
|Val|Trp|Tyr|Arg|Asp|Phe|Met|Gln|Leu|Ile|Asn|His|Pro|Asn|Leu|Asn| |
| | | | |705| | | |710| | | | | |715| | |
|ACG|ATG|GAT|GAG|TTC|TGT|GAA|CAA|GTT|TGG|AAA|AGG|GAC|CGA|AAA|CAA|2211|
|Thr|Met|Asp|Glu|Phe|Cys|Glu|Gln|Val|Trp|Lys|Arg|Asp|Arg|Lys|Gln| |
| | | |720| | | | |725| | | | |730| | | |
|CGT|CGG|CAA|AGG|CCA|GGA|CAT|ACC|CCA|GGG|AAC|AGT|AAC|AAA|TGG|AAG|2259|
|Arg|Arg|Gln|Arg|Pro|Gly|His|Thr|Pro|Gly|Asn|Ser|Asn|Lys|Trp|Lys| |
| | |735| | | | |740| | | | |745| | | | |
|CAC|TTA|CAA|GAA|AAT|AAG|AAA|GGT|AGA|AAC|AGG|AGG|ACC|CAC|GAA|TTT|2307|
|His|Leu|Gln|Glu|Asn|Lys|Lys|Gly|Arg|Asn|Arg|Arg|Thr|His|Glu|Phe| |
| | |750| | | | |755| | | | |760| | | | |
|GAG|AGG|GCA|CCC|AGG|AGT|GTC|TGAGCTGCAT|TACCTCTAGA|AACCTCAAAC| | | | | | |2358|
|Glu|Arg|Ala|Pro|Arg|Ser|Val| | | | | | | | | | |
|765| | | |770| | | | | | | | | | | | |

| | |
|---|---|
|AAGTAGAAAC TTGCCTAGAC AATAACTGGA AAAACAAATG CAATATACAT GAACTTTTTT|2418|
|CATGGCATTA TGTGGATGTT TACAATGGTG GGAAATTCAG CTGAGTTCCA CCAATTATAA|2478|
|ATTAAATCCA TGAGTAACTT TCCTAATAGG CTTTTTTTC CTAATACCAC CGGGTAAAAA|2538|
|GTAAGAGACA GCTGAACCCT CGTGGAGCCA TTCATACAGG TCCCTATTTA AGGAACGGAA|2598|
|TTC|2601|

(2) INFORMATION FOR SEQ ID NO:54:

(i) SEQUENCE CHARACTERISTICS:
        (A) LENGTH: 771 amino acids
        (B) TYPE: amino acid
        (D) TOPOLOGY: linear (ii) MOLECULE TYPE: protein (xi) SEQUENCE DESCRIPTION: SEQ ID NO:54:

| | | | | | | | | | | | | | | |
|---|---|---|---|---|---|---|---|---|---|---|---|---|---|---|
|Met|Gly|Trp|Leu|Thr|Arg|Ile|Val|Cys|Leu|Phe|Trp|Gly|Val|Leu|Leu|
|1| | | |5| | | | |10| | | | |15|
|Thr|Ala|Arg|Ala|Asn|Tyr|Gln|Asn|Gly|Lys|Asn|Asn|Val|Pro|Arg|Leu|
| | | |20| | | | |25| | | | |30| | |
|Lys|Leu|Ser|Tyr|Lys|Glu|Met|Leu|Glu|Ser|Asn|Asn|Val|Ile|Thr|Phe|
| | |35| | | | |40| | | | |45| | | |
|Asn|Gly|Leu|Ala|Asn|Ser|Ser|Tyr|His|Thr|Phe|Leu|Leu|Asp|Glu| |
| |50| | | | |55| | | | |60| | | | |
|Glu|Arg|Ser|Arg|Leu|Tyr|Val|Gly|Ala|Lys|Asp|His|Ile|Phe|Ser|Phe|
|65| | | | |70| | | | |75| | | | |80|
|Asp|Leu|Val|Asn|Ile|Lys|Asp|Phe|Gln|Lys|Ile|Val|Trp|Pro|Val|Ser|
| | | | |85| | | | |90| | | | |95| |
|Tyr|Thr|Arg|Arg|Asp|Glu|Cys|Lys|Trp|Ala|Gly|Lys|Asp|Ile|Leu|Lys|
| | | |100| | | | |105| | | | |110| | |
|Glu|Cys|Ala|Asn|Phe|Ile|Lys|Val|Leu|Lys|Ala|Tyr|Asn|Gln|Thr|His|
| | |115| | | | |120| | | | |125| | | |
|Leu|Tyr|Ala|Cys|Gly|Thr|Gly|Ala|Phe|His|Pro|Ile|Cys|Thr|Tyr|Ile|
| |130| | | | |135| | | | |140| | | | |
|Glu|Ile|Gly|His|His|Pro|Glu|Asp|Asn|Ile|Phe|Lys|Leu|Glu|Asn|Ser|
|145| | | | |150| | | | |155| | | | |160|
|His|Phe|Glu|Asn|Gly|Arg|Gly|Lys|Ser|Pro|Tyr|Asp|Pro|Lys|Leu|Leu|
| | | | |165| | | | |170| | | | |175| |
|Thr|Ala|Ser|Leu|Leu|Ile|Asp|Gly|Glu|Leu|Tyr|Ser|Gly|Thr|Ala|Ala|
| | | |180| | | | |185| | | | |190| | |

| Asp | Phe | Met | Gly | Arg | Asp | Phe | Ala | Ile | Phe | Arg | Thr | Leu | Gly | His | His |
|     |     | 195 |     |     |     |     | 200 |     |     |     |     | 205 |     |     |     |

| His | Pro | Ile | Arg | Thr | Glu | Gln | His | Asp | Ser | Arg | Trp | Leu | Asn | Asp | Pro |
|     |     | 210 |     |     |     |     | 215 |     |     |     |     | 220 |     |     |     |

| Lys | Phe | Ile | Ser | Ala | His | Leu | Ile | Ser | Glu | Ser | Asp | Asn | Pro | Glu | Asp |
| 225 |     |     |     |     | 230 |     |     |     |     | 235 |     |     |     |     | 240 |

| Asp | Lys | Val | Tyr | Phe | Phe | Arg | Glu | Asn | Ala | Ile | Asp | Gly | Glu | His |
|     |     |     |     | 245 |     |     |     |     | 250 |     |     |     |     | 255 |

| Ser | Gly | Lys | Ala | Thr | His | Ala | Arg | Ile | Gly | Gln | Ile | Cys | Lys | Asn | Asp |
|     |     |     |     | 260 |     |     |     |     | 265 |     |     |     |     | 270 |     |

| Phe | Gly | Gly | His | Arg | Ser | Leu | Val | Asn | Lys | Trp | Thr | Thr | Phe | Leu | Lys |
|     |     | 275 |     |     |     |     | 280 |     |     |     |     | 285 |     |     |     |

| Ala | Arg | Leu | Ile | Cys | Ser | Val | Pro | Gly | Pro | Asn | Gly | Ile | Asp | Thr | His |
|     | 290 |     |     |     |     | 295 |     |     |     |     | 300 |     |     |     |     |

| Phe | Asp | Glu | Leu | Gln | Asp | Val | Phe | Leu | Met | Asn | Phe | Lys | Asp | Pro | Lys |
| 305 |     |     |     |     | 310 |     |     |     |     | 315 |     |     |     |     | 320 |

| Asn | Pro | Val | Val | Tyr | Gly | Val | Phe | Thr | Thr | Ser | Ser | Asn | Ile | Phe | Lys |
|     |     |     |     | 325 |     |     |     |     | 330 |     |     |     |     | 335 |     |

| Gly | Ser | Ala | Val | Cys | Met | Tyr | Ser | Met | Ser | Asp | Val | Arg | Arg | Val | Phe |
|     |     |     | 340 |     |     |     |     | 345 |     |     |     |     | 350 |     |     |

| Leu | Gly | Pro | Tyr | Ala | His | Arg | Asp | Gly | Pro | Asn | Tyr | Gln | Trp | Val | Pro |
|     |     | 355 |     |     |     |     | 360 |     |     |     |     | 365 |     |     |     |

| Tyr | Gln | Gly | Arg | Val | Pro | Tyr | Pro | Arg | Pro | Gly | Thr | Cys | Pro | Ser | Lys |
|     | 370 |     |     |     |     | 375 |     |     |     |     | 380 |     |     |     |     |

| Thr | Phe | Gly | Gly | Phe | Asp | Ser | Thr | Lys | Asp | Leu | Pro | Asp | Asp | Val | Ile |
| 385 |     |     |     |     | 390 |     |     |     |     | 395 |     |     |     |     | 400 |

| Thr | Phe | Ala | Arg | Ser | His | Pro | Ala | Met | Tyr | Asn | Pro | Val | Phe | Pro | Met |
|     |     |     |     | 405 |     |     |     |     | 410 |     |     |     |     | 415 |     |

| Asn | Asn | Arg | Pro | Ile | Val | Ile | Lys | Thr | Asp | Val | Asn | Tyr | Gln | Phe | Thr |
|     |     |     | 420 |     |     |     |     | 425 |     |     |     |     | 430 |     |     |

| Gln | Ile | Val | Val | Asp | Arg | Val | Asp | Ala | Glu | Asp | Gly | Gln | Tyr | Asp | Val |
|     |     | 435 |     |     |     |     | 440 |     |     |     |     | 445 |     |     |     |

| Met | Phe | Ile | Gly | Thr | Asp | Val | Gly | Thr | Val | Leu | Lys | Val | Val | Ser | Ile |
|     | 450 |     |     |     |     | 455 |     |     |     |     | 460 |     |     |     |     |

| Pro | Lys | Glu | Thr | Trp | Tyr | Asp | Leu | Glu | Glu | Val | Leu | Leu | Glu | Glu | Met |
| 465 |     |     |     |     | 470 |     |     |     |     | 475 |     |     |     |     | 480 |

| Thr | Val | Phe | Arg | Glu | Pro | Thr | Ala | Ile | Ser | Ala | Met | Glu | Leu | Ser | Thr |
|     |     |     |     | 485 |     |     |     |     | 490 |     |     |     |     | 495 |     |

| Lys | Gln | Gln | Gln | Leu | Tyr | Ile | Gly | Ser | Thr | Ala | Gly | Val | Ala | Gln | Leu |
|     |     |     | 500 |     |     |     |     | 505 |     |     |     |     | 510 |     |     |

| Pro | Leu | His | Arg | Cys | Asp | Ile | Tyr | Gly | Lys | Ala | Cys | Ala | Glu | Cys | Cys |
|     |     | 515 |     |     |     |     | 520 |     |     |     |     | 525 |     |     |     |

| Leu | Ala | Arg | Asp | Pro | Tyr | Cys | Ala | Trp | Asp | Gly | Ser | Ala | Cys | Ser | Arg |
|     | 530 |     |     |     |     | 535 |     |     |     |     | 540 |     |     |     |     |

| Tyr | Phe | Pro | Thr | Ala | Lys | Arg | Arg | Thr | Arg | Arg | Gln | Asp | Ile | Arg | Asn |
| 545 |     |     |     |     | 550 |     |     |     |     | 555 |     |     |     |     | 560 |

| Gly | Asp | Pro | Leu | Thr | His | Cys | Ser | Asp | Leu | His | His | Asp | Asn | His | His |
|     |     |     |     | 565 |     |     |     |     | 570 |     |     |     |     | 575 |     |

| Gly | His | Ser | Pro | Glu | Glu | Arg | Ile | Ile | Tyr | Gly | Val | Glu | Asn | Ser | Ser |
|     |     |     | 580 |     |     |     |     | 585 |     |     |     |     | 590 |     |     |

| Thr | Phe | Leu | Glu | Cys | Ser | Pro | Lys | Ser | Gln | Arg | Ala | Leu | Val | Tyr | Trp |
|     |     | 595 |     |     |     |     | 600 |     |     |     |     | 605 |     |     |     |

| Gln | Phe | Gln | Arg | Arg | Asn | Glu | Glu | Arg | Lys | Glu | Glu | Ile | Arg | Val | Asp |

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     |     | 610 |     |     |     | 615 |     |     |     | 620 |     |     |
| Asp | His | Ile | Ile | Arg | Thr | Asp | Gln | Gly | Leu | Leu | Leu | Arg | Ser | Leu | Gln |
| 625 |     |     |     |     | 630 |     |     |     | 635 |     |     |     |     |     | 640 |
| Gln | Lys | Asp | Ser | Gly | Asn | Tyr | Leu | Cys | His | Ala | Val | Glu | His | Gly | Phe |
|     |     |     |     | 645 |     |     |     |     | 650 |     |     |     |     | 655 |     |
| Ile | Gln | Thr | Leu | Leu | Lys | Val | Thr | Leu | Glu | Val | Ile | Asp | Thr | Glu | His |
|     |     |     | 660 |     |     |     |     | 665 |     |     |     |     | 670 |     |     |
| Leu | Glu | Glu | Leu | Leu | His | Lys | Asp | Asp | Gly | Asp | Gly | Ser | Lys | Thr |
|     |     | 675 |     |     |     |     | 680 |     |     |     | 685 |     |     |     |
| Lys | Glu | Met | Ser | Asn | Ser | Met | Thr | Pro | Ser | Gln | Lys | Val | Trp | Tyr | Arg |
|     | 690 |     |     |     |     | 695 |     |     |     |     | 700 |     |     |     |     |
| Asp | Phe | Met | Gln | Leu | Ile | Asn | His | Pro | Asn | Leu | Asn | Thr | Met | Asp | Glu |
| 705 |     |     |     |     | 710 |     |     |     |     | 715 |     |     |     |     | 720 |
| Phe | Cys | Glu | Gln | Val | Trp | Lys | Arg | Asp | Arg | Lys | Gln | Arg | Arg | Gln | Arg |
|     |     |     |     | 725 |     |     |     |     | 730 |     |     |     |     | 735 |     |
| Pro | Gly | His | Thr | Pro | Gly | Asn | Ser | Asn | Lys | Trp | Lys | His | Leu | Gln | Glu |
|     |     |     | 740 |     |     |     |     | 745 |     |     |     |     | 750 |     |     |
| Asn | Lys | Lys | Gly | Arg | Asn | Arg | Arg | Thr | His | Glu | Phe | Glu | Arg | Ala | Pro |
|     |     | 755 |     |     |     |     | 760 |     |     |     |     | 765 |     |     |     |
| Arg | Ser | Val |     |     |     |     |     |     |     |     |     |     |     |     |     |
|     |     | 770 |     |     |     |     |     |     |     |     |     |     |     |     |     |

(2) INFORMATION FOR SEQ ID NO:55:

(i) SEQUENCE CHARACTERISTICS:
        (A) LENGTH: 1332 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 7..1329

(xi) SEQUENCE DESCRIPTION: SEQ ID NO:55:

|       |       |       |       |       |       |       |       |       |       |       |       |       |       |       |       |     |
| ----- | ----- | ----- | ----- | ----- | ----- | ----- | ----- | ----- | ----- | ----- | ----- | ----- | ----- | ----- | ----- | --- |
| GGAATA | ATG | ATG | GTA | TTA | TTA | CAT | GCT | GTA | TAC | TCT | ATA | GTC | TTT | GTA |       | 48  |
|       | Met | Met | Val | Leu | Leu | His | Ala | Val | Tyr | Ser | Ile | Val | Phe | Val |       |     |
|       | 1   |     |     |     | 5   |     |     |     |     | 10  |     |     |     |     |       |     |
| GAT | GTT | ATA | ATC | ATA | AAA | GTA | CAG | AGG | TAT | ATC | AAC | GAT | ATT | CTA | ACT | 96  |
| Asp | Val | Ile | Ile | Ile | Lys | Val | Gln | Arg | Tyr | Ile | Asn | Asp | Ile | Leu | Thr |     |
| 15  |     |     |     |     | 20  |     |     |     |     | 25  |     |     |     |     | 30  |     |
| CTT | GAC | ATT | TTT | TAT | TTA | TTT | AAA | ATG | ATA | CCT | TTG | TTA | TTT | ATT | TTA | 144 |
| Leu | Asp | Ile | Phe | Tyr | Leu | Phe | Lys | Met | Ile | Pro | Leu | Leu | Phe | Ile | Leu |     |
|     |     |     |     | 35  |     |     |     |     | 40  |     |     |     |     | 45  |     |     |
| TTC | TAT | TTT | GCT | AAC | GGT | ATC | GAA | TGG | CAT | AAG | TTT | GAA | ACG | AGT | GAA | 192 |
| Phe | Tyr | Phe | Ala | Asn | Gly | Ile | Glu | Trp | His | Lys | Phe | Glu | Thr | Ser | Glu |     |
|     |     |     | 50  |     |     |     |     | 55  |     |     |     |     | 60  |     |     |     |
| GAA | ATA | ATT | TCT | ACT | TAC | TTA | TTA | GAC | GAC | GTA | TTA | TAC | ACG | GGT | GTT | 240 |
| Glu | Ile | Ile | Ser | Thr | Tyr | Leu | Leu | Asp | Asp | Val | Leu | Tyr | Thr | Gly | Val |     |
|     |     | 65  |     |     |     |     | 70  |     |     |     |     | 75  |     |     |     |     |
| AAT | GGG | GCG | GTA | TAC | ACA | TTT | TCA | AAT | AAT | AAA | CTA | AAC | AAA | ACT | GGT | 288 |
| Asn | Gly | Ala | Val | Tyr | Thr | Phe | Ser | Asn | Asn | Lys | Leu | Asn | Lys | Thr | Gly |     |
|     | 80  |     |     |     |     | 85  |     |     |     |     | 90  |     |     |     |     |     |
| TTA | ACT | AAT | AAT | AAT | TAT | ATA | ACA | ACA | TCT | ATA | AAA | GTA | GAG | GAT | GCG | 336 |
| Leu | Thr | Asn | Asn | Asn | Tyr | Ile | Thr | Thr | Ser | Ile | Lys | Val | Glu | Asp | Ala |     |
| 95  |     |     |     |     | 100 |     |     |     |     | 105 |     |     |     |     | 110 |     |
| GAT | AAG | GAT | ACA | TTA | GTA | TGC | GGA | ACC | AAT | AAC | GGA | AAT | CCC | AAA | TGT | 384 |
| Asp | Lys | Asp | Thr | Leu | Val | Cys | Gly | Thr | Asn | Asn | Gly | Asn | Pro | Lys | Cys |     |

|  |  |  |  |  |  |  |  |  |  |  |  |  |  |  |  |
|---|---|---|---|---|---|---|---|---|---|---|---|---|---|---|---|
| TGG | AAA | ATA | GAC | GGT | TCA | GAC | GAC | CCA | AAA | CAT | AGA | GGT | AGA | GGA | TAC |
| Trp | Lys | Ile | Asp | Gly | Ser | Asp | Asp | Pro | Lys | His | Arg | Gly | Arg | Gly | Tyr |
|  |  |  | 130 |  |  |  |  | 135 |  |  |  |  | 140 |  |  |

```
                                115                        120                        125
TGG AAA ATA GAC GGT TCA GAC GAC CCA AAA CAT AGA GGT AGA GGA TAC                          432
Trp Lys Ile Asp Gly Ser Asp Asp Pro Lys His Arg Gly Arg Gly Tyr
            130             135             140

GCT CCT TAT CAA AAT AGC AAA GTA ACG ATA ATC AGT CAC AAC GGA TGT                          480
Ala Pro Tyr Gln Asn Ser Lys Val Thr Ile Ile Ser His Asn Gly Cys
            145             150             155

GTA CTA TCT GAC ATA AAC ATA TCA AAA GAA GGA ATT AAA CGA TGG AGA                          528
Val Leu Ser Asp Ile Asn Ile Ser Lys Glu Gly Ile Lys Arg Trp Arg
            160             165             170

AGA TTT GAC GGA CCA TGT GGT TAT GAT TTA TAC ACG GCG GAT AAC GTA                          576
Arg Phe Asp Gly Pro Cys Gly Tyr Asp Leu Tyr Thr Ala Asp Asn Val
175             180             185             190

ATT CCA AAA GAT GGT TTA CGA GGA GCA TTC GTC GAT AAA GAT GGT ACT                          624
Ile Pro Lys Asp Gly Leu Arg Gly Ala Phe Val Asp Lys Asp Gly Thr
            195             200             205

TAT GAC AAA GTT TAC ATT CTT TTC ACT GAT ACT ATC GGC TCA AAG AGA                          672
Tyr Asp Lys Val Tyr Ile Leu Phe Thr Asp Thr Ile Gly Ser Lys Arg
            210             215             220

ATT GTC AAA ATT CCG TAT ATA GCA CAA ATG TGC CTA AAC GAC GAA GGT                          720
Ile Val Lys Ile Pro Tyr Ile Ala Gln Met Cys Leu Asn Asp Glu Gly
        225             230             235

GGT CCA TCA TCA TTG TCT AGT CAT AGA TGG TCG ACG TTT CTC AAA GTC                          768
Gly Pro Ser Ser Leu Ser Ser His Arg Trp Ser Thr Phe Leu Lys Val
        240             245             250

GAA TTA GAA TGT GAT ATC GAC GGA AGA AGT TAT AGA CAA ATT ATT CAT                          816
Glu Leu Glu Cys Asp Ile Asp Gly Arg Ser Tyr Arg Gln Ile Ile His
255             260             265             270

TCT AGA ACT ATA AAA ACA GAT AAT GAT ACG ATA CTA TAT GTA TTC TTC                          864
Ser Arg Thr Ile Lys Thr Asp Asn Asp Thr Ile Leu Tyr Val Phe Phe
            275             280             285

GAT AGT CCT TAT TCC AAG TCC GCA TTA TGT ACC TAT TCT ATG AAT ACC                          912
Asp Ser Pro Tyr Ser Lys Ser Ala Leu Cys Thr Tyr Ser Met Asn Thr
            290             295             300

ATT AAA CAA TCT TTT TCT ACG TCA AAA TTG GAA GGA TAT ACA AAG CAA                          960
Ile Lys Gln Ser Phe Ser Thr Ser Lys Leu Glu Gly Tyr Thr Lys Gln
        305             310             315

TTG CCG TCG CCA GCC TCT GGT ATA TGT CTA CCA GCT GGA AAA GTT GTT                         1008
Leu Pro Ser Pro Ala Ser Gly Ile Cys Leu Pro Ala Gly Lys Val Val
    320             325             330

CCA CAT ACC ACG TTT GAA GTC ATA GAA AAA TAT AAT GTA CTA GAT GAT                         1056
Pro His Thr Thr Phe Glu Val Ile Glu Lys Tyr Asn Val Leu Asp Asp
335             340             345             350

ATT ATA AAG CCT TTA TCT AAC CAA CCT ATC TTC GAA GGA CCG TCT GGT                         1104
Ile Ile Lys Pro Leu Ser Asn Gln Pro Ile Phe Glu Gly Pro Ser Gly
            355             360             365

GTT AAA TGG TTC GAT ATA AAG GAG AAG GAA AAT GAA CAT CGG GAA TAT                         1152
Val Lys Trp Phe Asp Ile Lys Glu Lys Glu Asn Glu His Arg Glu Tyr
        370             375             380

AGA ATA TAC TTC ATA AAA GAA AAT TCT ATA TAT TCG TTC GAT ACA AAA                         1200
Arg Ile Tyr Phe Ile Lys Glu Asn Ser Ile Tyr Ser Phe Asp Thr Lys
        385             390             395

TCT AAA CAA ACT CGT AGC TCG CAA GTC GAT GCG CGA CTA TTT TCA GTA                         1248
Ser Lys Gln Thr Arg Ser Ser Gln Val Asp Ala Arg Leu Phe Ser Val
    400             405             410

ATG GTA ACT TCG AAA CCG TTA TTT ATA GCA GAT ATA GGG ATA GGA GTA                         1296
Met Val Thr Ser Lys Pro Leu Phe Ile Ala Asp Ile Gly Ile Gly Val
415             420             425             430

GGA ATG CCA CAA ATG AAA AAA ATA CTT AAA ATG TAA                                         1332
Gly Met Pro Gln Met Lys Lys Ile Leu Lys Met
```

435            440

(2) INFORMATION FOR SEQ ID NO:56:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO:56:

```
Met Met Val Leu Leu His Ala Val Tyr Ser Ile Val Phe Val Asp Val
 1               5                  10                  15
Ile Ile Ile Lys Val Gln Arg Tyr Ile Asn Asp Ile Leu Thr Leu Asp
             20                  25                  30
Ile Phe Tyr Leu Phe Lys Met Ile Pro Leu Leu Phe Ile Leu Phe Tyr
                 35                  40                  45
Phe Ala Asn Gly Ile Glu Trp His Lys Phe Glu Thr Ser Glu Glu Ile
         50                  55                  60
Ile Ser Thr Tyr Leu Leu Asp Asp Val Leu Tyr Thr Gly Val Asn Gly
 65                  70                  75                  80
Ala Val Tyr Thr Phe Ser Asn Asn Lys Leu Asn Lys Thr Gly Leu Thr
                 85                  90                  95
Asn Asn Asn Tyr Ile Thr Thr Ser Ile Lys Val Glu Asp Ala Asp Lys
                100                 105                 110
Asp Thr Leu Val Cys Gly Thr Asn Asn Gly Asn Pro Lys Cys Trp Lys
             115                 120                 125
Ile Asp Gly Ser Asp Asp Pro Lys His Arg Gly Arg Gly Tyr Ala Pro
         130                 135                 140
Tyr Gln Asn Ser Lys Val Thr Ile Ile Ser His Asn Gly Cys Val Leu
145                 150                 155                 160
Ser Asp Ile Asn Ile Ser Lys Glu Gly Ile Lys Arg Trp Arg Arg Phe
                165                 170                 175
Asp Gly Pro Cys Gly Tyr Asp Leu Tyr Thr Ala Asp Asn Val Ile Pro
             180                 185                 190
Lys Asp Gly Leu Arg Gly Ala Phe Val Asp Lys Asp Gly Thr Tyr Asp
         195                 200                 205
Lys Val Tyr Ile Leu Phe Thr Asp Thr Ile Gly Ser Lys Arg Ile Val
210                 215                 220
Lys Ile Pro Tyr Ile Ala Gln Met Cys Leu Asn Asp Glu Gly Gly Pro
225                 230                 235                 240
Ser Ser Leu Ser Ser His Arg Trp Ser Thr Phe Leu Lys Val Glu Leu
                245                 250                 255
Glu Cys Asp Ile Asp Gly Arg Ser Tyr Arg Gln Ile Ile His Ser Arg
             260                 265                 270
Thr Ile Lys Thr Asp Asn Asp Thr Ile Leu Tyr Val Phe Phe Asp Ser
         275                 280                 285
Pro Tyr Ser Lys Ser Ala Leu Cys Thr Tyr Ser Met Asn Thr Ile Lys
     290                 295                 300
Gln Ser Phe Ser Thr Ser Lys Leu Glu Gly Tyr Thr Lys Gln Leu Pro
305                 310                 315                 320
Ser Pro Ala Ser Gly Ile Cys Leu Pro Ala Gly Lys Val Val Pro His
             325                 330                 335
Thr Thr Phe Glu Val Ile Glu Lys Tyr Asn Val Leu Asp Asp Ile Ile
         340                 345                 350
```

```
Lys  Pro  Leu  Ser  Asn  Gln  Pro  Ile  Phe  Glu  Gly  Pro  Ser  Gly  Val  Lys
          355                     360                    365

Trp  Phe  Asp  Ile  Lys  Glu  Lys  Glu  Asn  Glu  His  Arg  Glu  Tyr  Arg  Ile
          370                     375                    380

Tyr  Phe  Ile  Lys  Glu  Asn  Ser  Ile  Tyr  Ser  Phe  Asp  Thr  Lys  Ser  Lys
385                          390                    395                         400

Gln  Thr  Arg  Ser  Ser  Gln  Val  Asp  Ala  Arg  Leu  Phe  Ser  Val  Met  Val
                    405                    410                    415

Thr  Ser  Lys  Pro  Leu  Phe  Ile  Ala  Asp  Ile  Gly  Ile  Gly  Val  Gly  Met
               420                    425                         430

Pro  Gln  Met  Lys  Lys  Ile  Leu  Lys  Met
               435                    440
```

( 2 ) INFORMATION FOR SEQ ID NO:57:

( i ) SEQUENCE CHARACTERISTICS:
        ( A ) LENGTH: 2854 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 451..2640

( x i ) SEQUENCE DESCRIPTION: SEQ ID NO:57:

```
ATTCCACCTC  CCGCTGACCG  CCTACGCCGC  GACGATCTTT  CCTCTCGCCA  GGCGAAAACT        60

ACGACGTGTC  AACAACATTT  TTGTTTTTTC  TGCTTCCGTG  TTTTCATGTT  CCGTGAAACC       120

GCTTCTCGCA  TTACCACTCT  TCCGTTTCCC  AGTGTTTGTT  TTCTCCGTTT  CTTTCATCGT       180

GGATGTTTTG  TTTTGGTGTA  GCGAGTGACG  AGCTTATGTC  ATTAAACGTA  CATCCAATCT       240

GTCGGTATAT  TGGTGTGTGA  TATTTACTA   TTATATATTT  AGCCATCACT  TGAAAGCCGT       300

GAAAAATTTT  TGAAAGTGGA  GAGGAAAAAG  AAAAGGCGCA  GAAGGCTTTT  TAAGCTTCAT       360

GGATATGTGC  TCTACGCTTC  AACTACTGTC  GCAGAATCAT  CTTCCGGGAA  AGGAAATTTC       420

GCCTGAAATG  GTGCCGCGGC  CGCACTGAAC  ATG CGG GCG GCG CTG GTG GCC GTC         474
                                   Met Arg Ala Ala Leu Val Ala Val
                                     1               5

GCG GCG CTG CTT TGG GTG GCG CTG CAC GCC GCC GCA TGG GTC AAC GAC             522
Ala Ala Leu Leu Trp Val Ala Leu His Ala Ala Ala Trp Val Asn Asp
         10                  15                  20

GTC AGC CCC AAG ATG TAC GTC CAG TTC GGT GAG GAA CGG GTG CAA CGC             570
Val Ser Pro Lys Met Tyr Val Gln Phe Gly Glu Glu Arg Val Gln Arg
 25                  30                  35                  40

TTC CTG GGC AAT GAA TCG CAC AAA GAC CAC TTC AAG CTG CTG GAG AAG             618
Phe Leu Gly Asn Glu Ser His Lys Asp His Phe Lys Leu Leu Glu Lys
             45                  50                  55

GAC CAC AAC TCG CTC CTC GTA GGA GCT AGG AAC ATC GTC TAC AAT ATC             666
Asp His Asn Ser Leu Leu Val Gly Ala Arg Asn Ile Val Tyr Asn Ile
                 60                  65                  70

AGC CTT CGA GAC CTC ACA GAA TTC ACC GAG CAG AGG ATC GAG TGG CAC             714
Ser Leu Arg Asp Leu Thr Glu Phe Thr Glu Gln Arg Ile Glu Trp His
         75                  80                  85

TCG TCA GGT GCC CAT CGC GAG CTC TGC TAC CTC AAG GGG AAG TCA GAG             762
Ser Ser Gly Ala His Arg Glu Leu Cys Tyr Leu Lys Gly Lys Ser Glu
     90                  95                 100

GAC GAC TGC CAG AAC TAC ATC CGA GTC CTG GCG AAA ATT GAC GAT GAC             810
Asp Asp Cys Gln Asn Tyr Ile Arg Val Leu Ala Lys Ile Asp Asp Asp
```

-continued

| | | | | | | | | | | | | | | | | |
|---|---|---|---|---|---|---|---|---|---|---|---|---|---|---|---|---|
| | 105 | | | | 110 | | | | | 115 | | | | 120 | | |
| CGC | GTA | CTC | ATC | TGC | GGT | ACG | AAC | GCC | TAT | AAG | CCA | CTA | TGT | CGG | CAC | 858 |
| Arg | Val | Leu | Ile | Cys | Gly | Thr | Asn | Ala | Tyr | Lys | Pro | Leu | Cys | Arg | His | |
| | | | | 125 | | | | | 130 | | | | | 135 | | |
| TAC | GCC | CTC | AAG | GAT | GGA | GAT | TAT | GTT | GTA | GAG | AAA | GAA | TAT | GAG | GGA | 906 |
| Tyr | Ala | Leu | Lys | Asp | Gly | Asp | Tyr | Val | Val | Glu | Lys | Glu | Tyr | Glu | Gly | |
| | | | 140 | | | | | 145 | | | | | 150 | | | |
| AGA | GGA | TTG | TGC | CCA | TTT | GAC | CCT | GAC | CAC | AAC | AGC | ACT | GCA | ATA | TAC | 954 |
| Arg | Gly | Leu | Cys | Pro | Phe | Asp | Pro | Asp | His | Asn | Ser | Thr | Ala | Ile | Tyr | |
| | | | 155 | | | | | 160 | | | | | 165 | | | |
| AGT | GAG | GGA | CAA | TTG | TAC | TCA | GCA | ACA | GTG | GCA | GAC | TTC | TCT | GGA | ACT | 1002 |
| Ser | Glu | Gly | Gln | Leu | Tyr | Ser | Ala | Thr | Val | Ala | Asp | Phe | Ser | Gly | Thr | |
| | | 170 | | | | | 175 | | | | | 180 | | | | |
| GAC | CCT | CTC | ATA | TAC | CGC | GGC | CCT | CTA | AGA | ACA | GAG | AGA | TCT | GAC | CTC | 1050 |
| Asp | Pro | Leu | Ile | Tyr | Arg | Gly | Pro | Leu | Arg | Thr | Glu | Arg | Ser | Asp | Leu | |
| 185 | | | | | 190 | | | | | 195 | | | | | 200 | |
| AAA | CAA | TTA | AAT | GCT | CCT | AAC | TTT | GTC | AAC | ACA | ATG | GAG | TAC | AAT | GAT | 1098 |
| Lys | Gln | Leu | Asn | Ala | Pro | Asn | Phe | Val | Asn | Thr | Met | Glu | Tyr | Asn | Asp | |
| | | | | 205 | | | | | 210 | | | | | 215 | | |
| TTT | ATA | TTC | TTC | TTC | TTC | CGA | GAG | ACT | GCT | GTT | GAG | TAC | ATC | AAC | TGC | 1146 |
| Phe | Ile | Phe | Phe | Phe | Phe | Arg | Glu | Thr | Ala | Val | Glu | Tyr | Ile | Asn | Cys | |
| | | | 220 | | | | | 225 | | | | | 230 | | | |
| GGA | AAG | GCT | ATC | TAT | TCA | AGA | GTT | GCC | AGA | GTC | TGT | AAA | CAT | GAC | AAG | 1194 |
| Gly | Lys | Ala | Ile | Tyr | Ser | Arg | Val | Ala | Arg | Val | Cys | Lys | His | Asp | Lys | |
| | | 235 | | | | | 240 | | | | | 245 | | | | |
| GGC | GGC | CCT | CAT | CAG | GGT | GGT | GAC | AGA | TGG | ACT | TCT | TTT | TTG | AAA | TCA | 1242 |
| Gly | Gly | Pro | His | Gln | Gly | Gly | Asp | Arg | Trp | Thr | Ser | Phe | Leu | Lys | Ser | |
| | | 250 | | | | | 255 | | | | | 260 | | | | |
| CGT | CTG | AAC | TGT | TCC | GTC | CCT | GGA | GAT | TAT | CCA | TTT | TAC | TTC | AAT | GAA | 1290 |
| Arg | Leu | Asn | Cys | Ser | Val | Pro | Gly | Asp | Tyr | Pro | Phe | Tyr | Phe | Asn | Glu | |
| 265 | | | | | 270 | | | | | 275 | | | | | 280 | |
| ATT | CAG | TCA | ACA | AGT | GAC | ATC | ATT | GAA | GGA | AAT | TAT | GGT | GGT | CAA | GTG | 1338 |
| Ile | Gln | Ser | Thr | Ser | Asp | Ile | Ile | Glu | Gly | Asn | Tyr | Gly | Gly | Gln | Val | |
| | | | | 285 | | | | | 290 | | | | | 295 | | |
| GAG | AAA | CTC | ATC | TAC | GGT | GTC | TTC | ACG | ACA | CCA | GTG | AAC | TCT | ATT | GGT | 1386 |
| Glu | Lys | Leu | Ile | Tyr | Gly | Val | Phe | Thr | Thr | Pro | Val | Asn | Ser | Ile | Gly | |
| | | | 300 | | | | | 305 | | | | | 310 | | | |
| GGC | TCT | GCT | GTT | TGT | GCC | TTC | AGT | ATG | AAG | TCA | ATA | CTT | GAG | TCA | TTT | 1434 |
| Gly | Ser | Ala | Val | Cys | Ala | Phe | Ser | Met | Lys | Ser | Ile | Leu | Glu | Ser | Phe | |
| | | 315 | | | | | 320 | | | | | 325 | | | | |
| GAT | GGT | CCA | TTT | AAA | GAG | CAG | GAA | ACG | ATG | AAC | TCA | AAC | TGG | TTG | GCA | 1482 |
| Asp | Gly | Pro | Phe | Lys | Glu | Gln | Glu | Thr | Met | Asn | Ser | Asn | Trp | Leu | Ala | |
| | 330 | | | | | 335 | | | | | 340 | | | | | |
| GTG | CCA | AGC | CTT | AAA | GTG | CCA | GAA | CCA | AGG | CCT | GGA | CAA | TGT | GTG | AAT | 1530 |
| Val | Pro | Ser | Leu | Lys | Val | Pro | Glu | Pro | Arg | Pro | Gly | Gln | Cys | Val | Asn | |
| 345 | | | | | 350 | | | | | 355 | | | | | 360 | |
| GAC | AGT | CGT | ACA | CTT | CCT | GAT | GTG | TCT | GTC | AAT | TTT | GTA | AAG | TCA | CAT | 1578 |
| Asp | Ser | Arg | Thr | Leu | Pro | Asp | Val | Ser | Val | Asn | Phe | Val | Lys | Ser | His | |
| | | | 365 | | | | | 370 | | | | | 375 | | | |
| ACA | CTG | ATG | GAT | GAG | GCC | GTG | CCA | GCA | TTT | TTT | ACT | CGG | CCA | ATT | CTC | 1626 |
| Thr | Leu | Met | Asp | Glu | Ala | Val | Pro | Ala | Phe | Phe | Thr | Arg | Pro | Ile | Leu | |
| | | | 380 | | | | | 385 | | | | | 390 | | | |
| ATT | CGG | ATC | AGC | TTA | CAG | TAC | AGA | TTT | ACA | AAA | ATA | GCT | GTT | GAT | CAA | 1674 |
| Ile | Arg | Ile | Ser | Leu | Gln | Tyr | Arg | Phe | Thr | Lys | Ile | Ala | Val | Asp | Gln | |
| | | 395 | | | | | 400 | | | | | 405 | | | | |
| CAA | GTC | CGA | ACA | CCA | GAT | GGG | AAA | GCG | TAT | GAT | GTC | CTG | TTT | ATA | GGA | 1722 |
| Gln | Val | Arg | Thr | Pro | Asp | Gly | Lys | Ala | Tyr | Asp | Val | Leu | Phe | Ile | Gly | |
| | 410 | | | | | 415 | | | | | 420 | | | | | |
| ACT | GAT | GAT | GGC | AAA | GTG | ATA | AAA | GCT | TTG | AAC | TCT | GCC | TCC | TTT | GAT | 1770 |
| Thr | Asp | Asp | Gly | Lys | Val | Ile | Lys | Ala | Leu | Asn | Ser | Ala | Ser | Phe | Asp | |

```
   425                      430                      435                      440
TCA TCT GAT ACT GTA GAT AGT GTT GTA ATA GAA GAA CTG CAA GTG TTG        1818
Ser Ser Asp Thr Val Asp Ser Val Val Ile Glu Glu Leu Gln Val Leu
                445                      450                      455

CCA CCT GGA GTA CCT GTT AAG AAC CTG TAT GTG GTG CGA ATG GAT GGG        1866
Pro Pro Gly Val Pro Val Lys Asn Leu Tyr Val Val Arg Met Asp Gly
                460                      465                      470

GAT GAT AGC AAG CTG GTG GTT GTG TCT GAT GAT GAG ATT CTG GCA ATT        1914
Asp Asp Ser Lys Leu Val Val Val Ser Asp Asp Glu Ile Leu Ala Ile
                475                      480                      485

AAG CTT CAT CGT TGT GGC TCA GAT AAA ATA ACA AAT TGT CGA GAA TGT        1962
Lys Leu His Arg Cys Gly Ser Asp Lys Ile Thr Asn Cys Arg Glu Cys
        490                      495                      500

GTG TCC TTG CAA GAT CCT TAC TGT GCA TGG GAC AAT GTA GAA TTA AAA        2010
Val Ser Leu Gln Asp Pro Tyr Cys Ala Trp Asp Asn Val Glu Leu Lys
505                      510                      515                      520

TGT ACA GCT GTA GGT TCA CCA GAC TGG AGT GCT GGA AAA AGA CGC TTT        2058
Cys Thr Ala Val Gly Ser Pro Asp Trp Ser Ala Gly Lys Arg Arg Phe
                525                      530                      535

ATT CAG AAC ATT TCA CTC GGT GAA CAT AAA GCT TGT GGT GGA CGT CCA        2106
Ile Gln Asn Ile Ser Leu Gly Glu His Lys Ala Cys Gly Gly Arg Pro
                540                      545                      550

CAA ACA GAA ATC GTT GCT TCT CCT GTA CCA ACT CAG CCG ACG ACA AAA        2154
Gln Thr Glu Ile Val Ala Ser Pro Val Pro Thr Gln Pro Thr Thr Lys
        555                      560                      565

TCT AGT GGC GAT CCC GTT CAT TCA ATC CAC CAG GCT GAA TTT GAA CCT        2202
Ser Ser Gly Asp Pro Val His Ser Ile His Gln Ala Glu Phe Glu Pro
        570                      575                      580

GAA ATT GAC AAC GAG ATT GTT ATT GGA GTA GAT GAC AGC AAC GTC ATT        2250
Glu Ile Asp Asn Glu Ile Val Ile Gly Val Asp Asp Ser Asn Val Ile
585                      590                      595                      600

CCT AAT ACC CTG GCT GAA ATA AAT CAT GCA GGT TCA AAG CTG CCT TCC        2298
Pro Asn Thr Leu Ala Glu Ile Asn His Ala Gly Ser Lys Leu Pro Ser
                605                      610                      615

TCC CAG GAA AAG TTG CCT ATT TAT ACA GCG GAG ACT CTG ACT ATT GCT        2346
Ser Gln Glu Lys Leu Pro Ile Tyr Thr Ala Glu Thr Leu Thr Ile Ala
                620                      625                      630

ATA GTT ACA TCA TGC CTT GGA GCT CTA GTT GTT GGC TTC ATC TCT GGA        2394
Ile Val Thr Ser Cys Leu Gly Ala Leu Val Val Gly Phe Ile Ser Gly
        635                      640                      645

TTT CTT TTT TCT CGG CGA TGC AGG GGA GAG GAT TAC ACA GAC ATG CCT        2442
Phe Leu Phe Ser Arg Arg Cys Arg Gly Glu Asp Tyr Thr Asp Met Pro
        650                      655                      660

TTT CCA GAT CAA CGC CAT CAG CTA AAT AGG CTC ACT GAG GCT GGT CTG        2490
Phe Pro Asp Gln Arg His Gln Leu Asn Arg Leu Thr Glu Ala Gly Leu
665                      670                      675                      680

AAT GCA GAC TCA CCC TAT CTT CCA CCC TGT GCC AAT AAC AAG GCA GCC        2538
Asn Ala Asp Ser Pro Tyr Leu Pro Pro Cys Ala Asn Asn Lys Ala Ala
                685                      690                      695

ATA AAT CTT GTG CTC AAT GTC CCA CCA AAG AAT GCA AAT GGA AAA AAT        2586
Ile Asn Leu Val Leu Asn Val Pro Pro Lys Asn Ala Asn Gly Lys Asn
                700                      705                      710

GCC AAC TCT TCA GCT GAA AAC AAA CCA ATA CAG AAA GTA AAA AAG ACA        2634
Ala Asn Ser Ser Ala Glu Asn Lys Pro Ile Gln Lys Val Lys Lys Thr
        715                      720                      725

TAC ATT TAGCAGAAAT CTTTGGTATC TGTTTTGGTG CAGACCCATG CCACTAGAGT         2690
Tyr Ile
        730

AACCAAGACT CTATTGAGAA ATGTCCTCAA GAAAGTTAAA AAGATGTAGA CTTCTGTAAT      2750
```

| CGAGAGCACC | ACTTTCCATA | GTAATACAGA | ACAATGTGAA | ATAAATACTA | CAGAAGAAGT | 2810 |
| CTTTGTTACA | CAAAAAAGTG | TATAGTGATC | TGTGATCAGT | TTCG | | 2854 |

( 2 ) INFORMATION FOR SEQ ID NO:58:

( i ) SEQUENCE CHARACTERISTICS:
        ( A ) LENGTH: 730 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Met Arg Ala Ala Leu Val Ala Val Ala Ala Leu Leu Trp Val Ala Leu
  1               5                  10                  15

His Ala Ala Ala Trp Val Asn Asp Val Ser Pro Lys Met Tyr Val Gln
             20                  25                  30

Phe Gly Glu Glu Arg Val Gln Arg Phe Leu Gly Asn Glu Ser His Lys
         35                  40                  45

Asp His Phe Lys Leu Leu Glu Lys Asp His Asn Ser Leu Leu Val Gly
     50                  55                  60

Ala Arg Asn Ile Val Tyr Asn Ile Ser Leu Arg Asp Leu Thr Glu Phe
 65                  70                  75                  80

Thr Glu Gln Arg Ile Glu Trp His Ser Ser Gly Ala His Arg Glu Leu
                 85                  90                  95

Cys Tyr Leu Lys Gly Lys Ser Glu Asp Cys Gln Asn Tyr Ile Arg
            100                 105                 110

Val Leu Ala Lys Ile Asp Asp Arg Val Leu Ile Cys Gly Thr Asn
        115                 120                 125

Ala Tyr Lys Pro Leu Cys Arg His Tyr Ala Leu Lys Asp Gly Asp Tyr
130                 135                 140

Val Val Glu Lys Glu Tyr Glu Gly Arg Gly Leu Cys Pro Phe Asp Pro
145                 150                 155                 160

Asp His Asn Ser Thr Ala Ile Tyr Ser Glu Gly Gln Leu Tyr Ser Ala
                165                 170                 175

Thr Val Ala Asp Phe Ser Gly Thr Asp Pro Leu Ile Tyr Arg Gly Pro
            180                 185                 190

Leu Arg Thr Glu Arg Ser Asp Leu Lys Gln Leu Asn Ala Pro Asn Phe
        195                 200                 205

Val Asn Thr Met Glu Tyr Asn Asp Phe Ile Phe Phe Phe Arg Glu
210                 215                 220

Thr Ala Val Glu Tyr Ile Asn Cys Gly Lys Ala Ile Tyr Ser Arg Val
225                 230                 235                 240

Ala Arg Val Cys Lys His Asp Lys Gly Gly Pro His Gln Gly Gly Asp
                245                 250                 255

Arg Trp Thr Ser Phe Leu Lys Ser Arg Leu Asn Cys Ser Val Pro Gly
            260                 265                 270

Asp Tyr Pro Phe Tyr Phe Asn Glu Ile Gln Ser Thr Ser Asp Ile Ile
        275                 280                 285

Glu Gly Asn Tyr Gly Gly Gln Val Glu Lys Leu Ile Tyr Gly Val Phe
290                 295                 300

Thr Thr Pro Val Asn Ser Ile Gly Gly Ser Ala Val Cys Ala Phe Ser
305                 310                 315                 320

Met Lys Ser Ile Leu Glu Ser Phe Asp Gly Pro Phe Lys Glu Gln Glu
                325                 330                 335

Thr Met Asn Ser Asn Trp Leu Ala Val Pro Ser Leu Lys Val Pro Glu
```

|  | 340 |  |  |  | 345 |  |  |  | 350 |  |  |
|---|---|---|---|---|---|---|---|---|---|---|---|

Pro Arg Pro Gly Gln Cys Val Asn Asp Ser Arg Thr Leu Pro Asp Val
    355             360             365

Ser Val Asn Phe Val Lys Ser His Thr Leu Met Asp Glu Ala Val Pro
    370             375             380

Ala Phe Phe Thr Arg Pro Ile Leu Ile Arg Ile Ser Leu Gln Tyr Arg
385             390             395             400

Phe Thr Lys Ile Ala Val Asp Gln Gln Val Arg Thr Pro Asp Gly Lys
            405             410             415

Ala Tyr Asp Val Leu Phe Ile Gly Thr Asp Asp Gly Lys Val Ile Lys
            420             425             430

Ala Leu Asn Ser Ala Ser Phe Asp Ser Ser Asp Thr Val Asp Ser Val
            435             440             445

Val Ile Glu Glu Leu Gln Val Leu Pro Pro Gly Val Pro Val Lys Asn
    450             455             460

Leu Tyr Val Val Arg Met Asp Gly Asp Asp Ser Lys Leu Val Val Val
465             470             475             480

Ser Asp Asp Glu Ile Leu Ala Ile Lys Leu His Arg Cys Gly Ser Asp
            485             490             495

Lys Ile Thr Asn Cys Arg Glu Cys Val Ser Leu Gln Asp Pro Tyr Cys
            500             505             510

Ala Trp Asp Asn Val Glu Leu Lys Cys Thr Ala Val Gly Ser Pro Asp
            515             520             525

Trp Ser Ala Gly Lys Arg Arg Phe Ile Gln Asn Ile Ser Leu Gly Glu
    530             535             540

His Lys Ala Cys Gly Gly Arg Pro Gln Thr Glu Ile Val Ala Ser Pro
545             550             555             560

Val Pro Thr Gln Pro Thr Thr Lys Ser Ser Gly Asp Pro Val His Ser
            565             570             575

Ile His Gln Ala Glu Phe Glu Pro Glu Ile Asp Asn Glu Ile Val Ile
            580             585             590

Gly Val Asp Asp Ser Asn Val Ile Pro Asn Thr Leu Ala Glu Ile Asn
    595             600             605

His Ala Gly Ser Lys Leu Pro Ser Ser Gln Glu Lys Leu Pro Ile Tyr
    610             615             620

Thr Ala Glu Thr Leu Thr Ile Ala Ile Val Thr Ser Cys Leu Gly Ala
625             630             635             640

Leu Val Val Gly Phe Ile Ser Gly Phe Leu Phe Ser Arg Arg Cys Arg
            645             650             655

Gly Glu Asp Tyr Thr Asp Met Pro Phe Pro Asp Gln Arg His Gln Leu
            660             665             670

Asn Arg Leu Thr Glu Ala Gly Leu Asn Ala Asp Ser Pro Tyr Leu Pro
    675             680             685

Pro Cys Ala Asn Asn Lys Ala Ala Ile Asn Leu Val Leu Asn Val Pro
    690             695             700

Pro Lys Asn Ala Asn Gly Lys Asn Ala Asn Ser Ser Ala Glu Asn Lys
705             710             715             720

Pro Ile Gln Lys Val Lys Lys Thr Tyr Ile
            725             730

( 2 ) INFORMATION FOR SEQ ID NO:59:

( i ) SEQUENCE CHARACTERISTICS:
        ( A ) LENGTH: 3560 base pairs
        ( B ) TYPE: nucleic acid (C) STRANDEDNESS: double
(D) TOPOLOGY: linear (ii) MOLECULE TYPE: cDNA (ix) FEATURE:
(A) NAME/KEY: CDS
(B) LOCATION: 1..1953

(xi) SEQUENCE DESCRIPTION: SEQ ID NO:59:

| | | | | | | | | | | | | | | | | |
|---|---|---|---|---|---|---|---|---|---|---|---|---|---|---|---|---|
| GAG | GAT | GAT | TGT | CAG | AAT | TAC | ATC | CGC | ATC | ATG | GTG | GTG | CCA | TCG | CCG | 48 |
| Glu | Asp | Asp | Cys | Gln | Asn | Tyr | Ile | Arg | Ile | Met | Val | Val | Pro | Ser | Pro | |
| 1 | | | | 5 | | | | | 10 | | | | | 15 | | |
| GGT | CGC | CTT | TTC | GTT | TGT | GGC | ACC | AAC | TCG | TTC | CGG | CCC | ATG | TGC | AAC | 96 |
| Gly | Arg | Leu | Phe | Val | Cys | Gly | Thr | Asn | Ser | Phe | Arg | Pro | Met | Cys | Asn | |
| | | | 20 | | | | | 25 | | | | | 30 | | | |
| ACG | TAT | ATC | ATT | AGT | GAC | AGC | AAC | TAC | ACG | CTG | GAG | GCC | ACG | AAG | AAC | 144 |
| Thr | Tyr | Ile | Ile | Ser | Asp | Ser | Asn | Tyr | Thr | Leu | Glu | Ala | Thr | Lys | Asn | |
| | | 35 | | | | | 40 | | | | | 45 | | | | |
| GGA | CAG | GCG | GTG | TGC | CCC | TAC | GAT | CCA | CGT | CAC | AAC | TCC | ACC | TCT | GTG | 192 |
| Gly | Gln | Ala | Val | Cys | Pro | Tyr | Asp | Pro | Arg | His | Asn | Ser | Thr | Ser | Val | |
| 50 | | | | | 55 | | | | | 60 | | | | | | |
| CTG | GCC | GAC | AAC | GAA | CTG | TAT | TCC | GGT | ACC | GTG | GCG | GAT | TTC | AGT | GGC | 240 |
| Leu | Ala | Asp | Asn | Glu | Leu | Tyr | Ser | Gly | Thr | Val | Ala | Asp | Phe | Ser | Gly | |
| 65 | | | | | 70 | | | | | 75 | | | | | 80 | |
| AGC | GAT | CCG | ATT | ATC | TAC | CGG | GAG | CCC | CTG | CAG | ACC | GAG | CAG | TAC | GAT | 288 |
| Ser | Asp | Pro | Ile | Ile | Tyr | Arg | Glu | Pro | Leu | Gln | Thr | Glu | Gln | Tyr | Asp | |
| | | | | 85 | | | | | 90 | | | | | 95 | | |
| AGC | CTA | AGT | CTC | AAC | GCA | CCG | AAC | TTT | GTG | AGC | TCA | TTT | ACG | CAG | GGC | 336 |
| Ser | Leu | Ser | Leu | Asn | Ala | Pro | Asn | Phe | Val | Ser | Ser | Phe | Thr | Gln | Gly | |
| | | | 100 | | | | | 105 | | | | | 110 | | | |
| GAC | TTT | GTC | TAT | TTC | TTC | TTT | CGG | GAA | ACC | GCC | GTT | GAG | TTT | ATC | AAC | 384 |
| Asp | Phe | Val | Tyr | Phe | Phe | Phe | Arg | Glu | Thr | Ala | Val | Glu | Phe | Ile | Asn | |
| | | 115 | | | | | 120 | | | | | 125 | | | | |
| TGT | GGC | AAG | GCG | ATT | TAT | TCG | CGC | GTT | GCC | CGC | GTC | TGC | AAA | TGG | GAC | 432 |
| Cys | Gly | Lys | Ala | Ile | Tyr | Ser | Arg | Val | Ala | Arg | Val | Cys | Lys | Trp | Asp | |
| | | 130 | | | | | 135 | | | | | 140 | | | | |
| AAA | GGT | GGC | CCG | CAT | CGA | TTC | CGC | AAC | CGC | TGG | ACA | TCC | TTC | CTC | AAG | 480 |
| Lys | Gly | Gly | Pro | His | Arg | Phe | Arg | Asn | Arg | Trp | Thr | Ser | Phe | Leu | Lys | |
| 145 | | | | | 150 | | | | | 155 | | | | | 160 | |
| TCC | CGC | CTC | AAC | TGC | TCC | ATT | CCC | GGC | GAT | TAT | CCT | TTC | TAC | TTT | AAT | 528 |
| Ser | Arg | Leu | Asn | Cys | Ser | Ile | Pro | Gly | Asp | Tyr | Pro | Phe | Tyr | Phe | Asn | |
| | | | | 165 | | | | | 170 | | | | | 175 | | |
| GAA | ATC | CAA | TCT | GCC | AGC | AAT | CTG | GTG | GAG | GGA | CAG | TAT | GGC | TCG | ATG | 576 |
| Glu | Ile | Gln | Ser | Ala | Ser | Asn | Leu | Val | Glu | Gly | Gln | Tyr | Gly | Ser | Met | |
| | | | 180 | | | | | 185 | | | | | 190 | | | |
| AGC | TCG | AAA | CTG | ATC | TAC | GGA | GTC | TTC | AAC | ACG | CCG | AGC | AAC | TCA | ATT | 624 |
| Ser | Ser | Lys | Leu | Ile | Tyr | Gly | Val | Phe | Asn | Thr | Pro | Ser | Asn | Ser | Ile | |
| | | 195 | | | | | 200 | | | | | 205 | | | | |
| CCC | GGC | TCA | GCG | GTT | TGT | GCC | TTT | GCC | CTC | CAG | GAC | ATT | GCC | GAT | ACG | 672 |
| Pro | Gly | Ser | Ala | Val | Cys | Ala | Phe | Ala | Leu | Gln | Asp | Ile | Ala | Asp | Thr | |
| | 210 | | | | | 215 | | | | | 220 | | | | | |
| TTT | GAG | GGT | CAG | TTC | AAG | GAG | CAG | ACT | GGC | ATC | AAC | TCC | AAC | TGG | CTG | 720 |
| Phe | Glu | Gly | Gln | Phe | Lys | Glu | Gln | Thr | Gly | Ile | Asn | Ser | Asn | Trp | Leu | |
| 225 | | | | 230 | | | | | 235 | | | | | | 240 | |
| CCA | GTG | AAC | AAC | GCC | AAG | GTA | CCC | GAT | CCT | CGA | CCC | GGT | TCC | TGT | CAC | 768 |
| Pro | Val | Asn | Asn | Ala | Lys | Val | Pro | Asp | Pro | Arg | Pro | Gly | Ser | Cys | His | |
| | | | | 245 | | | | | 250 | | | | | 255 | | |
| AAC | GAT | TCG | AGA | GCG | CTT | CCG | GAT | CCC | ACA | CTG | AAC | TTC | ATC | AAA | ACA | 816 |
| Asn | Asp | Ser | Arg | Ala | Leu | Pro | Asp | Pro | Thr | Leu | Asn | Phe | Ile | Lys | Thr | |
| | | | 260 | | | | | 265 | | | | | 270 | | | |
| CAT | TCG | CTA | ATG | GAC | GAG | AAT | GTG | CCG | GCA | TTT | TTC | AGT | CAA | CCG | ATT | 864 |

|     |     |     |     |     |     |     |     |     |     |     |     |     |     |     |      |
| --- | --- | --- | --- | --- | --- | --- | --- | --- | --- | --- | --- | --- | --- | --- | ---- |
| His | Ser | Leu | Met | Asp | Glu | Asn | Val | Pro | Ala | Phe | Phe | Ser | Gln | Pro | Ile  |
|     |     | 275 |     |     |     | 280 |     |     |     |     |     | 285 |     |     |      |
| TTG | GTC | CGG | ACG | AGC | ACA | ATA | TAC | CGC | TTC | ACT | CAA | ATC | GCC | GTA | GAT  | 912 |
| Leu | Val | Arg | Thr | Ser | Thr | Ile | Tyr | Arg | Phe | Thr | Gln | Ile | Ala | Val | Asp  |
|     | 290 |     |     |     |     | 295 |     |     |     |     | 300 |     |     |     |      |
| GCG | CAG | ATT | AAA | ACT | CCT | GGC | GGC | AAG | ACA | TAT | GAT | GTT | ATC | TTT | GTG  | 960 |
| Ala | Gln | Ile | Lys | Thr | Pro | Gly | Gly | Lys | Thr | Tyr | Asp | Val | Ile | Phe | Val  |
| 305 |     |     |     |     | 310 |     |     |     |     | 315 |     |     |     |     | 320  |
| GGC | ACA | GAT | CAT | GGA | AAG | ATT | ATT | AAG | TCA | GTG | AAT | GCT | GAA | TCT | GCC  | 1008 |
| Gly | Thr | Asp | His | Gly | Lys | Ile | Ile | Lys | Ser | Val | Asn | Ala | Glu | Ser | Ala  |
|     |     |     |     | 325 |     |     |     |     | 330 |     |     |     |     | 335 |      |
| GAT | TCA | GCG | GAT | AAA | GTC | ACC | TCC | GTA | GTC | ATC | GAG | GAG | ATC | GAT | GTC  | 1056 |
| Asp | Ser | Ala | Asp | Lys | Val | Thr | Ser | Val | Val | Ile | Glu | Glu | Ile | Asp | Val  |
|     |     |     | 340 |     |     |     |     | 345 |     |     |     |     | 350 |     |      |
| CTG | ACC | AAG | AGT | GAA | CCC | ATA | CGC | AAT | CTG | GAG | ATA | GTC | AGA | ACC | ATG  | 1104 |
| Leu | Thr | Lys | Ser | Glu | Pro | Ile | Arg | Asn | Leu | Glu | Ile | Val | Arg | Thr | Met  |
|     |     | 355 |     |     |     |     | 360 |     |     |     |     | 365 |     |     |      |
| CAG | TAC | GAT | CAA | CCC | AAA | GAT | GGC | AGC | TAC | GAC | GAT | GGT | AAA | TTA | ATC  | 1152 |
| Gln | Tyr | Asp | Gln | Pro | Lys | Asp | Gly | Ser | Tyr | Asp | Asp | Gly | Lys | Leu | Ile  |
|     || 370 |     |     |     |     | 375 |     |     |     |     | 380 |     |     |     |      |
| ATT | GTG | ACG | GAC | AGT | CAG | GTG | GTA | GCC | ATA | CAA | TTG | CAT | CGT | TGT | CAC  | 1200 |
| Ile | Val | Thr | Asp | Ser | Gln | Val | Val | Ala | Ile | Gln | Leu | His | Arg | Cys | His  |
| 385 |     |     |     |     | 390 |     |     |     |     | 395 |     |     |     |     | 400  |
| AAT | GAC | AAA | ATC | ACC | AGC | TGC | AGC | GAG | TGC | GTC | GCA | TTG | CAG | GAT | CCG  | 1248 |
| Asn | Asp | Lys | Ile | Thr | Ser | Cys | Ser | Glu | Cys | Val | Ala | Leu | Gln | Asp | Pro  |
|     |     |     |     | 405 |     |     |     |     | 410 |     |     |     |     | 415 |      |
| TAC | TGC | GCC | TGG | GAC | AAA | ATC | GCT | GGC | AAG | TGC | CGT | TCC | CAC | GGC | GCT  | 1296 |
| Tyr | Cys | Ala | Trp | Asp | Lys | Ile | Ala | Gly | Lys | Cys | Arg | Ser | His | Gly | Ala  |
|     |     |     | 420 |     |     |     |     | 425 |     |     |     |     | 430 |     |      |
| CCC | CGA | TGG | CTA | GAG | GAG | AAC | TAT | TTC | TAC | CAG | AAT | GTG | GCC | ACT | GGC  | 1344 |
| Pro | Arg | Trp | Leu | Glu | Glu | Asn | Tyr | Phe | Tyr | Gln | Asn | Val | Ala | Thr | Gly  |
|     |     | 435 |     |     |     |     | 440 |     |     |     |     | 445 |     |     |      |
| CAG | CAT | GCG | GCC | TGC | CCC | TCA | GGC | AAA | ATC | AAT | TCA | AAG | GAT | GCC | AAC  | 1392 |
| Gln | His | Ala | Ala | Cys | Pro | Ser | Gly | Lys | Ile | Asn | Ser | Lys | Asp | Ala | Asn  |
|     |     | 450 |     |     |     |     | 455 |     |     |     |     | 460 |     |     |      |
| GCT | GGG | GAG | CAG | AAG | GGC | TTC | CGC | AAC | GAC | ATG | GAC | TTA | TTG | GAT | TCG  | 1440 |
| Ala | Gly | Glu | Gln | Lys | Gly | Phe | Arg | Asn | Asp | Met | Asp | Leu | Leu | Asp | Ser  |
| 465 |     |     |     |     | 470 |     |     |     |     | 475 |     |     |     |     | 480  |
| CGA | CGC | CAG | AGC | AAG | GAT | CAG | GAA | ATA | ATC | GAC | AAT | ATT | GAT | AAG | AAC  | 1488 |
| Arg | Arg | Gln | Ser | Lys | Asp | Gln | Glu | Ile | Ile | Asp | Asn | Ile | Asp | Lys | Asn  |
|     |     |     |     | 485 |     |     |     |     | 490 |     |     |     |     | 495 |      |
| TTT | GAA | GAT | ATA | ATC | AAC | GCC | CAG | TAC | ACT | GTG | GAG | ACC | CTC | GTG | ATG  | 1536 |
| Phe | Glu | Asp | Ile | Ile | Asn | Ala | Gln | Tyr | Thr | Val | Glu | Thr | Leu | Val | Met  |
|     |     |     | 500 |     |     |     |     | 505 |     |     |     |     | 510 |     |      |
| GCC | GTT | CTG | GCC | GGT | TCG | ATC | TTT | TCG | CTG | CTG | GTC | GGC | TTC | TTT | ACA  | 1584 |
| Ala | Val | Leu | Ala | Gly | Ser | Ile | Phe | Ser | Leu | Leu | Val | Gly | Phe | Phe | Thr  |
|     |     | 515 |     |     |     |     | 520 |     |     |     |     | 525 |     |     |      |
| GGC | TAC | TTC | TGC | GGT | CGC | CGT | TGT | CAC | AAG | GAC | GAG | GAT | GAT | AAT | CTG  | 1632 |
| Gly | Tyr | Phe | Cys | Gly | Arg | Arg | Cys | His | Lys | Asp | Glu | Asp | Asp | Asn | Leu  |
|     | 530 |     |     |     |     | 535 |     |     |     |     | 540 |     |     |     |      |
| CCG | TAT | CCG | GAT | ACG | GAG | TAC | GAG | TAC | TTC | GAG | CAG | CGA | CAG | AAT | GTC  | 1680 |
| Pro | Tyr | Pro | Asp | Thr | Glu | Tyr | Glu | Tyr | Phe | Glu | Gln | Arg | Gln | Asn | Val  |
| 545 |     |     |     |     | 550 |     |     |     |     | 555 |     |     |     |     | 560  |
| AAT | AGC | TTC | CCC | TCG | TCC | TGT | CGC | ATC | CAG | CAG | GAG | CCC | AAG | CTG | CTG  | 1728 |
| Asn | Ser | Phe | Pro | Ser | Ser | Cys | Arg | Ile | Gln | Gln | Glu | Pro | Lys | Leu | Leu  |
|     |     |     |     | 565 |     |     |     |     | 570 |     |     |     |     | 575 |      |
| CCC | CAA | GTG | GAG | GAG | GTG | ACG | TAT | GCG | GAC | GCA | GTG | CTC | CTG | CCA | CAG  | 1776 |
| Pro | Gln | Val | Glu | Glu | Val | Thr | Tyr | Ala | Asp | Ala | Val | Leu | Leu | Pro | Gln  |
|     |     |     | 580 |     |     |     |     | 585 |     |     |     |     | 590 |     |      |
| CCT | CCG | CCG | CCC | AAT | AAG | ATG | CAC | TCG | CCG | AAG | AAC | ACG | CTG | CGT | AAG  | 1824 |

| | | | | | | | | | | | | | | |
|---|---|---|---|---|---|---|---|---|---|---|---|---|---|---|
|Pro|Pro|Pro 595|Pro|Asn|Lys|Met|His 600|Ser|Pro|Lys|Asn|Thr 605|Leu|Arg Lys|

| | | | | | | | | | | | | | | | |
|---|---|---|---|---|---|---|---|---|---|---|---|---|---|---|---|
|CCC|CCG|ATG|CAC|CAG|ATG|CAC|CAG|GGT|CCC|AAC|TCG|GAG|ACC|CTC|TTC|
|Pro|Pro 610|Met|His|Gln|Met|His 615|Gln|Gly|Pro|Asn|Ser 620|Glu|Thr|Leu|Phe|

1872

| | | | | | | | | | | | | | | | |
|---|---|---|---|---|---|---|---|---|---|---|---|---|---|---|---|
|CAG|TTC|CAC|GTG|ACG|GCT|ACA|ACA|CCC|AGC|AGT|CGT|ATC|GTG|GTC|GCG|
|Gln 625|Phe|His|Val|Thr|Ala 630|Thr|Thr|Pro|Ser|Ser 635|Arg|Ile|Val|Val|Ala 640|

1920

| | | | | | | | | | |
|---|---|---|---|---|---|---|---|---|---|
|ACA|ACT|TCG|GAA|CAC|TGC|GTT|CCC|ACC|AGG|TGATGGCGA CAATTACAGG|
|Thr|Thr|Ser|Glu|His 645|Cys|Val|Pro|Thr|Arg 650| |

1970

```
CGCGGCGATG  GCTTTTCCAC  CACCCGCAGC  GTCAAGAAGG  TTTACCTTTG  AGACGGGAGT      2030
GGGGCGGCTG  AAACCAGTCA  GGGACTAATT  ACCCAAAATA  TGGCTGTAAA  CAACACAAAC      2090
ACACGTAACA  GAAGTCTTGG  TCGCGCAAGA  AGACAGCCGC  CCCGTCATGG  CATTGTAACT      2150
CAACACCGCT  CGAATAGCCC  CCAGCAGCAG  CAGCAGCAGT  CGCAGCAGCC  GCACTCCAGT      2210
TCGGGCTCCT  CGCCCGTAAT  GTCAACAGC   AGCAGCAGTC  CGGCTCCGCC  CTCCAGCAGT      2270
CCCAGTCCGC  AGGAGAGCCC  CAAGAACTGC  AGCTACATCT  ACCGTGATTG  ATTGATATGC      2330
AACACCAAAT  CGATGCCACT  CATCCAGGCC  CAGTCCACGC  ACGCCCAGCC  ACACTCACAC      2390
CCGCACCCGC  ACCCGCTTCC  GCCACCCGGT  CCGACCACGC  CCCAGCACA   GCCACGCGCC      2450
AGAAGTCCAA  TGATCGGCAG  GACATATGCC  AAGTCCATGC  CCGTGACACC  AGTTCAACCG      2510
CAATCGCCGC  TGGCTGAGAC  GCCCTCCTAT  GAGCTCTACG  AACGCCACTC  GGATGCGGCC      2570
ACCTTCCACT  TTGGGGATGA  GGACGATGAC  GATGATGATG  AGCACGACCA  GGAGGACACC      2630
TCATCGCTGG  CCATGATCAC  ACCGCCGCCG  CCCTACGACA  CTCCGCATCT  GATTGCATCG      2690
CCACCGCTGC  CGCCGCCTCG  TAGATTTCGC  TTTGGCAACA  GGGAGCTGTT  CAGCATGAGT      2750
CCAGCCGGAG  GTGGAACCAC  GCCCACCGCC  TCGGCAGGCC  AACGCGGCAG  CAGCGCCATC      2810
ACGCCCACAA  AGTTGAGTGC  GGCGGCAGCG  GCCATGTTTG  CCGCACCCCA  AATGGCCACC      2870
CAACTCAACC  GGAAGTGGGC  TCATTTGCAA  AGGAAGCGGC  GCAGGCGCAA  CAGCAGCTCC      2930
GGCGATTCTA  AGGAGCTCGA  CAAACTGGTC  CTGCAATCGG  TCGACTGGGA  TGAGAATGAG      2990
ATGTACTAGA  ACGCAAACCA  ACAATGAGAT  AGCAGAAACA  CTTTGATTCG  GAATTTATAC      3050
ACCTTTGCAT  ATTTTGAATA  TGACTTCAAT  TTTAAAATGC  GTAATTATGT  TCTTATTTTT      3110
TAAAGAACGC  TTTAGAGAAG  TTTTCTGCTA  CCTTAAATAG  TACACACAAC  TCATATCTAA      3170
CGTGGCGCTG  CGATATAGGA  ATAACCACTC  CCCCTTCCCT  TAAACTTAAA  GTAGCAATCG      3230
AAAAGATCAT  TCATTAGCGA  CAGAAACTGG  ATGGGGATTT  ACTTACACAC  AAAAAGCCAG      3290
AGAAGTTATA  CACGAAGTTT  ATAGTTATAT  AGCCTTTATA  CATACTCCCC  GATCTGCTAA      3350
GTATACACAA  GCAAGCATAA  CATAACATAC  GTATATATGA  CTCTATATAT  ACCAATAGAT      3410
TTCATAGACG  ATTCACATGG  ATCGGCTACG  CTAAATTAGA  GCTGCAAAAT  GATATTGTTA      3470
ATTACGATTA  GAGAAAAAAA  AAAAGGAATT  CGATATCAAG  CKTATCGATA  CCNTCGACCT      3530
CGNNNNGGG   GCCCGGTACC  CAATTCGCCC                                           3560
```

( 2 ) INFORMATION FOR SEQ ID NO:60:

( i ) SEQUENCE CHARACTERISTICS:
        ( A ) LENGTH: 650 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Glu  Asp  Asp  Cys  Gln  Asn  Tyr  Ile  Arg  Ile  Met  Val  Val  Pro  Ser  Pro
 1              5                     10                       15
Gly  Arg  Leu  Phe  Val  Cys  Gly  Thr  Asn  Ser  Phe  Arg  Pro  Met  Cys  Asn
               20                     25                       30
Thr  Tyr  Ile  Ile  Ser  Asp  Ser  Asn  Tyr  Thr  Leu  Glu  Ala  Thr  Lys  Asn
               35                     40                       45
Gly  Gln  Ala  Val  Cys  Pro  Tyr  Asp  Pro  Arg  His  Asn  Ser  Thr  Ser  Val
          50                     55                  60
Leu  Ala  Asp  Asn  Glu  Leu  Tyr  Ser  Gly  Thr  Val  Ala  Asp  Phe  Ser  Gly
 65                     70                     75                          80
Ser  Asp  Pro  Ile  Ile  Tyr  Arg  Glu  Pro  Leu  Gln  Thr  Glu  Gln  Tyr  Asp
               85                     90                       95
Ser  Leu  Ser  Leu  Asn  Ala  Pro  Asn  Phe  Val  Ser  Ser  Phe  Thr  Gln  Gly
               100                    105                      110
Asp  Phe  Val  Tyr  Phe  Phe  Phe  Arg  Glu  Thr  Ala  Val  Glu  Phe  Ile  Asn
          115                    120                      125
Cys  Gly  Lys  Ala  Ile  Tyr  Ser  Arg  Val  Ala  Arg  Val  Cys  Lys  Trp  Asp
          130                    135                      140
Lys  Gly  Gly  Pro  His  Arg  Phe  Arg  Asn  Arg  Trp  Thr  Ser  Phe  Leu  Lys
145                      150                    155                       160
Ser  Arg  Leu  Asn  Cys  Ser  Ile  Pro  Gly  Asp  Tyr  Pro  Phe  Tyr  Phe  Asn
                    165                    170                      175
Glu  Ile  Gln  Ser  Ala  Ser  Asn  Leu  Val  Glu  Gly  Gln  Tyr  Gly  Ser  Met
               180                    185                      190
Ser  Ser  Lys  Leu  Ile  Tyr  Gly  Val  Phe  Asn  Thr  Pro  Ser  Asn  Ser  Ile
          195                    200                      205
Pro  Gly  Ser  Ala  Val  Cys  Ala  Phe  Ala  Leu  Gln  Asp  Ile  Ala  Asp  Thr
     210                    215                      220
Phe  Glu  Gly  Gln  Phe  Lys  Glu  Gln  Thr  Gly  Ile  Asn  Ser  Asn  Trp  Leu
225                      230                    235                       240
Pro  Val  Asn  Asn  Ala  Lys  Val  Pro  Asp  Pro  Arg  Pro  Gly  Ser  Cys  His
                    245                    250                      255
Asn  Asp  Ser  Arg  Ala  Leu  Pro  Asp  Pro  Thr  Leu  Asn  Phe  Ile  Lys  Thr
                    260                    265                      270
His  Ser  Leu  Met  Asp  Glu  Asn  Val  Pro  Ala  Phe  Phe  Ser  Gln  Pro  Ile
          275                    280                      285
Leu  Val  Arg  Thr  Ser  Thr  Ile  Tyr  Arg  Phe  Thr  Gln  Ile  Ala  Val  Asp
     290                    295                      300
Ala  Gln  Ile  Lys  Thr  Pro  Gly  Gly  Lys  Thr  Tyr  Asp  Val  Ile  Phe  Val
305                      310                    315                       320
Gly  Thr  Asp  His  Gly  Lys  Ile  Ile  Lys  Ser  Val  Asn  Ala  Glu  Ser  Ala
               325                    330                      335
Asp  Ser  Ala  Asp  Lys  Val  Thr  Ser  Val  Ile  Glu  Glu  Ile  Asp  Val
               340                    345                      350
Leu  Thr  Lys  Ser  Glu  Pro  Ile  Arg  Asn  Leu  Glu  Ile  Val  Arg  Thr  Met
          355                    360                      365
Gln  Tyr  Asp  Gln  Pro  Lys  Asp  Gly  Ser  Tyr  Asp  Asp  Gly  Lys  Leu  Ile
     370                    375                      380
Ile  Val  Thr  Asp  Ser  Gln  Val  Val  Ala  Ile  Gln  Leu  His  Arg  Cys  His
385                      390                    395                       400
Asn  Asp  Lys  Ile  Thr  Ser  Cys  Ser  Glu  Cys  Val  Ala  Leu  Gln  Asp  Pro
                    405                    410                      415
Tyr  Cys  Ala  Trp  Asp  Lys  Ile  Ala  Gly  Lys  Cys  Arg  Ser  His  Gly  Ala
```

|     |     |     |     |     | 420 |     |     |     |     | 425 |     |     |     |     | 430 |     |
| --- | --- | --- | --- | --- | --- | --- | --- | --- | --- | --- | --- | --- | --- | --- | --- | --- |

Pro Arg Trp Leu Glu Glu Asn Tyr Phe Tyr Gln Asn Val Ala Thr Gly
        435                       440                       445

Gln His Ala Ala Cys Pro Ser Gly Lys Ile Asn Ser Lys Asp Ala Asn
     450                       455                    460

Ala Gly Glu Gln Lys Gly Phe Arg Asn Asp Met Asp Leu Leu Asp Ser
465                      470                  475                480

Arg Arg Gln Ser Lys Asp Gln Glu Ile Ile Asp Asn Ile Asp Lys Asn
             485                    490                495

Phe Glu Asp Ile Ile Asn Ala Gln Tyr Thr Val Glu Thr Leu Val Met
          500                  505             510

Ala Val Leu Ala Gly Ser Ile Phe Ser Leu Leu Val Gly Phe Phe Thr
       515                520               525

Gly Tyr Phe Cys Gly Arg Arg Cys His Lys Asp Glu Asp Asp Asn Leu
     530                       535               540

Pro Tyr Pro Asp Thr Glu Tyr Glu Tyr Phe Glu Gln Arg Gln Asn Val
545                      550                555              560

Asn Ser Phe Pro Ser Ser Cys Arg Ile Gln Gln Glu Pro Lys Leu Leu
             565                570              575

Pro Gln Val Glu Glu Val Thr Tyr Ala Asp Ala Val Leu Leu Pro Gln
            580                  585            590

Pro Pro Pro Pro Asn Lys Met His Ser Pro Lys Asn Thr Leu Arg Lys
     595                     600               605

Pro Pro Met His Gln Met His Gln Gly Pro Asn Ser Glu Thr Leu Phe
       610                615              620

Gln Phe His Val Thr Ala Thr Thr Pro Ser Ser Arg Ile Val Val Ala
625                     630                635              640

Thr Thr Ser Glu His Cys Val Pro Thr Arg
            645              650

( 2 ) INFORMATION FOR SEQ ID NO:61:

( i ) SEQUENCE CHARACTERISTICS:
        ( A ) LENGTH: 2670 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 268..2439

( x i ) SEQUENCE DESCRIPTION: SEQ ID NO:61:

GAAAATCGAA CWCCGAATTG AATGAACWGC AAAACGCCAA TTAGATAGTT GCAAGCCTAA    60

TGCATTTCAG AKATTTNMMC GATGCGAAAC AAGTTCCGCC ACGAAAGTGA ACAGTGGTAA   120

AATGCCCAAG AATCTCGAGC GGAAACACCA AACACAAAAG AACAAGCAAC CGCCTCTCAC   180

TCGCTCTTGC ACTTTAATCC AATTGAGGTT GGTGGGGTCG CATTCGCCCC CCGGTCGACC   240

ACCCCTCTCG CTCGCACCGC CCTCGCA ATG TCT CTT CTA CAG CTA TCG CCG CTC   294
                                              Met Ser Leu Leu Gln Leu Ser Pro Leu
                                                1                    5

CTC GCA CTC CTG CTA CTC CTC TGC AGT AGT GTG AGC GAG ACG GCT GCG   342
Leu Ala Leu Leu Leu Leu Leu Cys Ser Ser Val Ser Glu Thr Ala Ala
 10                       15                  20                  25

GAC TAC GAG AAC ACC TGG AAC TTC TAC TAC GAG CGT CCC TGT TGC ACT   390
Asp Tyr Glu Asn Thr Trp Asn Phe Tyr Tyr Glu Arg Pro Cys Cys Thr

```
                           30                           35                           40
GGA AAC GAT CAG GGG AAC AAC AAT TAC GGA AAA CAC GGC GCA GAT CAT         438
Gly Asn Asp Gln Gly Asn Asn Asn Tyr Gly Lys His Gly Ala Asp His
             45                          50                           55

GTG CGG GAG TTC AAC TGC GGC AAG CTG TAC TAT CGT ACA TTC CAT ATG         486
Val Arg Glu Phe Asn Cys Gly Lys Leu Tyr Tyr Arg Thr Phe His Met
         60                          65                       70

AAC GAA GAT CGA GAT ACG CTC TAT GTG GGA GCC ATG GAT CGC GTA TTC         534
Asn Glu Asp Arg Asp Thr Leu Tyr Val Gly Ala Met Asp Arg Val Phe
     75                           80                   85

CGT GTG AAC CTG CAG AAT ATC TCC TCA TCC AAT TGT AAT CGG GAT GCG         582
Arg Val Asn Leu Gln Asn Ile Ser Ser Ser Asn Cys Asn Arg Asp Ala
 90                           95                      100                 105

ATC AAC TTG GAG CCA ACA CGG GAT GAT GTG GTT AGC TGC GTC TCC AAA         630
Ile Asn Leu Glu Pro Thr Arg Asp Asp Val Val Ser Cys Val Ser Lys
                     110                      115                      120

GGC AAA AGT CAG ATC TTC GAC TGC AAG AAC CAT GTG CGT GTC ATC CAG         678
Gly Lys Ser Gln Ile Phe Asp Cys Lys Asn His Val Arg Val Ile Gln
             125                      130                      135

TCA ATG GAC CAG GGG GAT AGG CTC TAT GTA TGC GGC ACC AAC GCC CAC         726
Ser Met Asp Gln Gly Asp Arg Leu Tyr Val Cys Gly Thr Asn Ala His
         140                      145                      150

AAT CCC AAG GAT TAT GTT ATC TAT GCG AAT CTA ACC CAC CTG CCG CGC         774
Asn Pro Lys Asp Tyr Val Ile Tyr Ala Asn Leu Thr His Leu Pro Arg
     155                      160                      165

TCG GAA TAT GTG ATT GGC GTG GGT CTG GGC ATT GCC AAG TGC CCC TAC         822
Ser Glu Tyr Val Ile Gly Val Gly Leu Gly Ile Ala Lys Cys Pro Tyr
170                      175                      180                      185

GAT CCC CTC GAC AAC TCA ACT GCG ATT TAT GTG GAG AAT GGC AAT CCG         870
Asp Pro Leu Asp Asn Ser Thr Ala Ile Tyr Val Glu Asn Gly Asn Pro
                     190                      195                      200

GGT GGT CTG CCC GGT TTG TAC TCC GGC ACC AAT GCG GAG TTC ACC AAG         918
Gly Gly Leu Pro Gly Leu Tyr Ser Gly Thr Asn Ala Glu Phe Thr Lys
             205                      210                      215

GCG GAT ACG GTT ATT TTC CGC ACT GAT CTG TAT AAT ACT TCG GCT AAA         966
Ala Asp Thr Val Ile Phe Arg Thr Asp Leu Tyr Asn Thr Ser Ala Lys
         220                      225                      230

CGT TTG GAA TAT AAA TTC AAG AGG ACT CTG AAA TAC GAC TCC AAG TGG        1014
Arg Leu Glu Tyr Lys Phe Lys Arg Thr Leu Lys Tyr Asp Ser Lys Trp
     235                      240                      245

TTG GAC AAA CCA AAC TTT GTC GGC TCC TTT GAT ATT GGG GAG TAC GTG    1062
Leu Asp Lys Pro Asn Phe Val Gly Ser Phe Asp Ile Gly Glu Tyr Val
250                      255                      260                      265

TAT TTC TTT TTC CGT GAA ACC GCC GTG GAA TAC ATC AAC TGC GGC AAG        1110
Tyr Phe Phe Phe Arg Glu Thr Ala Val Glu Tyr Ile Asn Cys Gly Lys
                     270                      275                      280

GCT GTC TAT TCG CGC ATC GCA CGG GTG TGC AAG AAG GAT GTG GGT GGA        1158
Ala Val Tyr Ser Arg Ile Ala Arg Val Cys Lys Lys Asp Val Gly Gly
             285                      290                      295

AAG AAT CTG CTG GCC CAC AAC TGG GCC ACC TAC CTG AAG GCC AGA CTC        1206
Lys Asn Leu Leu Ala His Asn Trp Ala Thr Tyr Leu Lys Ala Arg Leu
         300                      305                      310

AAC TGC AGC ATC TCC GGC GAA TTT CCG TTC TAT TTC AAC GAG ATC CAA        1254
Asn Cys Ser Ile Ser Gly Glu Phe Pro Phe Tyr Phe Asn Glu Ile Gln
     315                      320                      325

TCG GTC TAC CAG CTG CCC TCC GAT AAG AGT CGA TTC TTC GCC ACA TTC        1302
Ser Val Tyr Gln Leu Pro Ser Asp Lys Ser Arg Phe Phe Ala Thr Phe
330                      335                      340                      345

ACG ACG AGC ACT AAT GGC CTG ATT GGA TCT GCC GTA TGC AGT TTC CAC        1350
Thr Thr Ser Thr Asn Gly Leu Ile Gly Ser Ala Val Cys Ser Phe His
```

-continued

|  |  |  |  |  |  |  |  |  |  |  |  |  |  |  |  |  |
|---|---|---|---|---|---|---|---|---|---|---|---|---|---|---|---|---|
|  |  |  |  | 350 |  |  |  |  | 355 |  |  |  |  | 360 |  |  |
| ATT | AAC | GAG | ATT | CAG | GCT | GCC | TTC | AAT | GGC | AAA | TTC | AAG | GAG | CAA | TCT | 1398 |
| Ile | Asn | Glu | Ile | Gln | Ala | Ala | Phe | Asn | Gly | Lys | Phe | Lys | Glu | Gln | Ser |  |
|  |  |  |  | 365 |  |  |  |  | 370 |  |  |  |  | 375 |  |  |
| TCA | TCG | AAT | TCC | GCA | TGG | CTG | CCG | GTG | CTT | AAC | TCC | CGG | GTG | CCG | GAA | 1446 |
| Ser | Ser | Asn | Ser | Ala | Trp | Leu | Pro | Val | Leu | Asn | Ser | Arg | Val | Pro | Glu |  |
|  |  |  |  | 380 |  |  |  |  | 385 |  |  |  |  | 390 |  |  |
| CCA | CGG | CCG | GGT | ACA | TGT | GTC | AAC | GAT | ACA | TCA | AAC | CTG | CCC | GAT | ACC | 1494 |
| Pro | Arg | Pro | Gly | Thr | Cys | Val | Asn | Asp | Thr | Ser | Asn | Leu | Pro | Asp | Thr |  |
|  |  |  |  | 395 |  |  |  |  | 400 |  |  |  |  | 405 |  |  |
| GTA | CTG | AAT | TTC | ATC | AGA | TCC | CAT | CCA | CTT | ATG | GAC | AAA | GCC | GTA | AAT | 1542 |
| Val | Leu | Asn | Phe | Ile | Arg | Ser | His | Pro | Leu | Met | Asp | Lys | Ala | Val | Asn |  |
|  | 410 |  |  |  |  | 415 |  |  |  |  | 420 |  |  |  | 425 |  |
| CAC | GAG | CAC | AAC | AAT | CCA | GTC | TAT | TAT | AAA | AGG | GAT | TTG | GTC | TTC | ACC | 1590 |
| His | Glu | His | Asn | Asn | Pro | Val | Tyr | Tyr | Lys | Arg | Asp | Leu | Val | Phe | Thr |  |
|  |  |  |  |  | 430 |  |  |  |  | 435 |  |  |  |  | 440 |  |
| AAG | CTC | GTC | GTT | GAC | AAA | ATT | CGC | ATT | GAC | ATC | CTC | AAC | CAG | GAA | TAC | 1638 |
| Lys | Leu | Val | Val | Asp | Lys | Ile | Arg | Ile | Asp | Ile | Leu | Asn | Gln | Glu | Tyr |  |
|  |  |  |  | 445 |  |  |  |  | 450 |  |  |  |  | 455 |  |  |
| ATT | GTG | TAC | TAT | GTG | GGC | ACC | AAT | CTG | GGT | CGC | ATT | TAC | AAA | ATC | GTG | 1686 |
| Ile | Val | Tyr | Tyr | Val | Gly | Thr | Asn | Leu | Gly | Arg | Ile | Tyr | Lys | Ile | Val |  |
|  |  |  |  | 460 |  |  |  |  | 465 |  |  |  |  | 470 |  |  |
| CAG | TAC | TAC | CGT | AAC | GGA | GAG | TCG | CTG | TCC | AAG | CTT | CTG | GAT | ATC | TTC | 1734 |
| Gln | Tyr | Tyr | Arg | Asn | Gly | Glu | Ser | Leu | Ser | Lys | Leu | Leu | Asp | Ile | Phe |  |
|  |  | 475 |  |  |  |  | 480 |  |  |  |  | 485 |  |  |  |  |
| GAG | GTG | GCT | CCA | AAC | GAG | GCC | ATC | CAA | GTG | ATG | GAA | ATC | AGC | CAG | ACA | 1782 |
| Glu | Val | Ala | Pro | Asn | Glu | Ala | Ile | Gln | Val | Met | Glu | Ile | Ser | Gln | Thr |  |
| 490 |  |  |  |  | 495 |  |  |  |  | 500 |  |  |  |  | 505 |  |
| CGT | AAG | AGC | CTC | TAC | ATT | GGC | ACC | GAT | CAT | CGC | ATC | AAG | CAA | ATC | GAC | 1830 |
| Arg | Lys | Ser | Leu | Tyr | Ile | Gly | Thr | Asp | His | Arg | Ile | Lys | Gln | Ile | Asp |  |
|  |  |  |  | 510 |  |  |  |  | 515 |  |  |  |  | 520 |  |  |
| CTG | GCC | ATG | TGC | AAT | CGC | CGT | TAC | GAC | AAC | TGC | TTC | CGC | TGC | GTC | CGT | 1878 |
| Leu | Ala | Met | Cys | Asn | Arg | Arg | Tyr | Asp | Asn | Cys | Phe | Arg | Cys | Val | Arg |  |
|  |  |  | 525 |  |  |  |  | 530 |  |  |  |  | 535 |  |  |  |
| GAT | CCC | TAC | TGC | GGC | TGG | GAT | AAG | GAG | GCC | AAT | ACG | TGC | CGA | CCG | TAC | 1926 |
| Asp | Pro | Tyr | Cys | Gly | Trp | Asp | Lys | Glu | Ala | Asn | Thr | Cys | Arg | Pro | Tyr |  |
|  |  |  | 540 |  |  |  |  | 545 |  |  |  |  | 550 |  |  |  |
| GAG | CTG | GAT | TTA | CTG | CAG | GAT | GTG | GCC | AAT | GAA | ACG | AGT | GAC | ATT | TGC | 1974 |
| Glu | Leu | Asp | Leu | Leu | Gln | Asp | Val | Ala | Asn | Glu | Thr | Ser | Asp | Ile | Cys |  |
|  | 555 |  |  |  |  | 560 |  |  |  |  | 565 |  |  |  |  |  |
| GAT | TCG | AGT | GTG | CTG | AAA | AAG | AAG | ATT | GTG | GTG | ACC | TAT | GGC | CAG | AGT | 2022 |
| Asp | Ser | Ser | Val | Leu | Lys | Lys | Lys | Ile | Val | Val | Thr | Tyr | Gly | Gln | Ser |  |
| 570 |  |  |  |  | 575 |  |  |  |  | 580 |  |  |  |  | 585 |  |
| GTA | CAT | CTG | GGC | TGT | TTC | GTC | AAA | ATA | CCC | GAA | GTG | CTG | AAG | AAT | GAG | 2070 |
| Val | His | Leu | Gly | Cys | Phe | Val | Lys | Ile | Pro | Glu | Val | Leu | Lys | Asn | Glu |  |
|  |  |  |  | 590 |  |  |  |  | 595 |  |  |  |  | 600 |  |  |
| CAA | GTG | ACC | TGG | TAT | CAT | CAC | TCC | AAG | GAC | AAG | GGA | CGC | TAC | GAG | ATT | 2118 |
| Gln | Val | Thr | Trp | Tyr | His | His | Ser | Lys | Asp | Lys | Gly | Arg | Tyr | Glu | Ile |  |
|  |  |  | 605 |  |  |  |  | 610 |  |  |  |  | 615 |  |  |  |
| CGT | TAC | TCG | CCG | ACC | AAA | TAC | ATT | GAG | ACC | ACC | GAA | CGT | GGC | CTG | GTT | 2166 |
| Arg | Tyr | Ser | Pro | Thr | Lys | Tyr | Ile | Glu | Thr | Thr | Glu | Arg | Gly | Leu | Val |  |
|  |  | 620 |  |  |  |  | 625 |  |  |  |  | 630 |  |  |  |  |
| GTG | GTT | TCC | GTG | AAC | GAA | GCC | GAT | GGT | GGT | CGG | TAC | GAT | TGC | CAT | TTG | 2214 |
| Val | Val | Ser | Val | Asn | Glu | Ala | Asp | Gly | Gly | Arg | Tyr | Asp | Cys | His | Leu |  |
|  |  | 635 |  |  |  |  | 640 |  |  |  |  | 645 |  |  |  |  |
| GGC | GGC | TCG | CTT | TTG | TGC | AGC | TAC | AAC | ATT | ACA | GTG | GAT | GCC | CAC | AGA | 2262 |
| Gly | Gly | Ser | Leu | Leu | Cys | Ser | Tyr | Asn | Ile | Thr | Val | Asp | Ala | His | Arg |  |
| 650 |  |  |  |  | 655 |  |  |  |  | 660 |  |  |  |  | 665 |  |
| TGC | ACT | CCG | CCG | AAC | AAG | AGT | AAT | GAC | TAT | CAG | AAA | ATC | TAC | TCG | GAC | 2310 |
| Cys | Thr | Pro | Pro | Asn | Lys | Ser | Asn | Asp | Tyr | Gln | Lys | Ile | Tyr | Ser | Asp |  |

|  | 670 |  |  |  |  | 675 |  |  |  |  | 680 |  |  |  |  |
|---|---|---|---|---|---|---|---|---|---|---|---|---|---|---|---|---|
| TGG | TGC | CAC | GAG | TTC | GAG | AAA | TAC | AAA | ACA | GCA | ATG | AAG | TCC | TGG | GAA | 2358 |
| Trp | Cys | His | Glu | Phe | Glu | Lys | Tyr | Lys | Thr | Ala | Met | Lys | Ser | Trp | Glu |  |
|  |  | 685 |  |  |  |  | 690 |  |  |  |  | 695 |  |  |  |  |
| AAG | AAG | CAA | GGC | CAA | TGC | TCG | ACA | CGG | CAG | AAC | TTC | AGC | TGC | AAT | CAG | 2406 |
| Lys | Lys | Gln | Gly | Gln | Cys | Ser | Thr | Arg | Gln | Asn | Phe | Ser | Cys | Asn | Gln |  |
|  |  | 700 |  |  |  |  | 705 |  |  |  |  | 710 |  |  |  |  |
| CAT | CCG | AAT | GAG | ATT | TTC | CGT | AAG | CCC | AAT | GTC | TGATATCACG | AAGAGAGTAT | | | | 2459 |
| His | Pro | Asn | Glu | Ile | Phe | Arg | Lys | Pro | Asn | Val |  |  |  |  |  |  |
|  |  | 715 |  |  |  |  | 720 |  |  |  |  |  |  |  |  |  |

CGCCCTCAAA ATGCCGTCAT CGTCGTCCAA TCAATTTTAG TTAATCGAAA GCGAAGAGGA 2519

TAATAACAGT GCGGAATAGA AAGCCCAGGA CGAGAAGAAC TCATTATAAT CATTATTATC 2579

AGCGACATCA TCATAGACAT ACTTTCTTCA GCAATGAACA GAAAACTCTT CCTAAAGGAT 2639

TATGCATTTA CCGAAGCATT TACAATGCAT C 2670

( 2 ) INFORMATION FOR SEQ ID NO:62:

( i ) SEQUENCE CHARACTERISTICS:
        ( A ) LENGTH: 724 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

| Met | Ser | Leu | Leu | Gln | Leu | Ser | Pro | Leu | Leu | Ala | Leu | Leu | Leu | Leu | Leu |
|---|---|---|---|---|---|---|---|---|---|---|---|---|---|---|---|
| 1 |  |  |  | 5 |  |  |  |  | 10 |  |  |  |  | 15 |  |
| Cys | Ser | Ser | Val | Ser | Glu | Thr | Ala | Ala | Asp | Tyr | Glu | Asn | Thr | Trp | Asn |
|  |  |  | 20 |  |  |  |  | 25 |  |  |  |  | 30 |  |  |
| Phe | Tyr | Tyr | Glu | Arg | Pro | Cys | Cys | Thr | Gly | Asn | Asp | Gln | Gly | Asn | Asn |
|  |  | 35 |  |  |  |  | 40 |  |  |  |  | 45 |  |  |  |
| Asn | Tyr | Gly | Lys | His | Gly | Ala | Asp | His | Val | Arg | Glu | Phe | Asn | Cys | Gly |
|  | 50 |  |  |  |  | 55 |  |  |  |  | 60 |  |  |  |  |
| Lys | Leu | Tyr | Tyr | Arg | Thr | Phe | His | Met | Asn | Glu | Asp | Arg | Asp | Thr | Leu |
| 65 |  |  |  |  | 70 |  |  |  |  | 75 |  |  |  |  | 80 |
| Tyr | Val | Gly | Ala | Met | Asp | Arg | Val | Phe | Arg | Val | Asn | Leu | Gln | Asn | Ile |
|  |  |  |  | 85 |  |  |  |  | 90 |  |  |  |  | 95 |  |
| Ser | Ser | Ser | Asn | Cys | Asn | Arg | Asp | Ala | Ile | Asn | Leu | Glu | Pro | Thr | Arg |
|  |  |  | 100 |  |  |  |  | 105 |  |  |  |  | 110 |  |  |
| Asp | Asp | Val | Val | Ser | Cys | Val | Ser | Lys | Gly | Lys | Ser | Gln | Ile | Phe | Asp |
|  |  |  | 115 |  |  |  |  | 120 |  |  |  |  | 125 |  |  |
| Cys | Lys | Asn | His | Val | Arg | Val | Ile | Gln | Ser | Met | Asp | Gln | Gly | Asp | Arg |
|  | 130 |  |  |  |  | 135 |  |  |  |  | 140 |  |  |  |  |
| Leu | Tyr | Val | Cys | Gly | Thr | Asn | Ala | His | Asn | Pro | Lys | Asp | Tyr | Val | Ile |
| 145 |  |  |  |  | 150 |  |  |  |  | 155 |  |  |  |  | 160 |
| Tyr | Ala | Asn | Leu | Thr | His | Leu | Pro | Arg | Ser | Glu | Tyr | Val | Ile | Gly | Val |
|  |  |  |  | 165 |  |  |  |  | 170 |  |  |  |  | 175 |  |
| Gly | Leu | Gly | Ile | Ala | Lys | Cys | Pro | Tyr | Asp | Pro | Leu | Asp | Asn | Ser | Thr |
|  |  |  | 180 |  |  |  |  | 185 |  |  |  |  | 190 |  |  |
| Ala | Ile | Tyr | Val | Glu | Asn | Gly | Asn | Pro | Gly | Gly | Leu | Pro | Gly | Leu | Tyr |
|  |  |  | 195 |  |  |  |  | 200 |  |  |  |  | 205 |  |  |
| Ser | Gly | Thr | Asn | Ala | Glu | Phe | Thr | Lys | Ala | Asp | Thr | Val | Ile | Phe | Arg |
|  |  | 210 |  |  |  |  | 215 |  |  |  |  | 220 |  |  |  |
| Thr | Asp | Leu | Tyr | Asn | Thr | Ser | Ala | Lys | Arg | Leu | Glu | Tyr | Lys | Phe | Lys |
| 225 |  |  |  |  | 230 |  |  |  |  | 235 |  |  |  |  | 240 |
| Arg | Thr | Leu | Lys | Tyr | Asp | Ser | Lys | Trp | Leu | Asp | Lys | Pro | Asn | Phe | Val |

-continued

|     |     |     |     | 245 |     |     |     | 250 |     |     |     | 255 |     |
|---|---|---|---|---|---|---|---|---|---|---|---|---|---|
| Gly | Ser | Phe | Asp | Ile | Gly | Glu | Tyr | Val | Tyr | Phe | Phe | Arg | Glu | Thr |
|     |     |     | 260 |     |     |     | 265 |     |     |     | 270 |     |     |
| Ala | Val | Glu | Tyr | Ile | Asn | Cys | Gly | Lys | Ala | Val | Tyr | Ser | Arg | Ile | Ala |
|     |     | 275 |     |     |     | 280 |     |     |     | 285 |     |     |     |
| Arg | Val | Cys | Lys | Lys | Asp | Val | Gly | Gly | Lys | Asn | Leu | Leu | Ala | His | Asn |
|     | 290 |     |     |     | 295 |     |     |     | 300 |     |     |     |
| Trp | Ala | Thr | Tyr | Leu | Lys | Ala | Arg | Leu | Asn | Cys | Ser | Ile | Ser | Gly | Glu |
| 305 |     |     |     | 310 |     |     |     | 315 |     |     |     | 320 |
| Phe | Pro | Phe | Tyr | Phe | Asn | Glu | Ile | Gln | Ser | Val | Tyr | Gln | Leu | Pro | Ser |
|     |     |     | 325 |     |     |     | 330 |     |     |     | 335 |
| Asp | Lys | Ser | Arg | Phe | Phe | Ala | Thr | Phe | Thr | Thr | Ser | Thr | Asn | Gly | Leu |
|     |     |     | 340 |     |     |     | 345 |     |     |     | 350 |
| Ile | Gly | Ser | Ala | Val | Cys | Ser | Phe | His | Ile | Asn | Glu | Ile | Gln | Ala | Ala |
|     |     | 355 |     |     |     | 360 |     |     |     | 365 |     |     |
| Phe | Asn | Gly | Lys | Phe | Lys | Glu | Gln | Ser | Ser | Ser | Asn | Ser | Ala | Trp | Leu |
|     | 370 |     |     |     | 375 |     |     |     | 380 |     |     |     |
| Pro | Val | Leu | Asn | Ser | Arg | Val | Pro | Glu | Pro | Arg | Pro | Gly | Thr | Cys | Val |
| 385 |     |     |     | 390 |     |     |     | 395 |     |     |     | 400 |
| Asn | Asp | Thr | Ser | Asn | Leu | Pro | Asp | Thr | Val | Leu | Asn | Phe | Ile | Arg | Ser |
|     |     |     | 405 |     |     |     | 410 |     |     |     | 415 |
| His | Pro | Leu | Met | Asp | Lys | Ala | Val | Asn | His | Glu | His | Asn | Asn | Pro | Val |
|     |     |     | 420 |     |     |     | 425 |     |     |     | 430 |
| Tyr | Tyr | Lys | Arg | Asp | Leu | Val | Phe | Thr | Lys | Leu | Val | Val | Asp | Lys | Ile |
|     |     | 435 |     |     |     | 440 |     |     |     | 445 |     |
| Arg | Ile | Asp | Ile | Leu | Asn | Gln | Glu | Tyr | Ile | Val | Tyr | Val | Gly | Thr |
|     | 450 |     |     |     | 455 |     |     |     | 460 |     |     |
| Asn | Leu | Gly | Arg | Ile | Tyr | Lys | Ile | Val | Gln | Tyr | Tyr | Arg | Asn | Gly | Glu |
| 465 |     |     |     | 470 |     |     |     | 475 |     |     |     | 480 |
| Ser | Leu | Ser | Lys | Leu | Leu | Asp | Ile | Phe | Glu | Val | Ala | Pro | Asn | Glu | Ala |
|     |     |     | 485 |     |     |     | 490 |     |     |     | 495 |
| Ile | Gln | Val | Met | Glu | Ile | Ser | Gln | Thr | Arg | Lys | Ser | Leu | Tyr | Ile | Gly |
|     |     |     | 500 |     |     |     | 505 |     |     |     | 510 |
| Thr | Asp | His | Arg | Ile | Lys | Gln | Ile | Asp | Leu | Ala | Met | Cys | Asn | Arg | Arg |
|     |     | 515 |     |     |     | 520 |     |     |     | 525 |     |     |
| Tyr | Asp | Asn | Cys | Phe | Arg | Cys | Val | Arg | Asp | Pro | Tyr | Cys | Gly | Trp | Asp |
|     | 530 |     |     |     | 535 |     |     |     | 540 |     |     |     |
| Lys | Glu | Ala | Asn | Thr | Cys | Arg | Pro | Tyr | Glu | Leu | Asp | Leu | Leu | Gln | Asp |
| 545 |     |     |     | 550 |     |     |     | 555 |     |     |     | 560 |
| Val | Ala | Asn | Glu | Thr | Ser | Asp | Ile | Cys | Asp | Ser | Ser | Val | Leu | Lys | Lys |
|     |     |     | 565 |     |     |     | 570 |     |     |     | 575 |
| Lys | Ile | Val | Val | Thr | Tyr | Gly | Gln | Ser | Val | His | Leu | Gly | Cys | Phe | Val |
|     |     |     | 580 |     |     |     | 585 |     |     |     | 590 |
| Lys | Ile | Pro | Glu | Val | Leu | Lys | Asn | Glu | Gln | Val | Thr | Trp | Tyr | His | His |
|     |     | 595 |     |     |     | 600 |     |     |     | 605 |     |
| Ser | Lys | Asp | Lys | Gly | Arg | Tyr | Glu | Ile | Arg | Tyr | Ser | Pro | Thr | Lys | Tyr |
|     |     | 610 |     |     |     | 615 |     |     |     | 620 |     |
| Ile | Glu | Thr | Thr | Glu | Arg | Gly | Leu | Val | Val | Ser | Val | Asn | Glu | Ala |
| 625 |     |     |     | 630 |     |     |     | 635 |     |     |     | 640 |
| Asp | Gly | Gly | Arg | Tyr | Asp | Cys | His | Leu | Gly | Gly | Ser | Leu | Leu | Cys | Ser |
|     |     |     | 645 |     |     |     | 650 |     |     |     | 655 |
| Tyr | Asn | Ile | Thr | Val | Asp | Ala | His | Arg | Cys | Thr | Pro | Pro | Asn | Lys | Ser |
|     |     |     | 660 |     |     |     | 665 |     |     |     | 670 |

| Asn | Asp | Tyr | Gln | Lys | Ile | Tyr | Ser | Asp | Trp | Cys | His | Glu | Phe | Glu | Lys |
|---|---|---|---|---|---|---|---|---|---|---|---|---|---|---|---|
| | | 675 | | | | 680 | | | | | 685 | | | | |

| Tyr | Lys | Thr | Ala | Met | Lys | Ser | Trp | Glu | Lys | Lys | Gln | Gly | Gln | Cys | Ser |
|---|---|---|---|---|---|---|---|---|---|---|---|---|---|---|---|
| | | 690 | | | | 695 | | | | 700 | | | | | |

| Thr | Arg | Gln | Asn | Phe | Ser | Cys | Asn | Gln | His | Pro | Asn | Glu | Ile | Phe | Arg |
|---|---|---|---|---|---|---|---|---|---|---|---|---|---|---|---|
| 705 | | | | | 710 | | | | 715 | | | | | | 720 |

Lys Pro Asn Val (2) INFORMATION FOR SEQ ID NO:63:

(i) SEQUENCE CHARACTERISTICS:
        (A) LENGTH: 2504 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 355..2493

(xi) SEQUENCE DESCRIPTION: SEQ ID NO:63:

```
GGCCGGTCGA CCACGAGCGA AGTTTAGTAT CAAGTTGAGA GTTTGTTTGG AGCGTAGTTT      60

ACGGAGCGTA CATTTAAATT TGCGGACAAA TCGTGTTTTG GTGCTTCTCT GTGGATTGTT     120

GTGTTCTTGA AGATGCTTCC CTTGGTTTTC GGATAAGCTT TCCTGTGGAT TGTTGTGTTC     180

TTGAAGATGC TTCCCTTGGT TTTCGGATAA GCTTTCCAGC GTGGTTTCAG CCTCGGCTTG     240

TTTGGACCCC GACATAATCT TCGAACTACA ATGAAGAGGA AATTTTGAAA CGCGTTTCAG     300

ACGCGTACAA TCGACAAAAT GTTTGGTTTC CAATTGATCT TGCAATGTAG CTAC ATG       357
                                                              Met
                                                                1
```

| GTG | GTG | AAG | ATC | TTG | GTT | TGG | TCG | ATA | TGT | CTG | ATA | GCG | CTG | TGT | CAT | 405 |
|---|---|---|---|---|---|---|---|---|---|---|---|---|---|---|---|---|
| Val | Val | Lys | Ile | Leu | Val | Trp | Ser | Ile | Cys | Leu | Ile | Ala | Leu | Cys | His | |
| | | | 5 | | | | | 10 | | | | | 15 | | | |

| GCT | TGG | ATG | CCG | GAT | AGT | TCT | TCC | AAA | TTA | ATA | AAC | CAT | TTT | AAA | TCA | 453 |
|---|---|---|---|---|---|---|---|---|---|---|---|---|---|---|---|---|
| Ala | Trp | Met | Pro | Asp | Ser | Ser | Ser | Lys | Leu | Ile | Asn | His | Phe | Lys | Ser | |
| | | 20 | | | | | 25 | | | | | 30 | | | | |

| GTT | GAA | AGT | AAA | AGC | TTT | ACC | GGG | AAC | GCC | ACG | TTC | CCT | GAT | CAC | TTT | 501 |
|---|---|---|---|---|---|---|---|---|---|---|---|---|---|---|---|---|
| Val | Glu | Ser | Lys | Ser | Phe | Thr | Gly | Asn | Ala | Thr | Phe | Pro | Asp | His | Phe | |
| | 35 | | | | | 40 | | | | | 45 | | | | | |

| ATT | GTC | TTG | AAT | CAA | GAC | GAA | ACT | TCG | ATA | TTA | GTA | GGC | GGT | AGA | AAT | 549 |
|---|---|---|---|---|---|---|---|---|---|---|---|---|---|---|---|---|
| Ile | Val | Leu | Asn | Gln | Asp | Glu | Thr | Ser | Ile | Leu | Val | Gly | Gly | Arg | Asn | |
| 50 | | | | | 55 | | | | | 60 | | | | | 65 | |

| AGG | GTT | TAC | AAT | TTA | AGT | ATA | TTC | GAC | CTC | AGT | GAG | CGT | AAA | GGG | GGG | 597 |
|---|---|---|---|---|---|---|---|---|---|---|---|---|---|---|---|---|
| Arg | Val | Tyr | Asn | Leu | Ser | Ile | Phe | Asp | Leu | Ser | Glu | Arg | Lys | Gly | Gly | |
| | | | | 70 | | | | | 75 | | | | | 80 | | |

| CGA | ATC | GAC | TGG | CCA | TCG | TCC | GAT | GCA | CAT | GGC | CAG | TTG | TGT | ATA | TTG | 645 |
|---|---|---|---|---|---|---|---|---|---|---|---|---|---|---|---|---|
| Arg | Ile | Asp | Trp | Pro | Ser | Ser | Asp | Ala | His | Gly | Gln | Leu | Cys | Ile | Leu | |
| | | | | 85 | | | | | 90 | | | | | 95 | | |

| AAA | GGG | AAA | ACG | GAC | GAC | GAC | TGC | CAA | AAT | TAC | ATT | AGA | ATA | CTG | TAC | 693 |
|---|---|---|---|---|---|---|---|---|---|---|---|---|---|---|---|---|
| Lys | Gly | Lys | Thr | Asp | Asp | Asp | Cys | Gln | Asn | Tyr | Ile | Arg | Ile | Leu | Tyr | |
| | | 100 | | | | | 105 | | | | | 110 | | | | |

| TCT | TCA | GAA | CCG | GGG | AAA | TTA | GTT | ATT | TGC | GGG | ACC | AAT | TCG | TAC | AAA | 741 |
|---|---|---|---|---|---|---|---|---|---|---|---|---|---|---|---|---|
| Ser | Ser | Glu | Pro | Gly | Lys | Leu | Val | Ile | Cys | Gly | Thr | Asn | Ser | Tyr | Lys | |
| | 115 | | | | | 120 | | | | | 125 | | | | | |

| CCC | CTC | TGT | CGG | ACG | TAC | GCA | TTT | AAG | GAG | GGA | AAG | TAC | CTG | GTT | GAG | 789 |
|---|---|---|---|---|---|---|---|---|---|---|---|---|---|---|---|---|
| Pro | Leu | Cys | Arg | Thr | Tyr | Ala | Phe | Lys | Glu | Gly | Lys | Tyr | Leu | Val | Glu | |
| 130 | | | | | 135 | | | | | 140 | | | | | 145 | |

| | | | | | | | | | | | | | | | | |
|---|---|---|---|---|---|---|---|---|---|---|---|---|---|---|---|---|
| AAA | GAA | GTA | GAA | GGG | ATA | GGC | TTG | TGT | CCA | TAC | AAT | CCG | GAA | CAC | AAC | 837 |
| Lys | Glu | Val | Glu | Gly 150 | Ile | Gly | Leu | Cys 155 | Pro | Tyr | Asn | Pro | Glu | His 160 | Asn | |
| AGC | ACA | TCT | GTC | TCC | TAC | AAT | GGC | CAA | TTA | TTT | TCA | GCG | ACG | GTC | GCC | 885 |
| Ser | Thr | Ser | Val 165 | Ser | Tyr | Asn | Gly | Gln 170 | Leu | Phe | Ser | Ala | Thr 175 | Val | Ala | |
| GAC | TTT | TCC | GGG | GGC | GAC | CCT | CTC | ATA | TAC | AGG | GAG | CCC | CAG | CGC | ACC | 933 |
| Asp | Phe | Ser | Gly 180 | Gly | Asp | Pro | Leu | Ile 185 | Tyr | Arg | Glu | Pro | Gln 190 | Arg | Thr | |
| GAA | CTC | TCA | GAT | CTC | AAA | CAA | CTG | AAC | GCA | CCG | AAT | TTC | GTA | AAC | TCG | 981 |
| Glu | Leu 195 | Ser | Asp | Leu | Lys | Gln 200 | Leu | Asn | Ala | Pro | Asn 205 | Phe | Val | Asn | Ser | |
| GTG | GCC | TAT | GGC | GAC | TAC | ATA | TTC | TTC | TTC | TAC | CGT | GAA | ACC | GCC | GTC | 1029 |
| Val 210 | Ala | Tyr | Gly | Asp | Tyr 215 | Ile | Phe | Phe | Phe | Tyr 220 | Arg | Glu | Thr | Ala | Val 225 | |
| GAG | TAC | ATG | AAC | TGC | GGA | AAA | GTC | ATC | TAC | TCG | CGG | GTC | GCC | AGG | GTG | 1077 |
| Glu | Tyr | Met | Asn | Cys 230 | Gly | Lys | Val | Ile | Tyr 235 | Ser | Arg | Val | Ala | Arg 240 | Val | |
| TGC | AAG | GAC | GAC | AAA | GGG | GGC | CCT | CAC | CAG | TCA | CGC | GAC | CGC | TGG | ACG | 1125 |
| Cys | Lys | Asp | Asp 245 | Lys | Gly | Gly | Pro | His 250 | Gln | Ser | Arg | Asp | Arg 255 | Trp | Thr | |
| TCG | TTC | CTC | AAA | GCA | CGT | CTC | AAT | TGT | TCA | ATT | CCC | GGC | GAG | TAC | CCC | 1173 |
| Ser | Phe | Leu | Lys 260 | Ala | Arg | Leu | Asn | Cys 265 | Ser | Ile | Pro | Gly | Glu 270 | Tyr | Pro | |
| TTT | TAC | TTT | GAT | GAA | ATC | CAA | TCA | ACA | AGT | GAT | ATA | GTC | GAG | GGT | CGG | 1221 |
| Phe | Tyr 275 | Phe | Asp | Glu | Ile | Gln 280 | Ser | Thr | Ser | Asp | Ile 285 | Val | Glu | Gly | Arg | |
| TAC | AAT | TCC | GAC | GAC | AGC | AAA | AAG | ATC | ATT | TAT | GGA | ATC | CTC | ACA | ACT | 1269 |
| Tyr | Asn | Ser | Asp | Asp | Ser 295 | Lys | Lys | Ile | Ile | Tyr 300 | Gly | Ile | Leu | Thr | Thr 305 | |
| Tyr 290 | | | | | | | | | | | | | | | | |
| CCA | GTT | AAT | GCC | ATC | GGC | GGC | TCG | GCC | ATT | TGC | GCG | TAT | CAA | ATG | GCC | 1317 |
| Pro | Val | Asn | Ala | Ile 310 | Gly | Gly | Ser | Ala | Ile 315 | Cys | Ala | Tyr | Gln | Met 320 | Ala | |
| GAC | ATC | TTG | CGC | GTG | TTT | GAA | GGG | AGC | TTC | AAG | CAC | CAA | GAG | ACG | ATC | 1365 |
| Asp | Ile | Leu | Arg 325 | Val | Phe | Glu | Gly | Ser 330 | Phe | Lys | His | Gln | Glu 335 | Thr | Ile | |
| AAC | TCG | AAC | TGG | CTC | CCC | GTG | CCC | CAG | AAC | CTA | GTC | CCT | GAA | CCC | AGG | 1413 |
| Asn | Ser | Asn | Trp 340 | Leu | Pro | Val | Pro | Gln 345 | Asn | Leu | Val | Pro | Glu 350 | Pro | Arg | |
| CCC | GGG | CAG | TGC | GTA | CGC | GAC | AGC | AGG | ATC | CTG | CCC | GAC | AAG | AAC | GTC | 1461 |
| Pro | Gly 355 | Gln | Cys | Val | Arg | Asp 360 | Ser | Arg | Ile | Leu | Pro 365 | Asp | Lys | Asn | Val | |
| AAC | TTT | ATT | AAG | ACC | CAC | TCT | TTG | ATG | GAG | GAC | GTT | CCG | GCT | CTT | TTC | 1509 |
| Asn 370 | Phe | Ile | Lys | Thr | His 375 | Ser | Leu | Met | Glu | Asp 380 | Val | Pro | Ala | Leu | Phe 385 | |
| GGA | AAA | CCA | GTT | CTG | GTC | CGA | GTG | AGT | CTG | CAG | TAT | CGG | TTT | ACA | GCC | 1557 |
| Gly | Lys | Pro | Val | Leu 390 | Val | Arg | Val | Ser | Leu 395 | Gln | Tyr | Arg | Phe | Thr 400 | Ala | |
| ATA | ACA | GTG | GAT | CCA | CAA | GTG | AAA | ACA | ATC | AAT | AAT | CAG | TAT | CTC | GAT | 1605 |
| Ile | Thr | Val | Asp 405 | Pro | Gln | Val | Lys | Thr 410 | Ile | Asn | Asn | Gln | Tyr 415 | Leu | Asp | |
| GTT | TTG | TAT | ATC | GGA | ACA | GAT | GAT | GGG | AAG | GTA | CTA | AAA | GCT | GTT | AAT | 1653 |
| Val | Leu | Tyr 420 | Ile | Gly | Thr | Asp | Asp 425 | Gly | Lys | Val | Leu | Lys 430 | Ala | Val | Asn | |
| ATA | CCA | AAG | CGA | CAC | GCT | AAA | GCG | TTG | TTA | TAT | CGA | AAA | TAC | CGT | ACA | 1701 |
| Ile | Pro | Lys 435 | Arg | His | Ala | Lys | Ala 440 | Leu | Leu | Tyr | Arg | Lys 445 | Tyr | Arg | Thr | |
| TCC | GTA | CAT | CCG | CAC | GGA | GCT | CCC | GTA | AAA | CAG | CTG | AAG | ATC | GCT | CCC | 1749 |
| Ser | Val | His | Pro 450 | His | Gly | Ala | Pro | Val 455 | Lys | Gln | Leu | Lys | Ile 460 | Ala | Pro 465 | |

| | | | | | | | | | | | | | | | | |
|---|---|---|---|---|---|---|---|---|---|---|---|---|---|---|---|---|
| GGT | TAT | GGC | AAA | GTT | GTG | GTG | GTC | GGG | AAA | GAC | GAA | ATC | AGA | CTT | GCT | 1797 |
| Gly | Tyr | Gly | Lys 470 | Val | Val | Val | Val | Gly | Lys 475 | Asp | Glu | Ile | Arg | Leu 480 | Ala | |
| AAT | CTC | AAC | CAT | TGT | GCA | AGC | AAA | ACG | CGG | TGC | AAG | GAC | TGT | GTG | GAA | 1845 |
| Asn | Leu | Asn | His 485 | Cys | Ala | Ser | Lys | Thr 490 | Arg | Cys | Lys | Asp | Cys 495 | Val | Glu | |
| CTG | CAA | GAC | CCA | CAT | TGC | GCC | TGG | GAC | GCC | AAA | CAA | AAC | CTG | TGT | GTC | 1893 |
| Leu | Gln | Asp 500 | Pro | His | Cys | Ala | Trp | Asp 505 | Ala | Lys | Gln | Asn 510 | Leu | Cys | Val | |
| AGC | ATT | GAC | ACC | GTC | ACT | TCG | TAT | CGC | TTC | CTG | ATC | CAG | GAC | GTA | GTT | 1941 |
| Ser | Ile 515 | Asp | Thr | Val | Thr | Ser 520 | Tyr | Arg | Phe | Leu | Ile 525 | Gln | Asp | Val | Val | |
| CGC | GGC | GAC | GAC | AAC | AAA | TGT | TGG | TCG | CCG | CAA | ACA | GAC | AAA | AAG | ACT | 1989 |
| Arg 530 | Gly | Asp | Asp | Asn | Lys 535 | Cys | Trp | Ser | Pro | Gln 540 | Thr | Asp | Lys | Lys | Thr 545 | |
| GTG | ATT | AAG | AAT | AAG | CCC | AGC | GAG | GTT | GAG | AAC | GAG | ATT | ACG | AAC | TCC | 2037 |
| Val | Ile | Lys | Asn | Lys 550 | Pro | Ser | Glu | Val | Glu 555 | Asn | Glu | Ile | Thr | Asn 560 | Ser | |
| ATT | GAC | GAA | AAG | GAT | CTC | GAT | TCA | AGC | GAT | CCG | CTC | ATC | AAA | ACT | GGT | 2085 |
| Ile | Asp | Glu | Lys 565 | Asp | Leu | Asp | Ser | Ser 570 | Asp | Pro | Leu | Ile | Lys 575 | Thr | Gly | |
| CTC | GAT | GAC | GAT | TCC | GAT | TGT | GAT | CCA | GTC | AGC | GAG | AAC | AGC | ATA | GGC | 2133 |
| Leu | Asp | Asp 580 | Asp | Ser | Asp | Cys | Asp 585 | Pro | Val | Ser | Glu | Asn 590 | Ser | Ile | Gly | |
| GGA | TGC | GCC | GTC | CGC | CAG | CAA | CTT | GTT | ATA | TAC | ACA | GCT | GGG | ACT | CTA | 2181 |
| Gly | Cys 595 | Ala | Val | Arg | Gln | Gln 600 | Leu | Val | Ile | Tyr | Thr 605 | Ala | Gly | Thr | Leu | |
| CAC | ATT | GTC | GTG | GTC | GTC | GTC | AGC | ATC | GTG | GGT | TTA | TTT | TCT | TGG | CTT | 2229 |
| His 610 | Ile | Val | Val | Val | Val 615 | Val | Ser | Ile | Val | Gly 620 | Leu | Phe | Ser | Trp | Leu 625 | |
| TAT | AGC | GGG | TTA | TCT | GTT | TTC | GCA | AAA | TTT | CAC | TCG | GAT | TCG | CAA | TAT | 2277 |
| Tyr | Ser | Gly | Leu | Ser 630 | Val | Phe | Ala | Lys | Phe 635 | His | Ser | Asp | Ser | Gln 640 | Tyr | |
| CCT | GAG | GCG | CCG | TTT | ATA | GAG | CAG | CAC | AAT | CAT | TTG | GAA | AGA | TTA | AGC | 2325 |
| Pro | Glu | Ala | Pro 645 | Phe | Ile | Glu | Gln | His 650 | Asn | His | Leu | Glu | Arg 655 | Leu | Ser | |
| GCC | AAC | CAG | ACG | GGG | TAT | TTG | ACT | CCG | AGG | GCC | AAT | AAA | GCG | GTC | AAT | 2373 |
| Ala | Asn | Gln 660 | Thr | Gly | Tyr | Leu | Thr 665 | Pro | Arg | Ala | Asn | Lys 670 | Ala | Val | Asn | |
| TTG | GTG | GTG | AAG | GTG | TCT | AGT | AGC | ACG | CCG | CGG | CCG | AAA | AAG | GAC | AAT | 2421 |
| Leu | Val 675 | Val | Lys | Val | Ser | Ser 680 | Ser | Thr | Pro | Arg | Pro 685 | Lys | Lys | Asp | Asn | |
| CTC | GAT | GTC | AGC | AAA | GAC | TTG | AAC | ATT | GCG | AGT | GAC | GGG | ACT | TTG | CAA | 2469 |
| Leu 690 | Asp | Val | Ser | Lys 695 | Asp | Leu | Asn | Ile | Ala 700 | Ser | Asp | Gly | Thr | Leu 705 | Gln | |
| AAA | ATC | AAG | AAG | ACT | TAC | ATT | TAGTGCGACT | TTTT | | | | | | | | 2504 |
| Lys | Ile | Lys | Lys | Thr 710 | Tyr | Ile | | | | | | | | | | |

( 2 ) INFORMATION FOR SEQ ID NO:64:

( i ) SEQUENCE CHARACTERISTICS:
        ( A ) LENGTH: 712 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

| | | | | | | | | | | | | | | | |
|---|---|---|---|---|---|---|---|---|---|---|---|---|---|---|---|
| Met 1 | Val | Val | Lys | Ile 5 | Leu | Val | Trp | Ser | Cys 10 | Leu | Ile | Ala | Leu | Cys 15 | |
| His | Ala | Trp | Met | Pro | Asp | Ser | Ser | Ser | Lys | Leu | Ile | Asn | His | Phe | Lys |

-continued

|  |  | 20 |  |  |  |  | 25 |  |  |  |  | 30 |  |  |
|---|---|---|---|---|---|---|---|---|---|---|---|---|---|---|
| Ser | Val | Glu | Ser | Lys | Ser | Phe | Thr | Gly | Asn | Ala | Thr | Phe | Pro | Asp | His |
|  |  | 35 |  |  |  |  | 40 |  |  |  |  | 45 |  |  |
| Phe | Ile | Val | Leu | Asn | Gln | Asp | Glu | Thr | Ser | Ile | Leu | Val | Gly | Gly | Arg |
|  |  | 50 |  |  |  |  | 55 |  |  |  |  | 60 |  |  |
| Asn | Arg | Val | Tyr | Asn | Leu | Ser | Ile | Phe | Asp | Leu | Ser | Glu | Arg | Lys | Gly |
| 65 |  |  |  |  | 70 |  |  |  |  | 75 |  |  |  |  | 80 |
| Gly | Arg | Ile | Asp | Trp | Pro | Ser | Ser | Asp | Ala | His | Gly | Gln | Leu | Cys | Ile |
|  |  |  |  | 85 |  |  |  |  | 90 |  |  |  |  | 95 |  |
| Leu | Lys | Gly | Lys | Thr | Asp | Asp | Asp | Cys | Gln | Asn | Tyr | Ile | Arg | Ile | Leu |
|  |  |  |  | 100 |  |  |  |  | 105 |  |  |  |  | 110 |  |
| Tyr | Ser | Ser | Glu | Pro | Gly | Lys | Leu | Val | Ile | Cys | Gly | Thr | Asn | Ser | Tyr |
|  |  |  |  | 115 |  |  |  |  | 120 |  |  |  |  | 125 |  |
| Lys | Pro | Leu | Cys | Arg | Thr | Tyr | Ala | Phe | Lys | Glu | Gly | Lys | Tyr | Leu | Val |
|  |  |  |  | 130 |  |  |  |  | 135 |  |  |  |  | 140 |  |
| Glu | Lys | Glu | Val | Glu | Gly | Ile | Gly | Leu | Cys | Pro | Tyr | Asn | Pro | Glu | His |
| 145 |  |  |  |  | 150 |  |  |  |  | 155 |  |  |  |  | 160 |
| Asn | Ser | Thr | Ser | Val | Ser | Tyr | Asn | Gly | Gln | Leu | Phe | Ser | Ala | Thr | Val |
|  |  |  |  | 165 |  |  |  |  | 170 |  |  |  |  | 175 |  |
| Ala | Asp | Phe | Ser | Gly | Gly | Asp | Pro | Leu | Ile | Tyr | Arg | Glu | Pro | Gln | Arg |
|  |  |  | 180 |  |  |  |  | 185 |  |  |  |  | 190 |  |  |
| Thr | Glu | Leu | Ser | Asp | Leu | Lys | Gln | Leu | Asn | Ala | Pro | Asn | Phe | Val | Asn |
|  |  |  | 195 |  |  |  |  | 200 |  |  |  |  | 205 |  |  |
| Ser | Val | Ala | Tyr | Gly | Asp | Tyr | Ile | Phe | Phe | Phe | Tyr | Arg | Glu | Thr | Ala |
|  | 210 |  |  |  |  | 215 |  |  |  |  | 220 |  |  |  |  |
| Val | Glu | Tyr | Met | Asn | Cys | Gly | Lys | Val | Ile | Tyr | Ser | Arg | Val | Ala | Arg |
| 225 |  |  |  |  | 230 |  |  |  |  | 235 |  |  |  |  | 240 |
| Val | Cys | Lys | Asp | Asp | Lys | Gly | Gly | Pro | His | Gln | Ser | Arg | Asp | Arg | Trp |
|  |  |  |  | 245 |  |  |  |  | 250 |  |  |  |  | 255 |  |
| Thr | Ser | Phe | Leu | Lys | Ala | Arg | Leu | Asn | Cys | Ser | Ile | Pro | Gly | Glu | Tyr |
|  |  |  |  | 260 |  |  |  |  | 265 |  |  |  |  | 270 |  |
| Pro | Phe | Tyr | Phe | Asp | Glu | Ile | Gln | Ser | Thr | Ser | Asp | Ile | Val | Glu | Gly |
|  |  |  | 275 |  |  |  |  | 280 |  |  |  |  | 285 |  |  |
| Arg | Tyr | Asn | Ser | Asp | Asp | Ser | Lys | Lys | Ile | Ile | Tyr | Gly | Ile | Leu | Thr |
|  | 290 |  |  |  |  | 295 |  |  |  |  | 300 |  |  |  |  |
| Thr | Pro | Val | Asn | Ala | Ile | Gly | Gly | Ser | Ala | Ile | Cys | Ala | Tyr | Gln | Met |
| 305 |  |  |  |  | 310 |  |  |  |  | 315 |  |  |  |  | 320 |
| Ala | Asp | Ile | Leu | Arg | Val | Phe | Glu | Gly | Ser | Phe | Lys | His | Gln | Glu | Thr |
|  |  |  |  | 325 |  |  |  |  | 330 |  |  |  |  | 335 |  |
| Ile | Asn | Ser | Asn | Trp | Leu | Pro | Val | Pro | Gln | Asn | Leu | Val | Pro | Glu | Pro |
|  |  |  |  | 340 |  |  |  |  | 345 |  |  |  |  | 350 |  |
| Arg | Pro | Gly | Gln | Cys | Val | Arg | Asp | Ser | Arg | Ile | Leu | Pro | Asp | Lys | Asn |
|  |  |  | 355 |  |  |  |  | 360 |  |  |  |  | 365 |  |  |
| Val | Asn | Phe | Ile | Lys | Thr | His | Ser | Leu | Met | Glu | Asp | Val | Pro | Ala | Leu |
|  | 370 |  |  |  |  | 375 |  |  |  |  | 380 |  |  |  |  |
| Phe | Gly | Lys | Pro | Val | Leu | Val | Arg | Val | Ser | Leu | Gln | Tyr | Arg | Phe | Thr |
| 385 |  |  |  |  | 390 |  |  |  |  | 395 |  |  |  |  | 400 |
| Ala | Ile | Thr | Val | Asp | Pro | Gln | Val | Lys | Thr | Ile | Asn | Asn | Gln | Tyr | Leu |
|  |  |  |  | 405 |  |  |  |  | 410 |  |  |  |  | 415 |  |
| Asp | Val | Leu | Tyr | Ile | Gly | Thr | Asp | Asp | Gly | Lys | Val | Leu | Lys | Ala | Val |
|  |  |  | 420 |  |  |  |  | 425 |  |  |  |  | 430 |  |  |
| Asn | Ile | Pro | Lys | Arg | His | Ala | Lys | Ala | Leu | Leu | Tyr | Arg | Lys | Tyr | Arg |
|  |  |  | 435 |  |  |  |  | 440 |  |  |  |  | 445 |  |  |

| Thr | Ser | Val | His | Pro | His | Gly | Ala | Pro | Val | Lys | Gln | Leu | Lys | Ile | Ala |
|---|---|---|---|---|---|---|---|---|---|---|---|---|---|---|---|
| | 450 | | | | 455 | | | | | 460 | | | | | |

| Pro | Gly | Tyr | Gly | Lys | Val | Val | Val | Gly | Lys | Asp | Glu | Ile | Arg | Leu |
|---|---|---|---|---|---|---|---|---|---|---|---|---|---|---|
| 465 | | | | | 470 | | | | 475 | | | | | 480 |

| Ala | Asn | Leu | Asn | His | Cys | Ala | Ser | Lys | Thr | Arg | Cys | Lys | Asp | Cys | Val |
|---|---|---|---|---|---|---|---|---|---|---|---|---|---|---|---|
| | | | | 485 | | | | | 490 | | | | | 495 | |

| Glu | Leu | Gln | Asp | Pro | His | Cys | Ala | Trp | Asp | Ala | Lys | Gln | Asn | Leu | Cys |
|---|---|---|---|---|---|---|---|---|---|---|---|---|---|---|---|
| | | | 500 | | | | | 505 | | | | | 510 | | |

| Val | Ser | Ile | Asp | Thr | Val | Thr | Ser | Tyr | Arg | Phe | Leu | Ile | Gln | Asp | Val |
|---|---|---|---|---|---|---|---|---|---|---|---|---|---|---|---|
| | | 515 | | | | | 520 | | | | | 525 | | | |

| Val | Arg | Gly | Asp | Asp | Asn | Lys | Cys | Trp | Ser | Pro | Gln | Thr | Asp | Lys | Lys |
|---|---|---|---|---|---|---|---|---|---|---|---|---|---|---|---|
| | 530 | | | | | 535 | | | | | 540 | | | | |

| Thr | Val | Ile | Lys | Asn | Lys | Pro | Ser | Glu | Val | Glu | Asn | Glu | Ile | Thr | Asn |
|---|---|---|---|---|---|---|---|---|---|---|---|---|---|---|---|
| 545 | | | | | 550 | | | | | 555 | | | | | 560 |

| Ser | Ile | Asp | Glu | Lys | Asp | Leu | Asp | Ser | Ser | Asp | Pro | Leu | Ile | Lys | Thr |
|---|---|---|---|---|---|---|---|---|---|---|---|---|---|---|---|
| | | | | 565 | | | | | 570 | | | | | 575 | |

| Gly | Leu | Asp | Asp | Asp | Ser | Asp | Cys | Asp | Pro | Val | Ser | Glu | Asn | Ser | Ile |
|---|---|---|---|---|---|---|---|---|---|---|---|---|---|---|---|
| | | | 580 | | | | | 585 | | | | | 590 | | |

| Gly | Gly | Cys | Ala | Val | Arg | Gln | Gln | Leu | Val | Ile | Tyr | Thr | Ala | Gly | Thr |
|---|---|---|---|---|---|---|---|---|---|---|---|---|---|---|---|
| | | 595 | | | | | 600 | | | | | 605 | | | |

| Leu | His | Ile | Val | Val | Val | Val | Ser | Ile | Val | Gly | Leu | Phe | Ser | Trp |
|---|---|---|---|---|---|---|---|---|---|---|---|---|---|---|
| | 610 | | | | | 615 | | | | | 620 | | | |

| Leu | Tyr | Ser | Gly | Leu | Ser | Val | Phe | Ala | Lys | Phe | His | Ser | Asp | Ser | Gln |
|---|---|---|---|---|---|---|---|---|---|---|---|---|---|---|---|
| 625 | | | | | 630 | | | | | 635 | | | | | 640 |

| Tyr | Pro | Glu | Ala | Pro | Phe | Ile | Glu | Gln | His | Asn | His | Leu | Glu | Arg | Leu |
|---|---|---|---|---|---|---|---|---|---|---|---|---|---|---|---|
| | | | | 645 | | | | | 650 | | | | | 655 | |

| Ser | Ala | Asn | Gln | Thr | Gly | Tyr | Leu | Thr | Pro | Arg | Ala | Asn | Lys | Ala | Val |
|---|---|---|---|---|---|---|---|---|---|---|---|---|---|---|---|
| | | | 660 | | | | | 665 | | | | | 670 | | |

| Asn | Leu | Val | Val | Lys | Val | Ser | Ser | Ser | Thr | Pro | Arg | Pro | Lys | Lys | Asp |
|---|---|---|---|---|---|---|---|---|---|---|---|---|---|---|---|
| | | 675 | | | | | 680 | | | | | 685 | | | |

| Asn | Leu | Asp | Val | Ser | Lys | Asp | Leu | Asn | Ile | Ala | Ser | Asp | Gly | Thr | Leu |
|---|---|---|---|---|---|---|---|---|---|---|---|---|---|---|---|
| | 690 | | | | | 695 | | | | | 700 | | | | |

| Gln | Lys | Ile | Lys | Lys | Thr | Tyr | Ile |
|---|---|---|---|---|---|---|---|
| 705 | | | | | 710 | | |

(2) INFORMATION FOR SEQ ID NO:65:

(i) SEQUENCE CHARACTERISTICS:
        (A) LENGTH: 369 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..369

(xi) SEQUENCE DESCRIPTION: SEQ ID NO:65:

| ATG | ATT | TAT | TTA | TAC | ACG | GCG | GAT | AAC | GTA | ATT | CCA | AAA | GAT | GGT | TTA | 48 |
|---|---|---|---|---|---|---|---|---|---|---|---|---|---|---|---|---|
| Met | Ile | Tyr | Leu | Tyr | Thr | Ala | Asp | Asn | Val | Ile | Pro | Lys | Asp | Gly | Leu | |
| 1 | | | | 5 | | | | | 10 | | | | | 15 | | |

| CAA | GGA | GCA | TTT | GTC | GAT | AAA | GAC | GGT | ACT | TAT | GAC | AAA | GTT | TAC | ATT | 96 |
|---|---|---|---|---|---|---|---|---|---|---|---|---|---|---|---|---|
| Gln | Gly | Ala | Phe | Val | Asp | Lys | Asp | Gly | Thr | Tyr | Asp | Lys | Val | Tyr | Ile | |
| | | | 20 | | | | | 25 | | | | | 30 | | | |

| CTT | TTC | ACT | GTT | ACT | ATC | GGC | TCA | AAG | AGA | ATT | GTT | AAA | ATT | CCG | TAT | 144 |
|---|---|---|---|---|---|---|---|---|---|---|---|---|---|---|---|---|
| Leu | Phe | Thr | Val | Thr | Ile | Gly | Ser | Lys | Arg | Ile | Val | Lys | Ile | Pro | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| ATA | GCA | CAA | ATG | TGC | TTA | AAC | GAC | GAA | TGT | GGT | CCA | TCA | TCA | TTG | TCT | 192 |
| Ile | Ala | Gln | Met | Cys | Leu | Asn | Asp | Glu | Cys | Gly | Pro | Ser | Ser | Leu | Ser | |
| | 50 | | | | | 55 | | | | | 60 | | | | | |
| AGT | CAT | AGA | TGG | TCG | ACG | TTG | CTC | AAA | GTC | GAA | TTA | GAA | TGT | GAC | ATC | 240 |
| Ser | His | Arg | Trp | Ser | Thr | Leu | Leu | Lys | Val | Glu | Leu | Glu | Cys | Asp | Ile | |
| 65 | | | | | 70 | | | | | 75 | | | | | 80 | |
| GAC | GGA | AGA | AGT | TAT | AGT | CAA | ATT | AAT | CAT | TCT | AAA | ACT | ATA | AAA | CAG | 288 |
| Asp | Gly | Arg | Ser | Tyr | Ser | Gln | Ile | Asn | His | Ser | Lys | Thr | Ile | Lys | Gln | |
| | | | | 85 | | | | | 90 | | | | | 95 | | |
| ATA | ATG | ATA | CGA | TAC | TAT | ATG | TAT | TCT | TTG | ATA | GTC | CTT | TTC | CAA | GTC | 336 |
| Ile | Met | Ile | Arg | Tyr | Tyr | Met | Tyr | Ser | Leu | Ile | Val | Leu | Phe | Gln | Val | |
| | | | 100 | | | | | 105 | | | | | 110 | | | |
| CGC | ATT | ATG | TAC | CTA | TTC | TAT | GAA | TAC | CAT | TAA | | | | | | 369 |
| Arg | Ile | Met | Tyr | Leu | Phe | Tyr | Glu | Tyr | His | | | | | | | |
| | | 115 | | | | | 120 | | | | | | | | | |

( 2 ) INFORMATION FOR SEQ ID NO:66:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

| | | | | | | | | | | | | | | |
|---|---|---|---|---|---|---|---|---|---|---|---|---|---|---|
| Met | Ile | Tyr | Leu | Tyr | Thr | Ala | Asp | Asn | Val | Ile | Pro | Lys | Asp | Gly | Leu |
| 1 | | | | 5 | | | | | 10 | | | | | 15 | |
| Gln | Gly | Ala | Phe | Val | Asp | Lys | Asp | Gly | Thr | Tyr | Asp | Lys | Val | Tyr | Ile |
| | | | 20 | | | | | 25 | | | | | 30 | | |
| Leu | Phe | Thr | Val | Thr | Ile | Gly | Ser | Lys | Arg | Ile | Val | Lys | Ile | Pro | Tyr |
| | | 35 | | | | | 40 | | | | | 45 | | | |
| Ile | Ala | Gln | Met | Cys | Leu | Asn | Asp | Glu | Cys | Gly | Pro | Ser | Ser | Leu | Ser |
| | 50 | | | | | 55 | | | | | 60 | | | | |
| Ser | His | Arg | Trp | Ser | Thr | Leu | Leu | Lys | Val | Glu | Leu | Glu | Cys | Asp | Ile |
| 65 | | | | | 70 | | | | | 75 | | | | | 80 |
| Asp | Gly | Arg | Ser | Tyr | Ser | Gln | Ile | Asn | His | Ser | Lys | Thr | Ile | Lys | Gln |
| | | | | 85 | | | | | 90 | | | | | 95 | |
| Ile | Met | Ile | Arg | Tyr | Tyr | Met | Tyr | Ser | Leu | Ile | Val | Leu | Phe | Gln | Val |
| | | | 100 | | | | | 105 | | | | | 110 | | |
| Arg | Ile | Met | Tyr | Leu | Phe | Tyr | Glu | Tyr | His | | | | | | |
| | | 115 | | | | | 120 | | | | | | | | |

( 2 ) INFORMATION FOR SEQ ID NO:67:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:67:

Asp  Cys  Gln  Asn  Tyr  Ile
    1                     5

( 2 ) INFORMATION FOR SEQ ID NO:68:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=SEQ68
        / note= "Xaa denotes N or G at residue #4; and A or S at residue #5"

( x i ) SEQUENCE DESCRIPTION: SEQ ID NO:68:

Cys Gly Thr Xaa Xaa Xaa Xaa Pro
1                  5

( 2 ) INFORMATION FOR SEQ ID NO:69:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ69
            / note= "Xaa denotes S or C at residue #3"

( x i ) SEQUENCE DESCRIPTION: SEQ ID NO:69:

Gly Xaa Xaa Pro Tyr Asp Pro
1                5

( 2 ) INFORMATION FOR SEQ ID NO:70:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ70
            / note= "Xaa denotes V, N or A"

( x i ) SEQUENCE DESCRIPTION: SEQ ID NO:70:

Leu Tyr Ser Gly Thr Xaa Ala
1                5

( 2 ) INFORMATION FOR SEQ ID NO:71:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

Leu Asn Ala Pro Asn Phe Val
1                5

( 2 ) INFORMATION FOR SEQ ID NO:72:

( i ) SEQUENCE CHARACTERISTICS:
        ( A ) LENGTH: 7 amino acids ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1..7
                    ( D ) OTHER INFORMATION: /label=SEQ72
                            / note= "Xaa denotes V or I"

( x i ) SEQUENCE DESCRIPTION: SEQ ID NO:72:

Arg  Xaa  Ala  Arg  Val  Cys  Lys ( 2 ) INFORMATION FOR SEQ ID NO:73:

( i ) SEQUENCE CHARACTERISTICS:
                    ( A ) LENGTH: 9 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1..9
                    ( D ) OTHER INFORMATION: /label=SEQ73
                            / note= "Xaa denotes T or A at residue #2; T or S
                            at residue #3; F or Y at residue #4; and A or S at
                            residue #7"

( x i ) SEQUENCE DESCRIPTION: SEQ ID NO:73:

Trp  Xaa  Xaa  Xaa  Leu  Lys  Xaa  Arg  Leu
        1                        5

( 2 ) INFORMATION FOR SEQ ID NO:74:

( i ) SEQUENCE CHARACTERISTICS:
                    ( A ) LENGTH: 9 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1..9
                    ( D ) OTHER INFORMATION: /label=SEQ74
                            / note= "Xaa denotes N or D"

( x i ) SEQUENCE DESCRIPTION: SEQ ID NO:74:

Pro  Phe  Tyr  Phe  Xaa  Glu  Ile  Gln  Ser
        1                        5

( 2 ) INFORMATION FOR SEQ ID NO:75:

( i ) SEQUENCE CHARACTERISTICS:
                    ( A ) LENGTH: 7 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1..7
                    ( D ) OTHER INFORMATION: /label=SEQ75
                            / note= "Xaa denotes F or Y at residue #7"

( x i ) SEQUENCE DESCRIPTION: SEQ ID NO:75:

```
       Gly  Ser  Ala  Val  Cys  Xaa  Xaa
       1                   5
```

( 2 ) INFORMATION FOR SEQ ID NO:76:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ76
            / note= "Xaa denotes P or A at residue #6"

( x i ) SEQUENCE DESCRIPTION: SEQ ID NO:76:

```
       Asn  Ser  Asn  Trp  Leu  Xaa  Val
       1                   5
```

( 2 ) INFORMATION FOR SEQ ID NO:77:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ77
            / note= "Xaa denotes E or D at residue #2; T, Q or S
            at residue #7"

( x i ) SEQUENCE DESCRIPTION: SEQ ID NO:77:

```
       Pro  Xaa  Pro  Arg  Pro  Gly  Xaa  Cys
       1                   5
```

( 2 ) INFORMATION FOR SEQ ID NO:78:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ78
            / note= "Xaa denotes A or G"

( x i ) SEQUENCE DESCRIPTION: SEQ ID NO:78:

```
       Asp  Pro  Tyr  Cys  Xaa  Trp  Asp
       1                   5
```

( 2 ) INFORMATION FOR SEQ ID NO:79:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=SEQ79
    / note= "Xaa denotes N or G at residue #4; A or S at residue #5; Y, F, H or G at residue #6; and K, R, H, N or Q at residue #7"

(xi) SEQUENCE DESCRIPTION: SEQ ID NO:79:

```
Cys Gly Thr Xaa Xaa Xaa Xaa
 1               5
```

(2) INFORMATION FOR SEQ ID NO:80:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=SEQ80
    / note= "Xaa denotes N or G at residue #4; A, S or N at residue #5; Y, F or H at residue #6; and K, R, H, N or Q at residue #7"

(xi) SEQUENCE DESCRIPTION: SEQ ID NO:80:

```
Cys Gly Thr Xaa Xaa Xaa Xaa
 1               5
```

(2) INFORMATION FOR SEQ ID NO:81:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..8
    (D) OTHER INFORMATION: /label=SEQ81
    / note= "Xaa denotes N or G at residue #4; and A or S at residue #5"

(xi) SEQUENCE DESCRIPTION: SEQ ID NO:81:

```
Cys Gly Thr Xaa Xaa Xaa Xaa Pro
 1               5
```

(2) INFORMATION FOR SEQ ID NO:82:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=SEQ82
    / note= "Xaa denotes K, F or Y at residue #2; F or Y at residue #4; F, Y, I or L at residue #5; F, Y or I at residue #6; and F or Y at residue #7"

( x i ) SEQUENCE DESCRIPTION: SEQ ID NO:82:

Asp Xaa Val Xaa Xaa Xaa Xaa
1               5

( 2 ) INFORMATION FOR SEQ ID NO:83:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ83
          / note= "Xaa denotes V or I at residue #1; F or Y
          at residue #2; F, Y or L at residue #3; F, Y, I or L at
          residue #4; R or T at residue #6; and T or N at residue
          # 8"

( x i ) SEQUENCE DESCRIPTION: SEQ ID NO:83:

Xaa Xaa Xaa Xaa Phe Xaa Xaa Xaa
1               5

( 2 ) INFORMATION FOR SEQ ID NO:84:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ84
          / note= "Xaa denotes V or I at residue #1; F or Y
          at residue #2; F, Y, I or L at residue #3; F, Y or I at
          residue #4; R or T at residue #6; and T or N at residue
          # 8"

( x i ) SEQUENCE DESCRIPTION: SEQ ID NO:84:

Xaa Xaa Xaa Xaa Phe Xaa Xaa Xaa
1               5

( 2 ) INFORMATION FOR SEQ ID NO:85:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ85
          / note= "Xaa denotes V or I at residue #1; F or Y
          at residue #2; F, Y, I or L at residue #3; F, Y, I or L
          at residue #4; and T or N at residue #8"

( x i ) SEQUENCE DESCRIPTION: SEQ ID NO:85:

Xaa Xaa Xaa Xaa Phe Arg Xaa Xaa
1               5

( 2 ) INFORMATION FOR SEQ ID NO:86:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ86
            / note= "Xaa denotes V or I at residue #1; F or Y
            at residue #2; F, Y or L at residue #3; F, Y, I or L at
            residue #4; F or Y at residue #5, R or T at residue #6,
            E, D or V at residue #7; and T or N at residue #8"

( x i ) SEQUENCE DESCRIPTION: SEQ ID NO:86:

```
Xaa  Xaa  Xaa  Xaa  Xaa  Xaa  Xaa  Xaa
1                   5
```

( 2 ) INFORMATION FOR SEQ ID NO:87:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ87
            / note= "Xaa denotes R, K or N at residue #1; T or A
            at residue #3; T, A or S at residue #4; F, Y or L at
            residue #5; and K or R at residue #7"

( x i ) SEQUENCE DESCRIPTION: SEQ ID NO:87:

```
Xaa  Trp  xaa  Xaa  Xaa  Leu  Xaa
1                   5
```

( 2 ) INFORMATION FOR SEQ ID NO:88:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=SEQ88
            / note= "Xaa denotes T or A at residue #2; T, A or S
            at residue #3; F, Y or L at residue #4; A, S, V, I or L
            at residue #7"

( x i ) SEQUENCE DESCRIPTION: SEQ ID NO:88:

```
Trp  Xaa  Xaa  Xaa  Leu  Lys  Xaa  Xaa  Leu
1                   5
```

( 2 ) INFORMATION FOR SEQ ID NO:89:

( i ) SEQUENCE CHARACTERISTICS:
        ( A ) LENGTH: 9 amino acids
        ( B ) TYPE: amino acid
        ( C ) STRANDEDNESS: single (D) TOPOLOGY: linear (ii) MOLECULE TYPE: peptide (ix) FEATURE:
 (A) NAME/KEY: Peptide
 (B) LOCATION: 1..9
 (D) OTHER INFORMATION: /label=SEQ89
  / note= "Xaa denotes T, A or S at residue #2; T, A or S
  at residue #3; F, Y or L at residue #4; A, S, I or L at
  residue #7"

(xi) SEQUENCE DESCRIPTION: SEQ ID NO:89:

Trp Xaa Xaa Xaa Leu Lys Xaa Xaa Leu
1       5

(2) INFORMATION FOR SEQ ID NO:90:

(i) SEQUENCE CHARACTERISTICS:
  (A) LENGTH: 11 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..11
  (D) OTHER INFORMATION: /label=SEQ90
   / note= "Xaa denotes T or A at residue #2; and T, A or S
   at residue #3"

(xi) SEQUENCE DESCRIPTION: SEQ ID NO:90:

Trp Xaa Xaa Xaa Leu Lys Xaa Xaa Leu Xaa Cys
1      5        10

(2) INFORMATION FOR SEQ ID NO:91:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..9
  (D) OTHER INFORMATION: /label=SEQ91
   / note= "Xaa denotes V, L or I at residue #1"

(xi) SEQUENCE DESCRIPTION: SEQ ID NO:91:

Xaa Pro Xaa Pro Arg Pro Gly Xaa Cys
1       5

(2) INFORMATION FOR SEQ ID NO:92:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1..7
  (D) OTHER INFORMATION: /label=SEQ92
   / note= "Xaa denotes K or Y at residue #2; F or Y
   at residue #4; F, Y or L at residue #5; F, Y, I or L at
   residue #6; and F or Y at residue #7"

( x i ) SEQUENCE DESCRIPTION: SEQ ID NO:92:

Asp Xaa Val Xaa Xaa Xaa Xaa
1               5

( 2 ) INFORMATION FOR SEQ ID NO:93:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ93
            / note= "Xaa denotes K or Y at residue #2; F or Y
            at residue #4; F, Y, I or L at residue #5; F, Y or I at
            residue #6; and F or Y at residue #7"

( x i ) SEQUENCE DESCRIPTION: SEQ ID NO:93:

Asp Xaa Val Xaa Xaa Xaa Xaa
1               5

( 2 ) INFORMATION FOR SEQ ID NO:94:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ94
            / note= "Xaa denotes V or I at residue #1; F, Y or L
            at residue #3; F, Y, I or L at residue #4; R or T at
            residue #6; and T or N at residue #8"

( x i ) SEQUENCE DESCRIPTION: SEQ ID NO:94:

Xaa Tyr Xaa Xaa Phe Xaa Xaa Xaa
1               5

( 2 ) INFORMATION FOR SEQ ID NO:95:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ95
            / note= "Xaa denotes V or I at residue #1; F, Y, I or L
            at residue #3; F, Y or I at residue #4; R or T at
            residue #6; and T or N at residue #8"

( x i ) SEQUENCE DESCRIPTION: SEQ ID NO:95:

Xaa Tyr Xaa Xaa Phe Xaa Xaa Xaa
1               5

( 2 ) INFORMATION FOR SEQ ID NO:96:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=SEQ96
        / note= "Xaa denotes V or I at residue #1; F, Y, I or L
        at residue #3; F, Y, I or L at residue #4; and T or N at
        residue #8"

( x i ) SEQUENCE DESCRIPTION: SEQ ID NO:96:

Xaa  Tyr  Xaa  Xaa  Phe  Arg  Xaa  Xaa
1                          5

( 2 ) INFORMATION FOR SEQ ID NO:97:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ97
            / note= "Xaa denotes F or Y at residue #2; F, Y or L
            at residue #3; F, Y, I or L at residue #4; F or Y at
            residue #5; R or T at residue #6; E, D, or V at residue
            # 7; and T or N at residue #8"

( x i ) SEQUENCE DESCRIPTION: SEQ ID NO:97:

Val  Xaa  Xaa  Xaa  Xaa  Xaa  Xaa  Xaa
1                          5

( 2 ) INFORMATION FOR SEQ ID NO:98:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ98
            / note= "Xaa denotes F or Y at residue #2; F, Y, I or L
            at residue #3; F, Y or I at residue #4; F or Y at
            residue #5; R or T at residue #6; E, D, or V at residue
            # 7; and T or N at residue #8"

( x i ) SEQUENCE DESCRIPTION: SEQ ID NO:98:

Val  Xaa  Xaa  Xaa  Xaa  Xaa  Xaa  Xaa
1                          5

( 2 ) INFORMATION FOR SEQ ID NO:99:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear (ii) MOLECULE TYPE: peptide (ix) FEATURE:
    (A) NAME/KEY: Peptide
    (B) LOCATION: 1..8
    (D) OTHER INFORMATION: /label=SEQ99
        / note= "Xaa denotes F or Y at residue #2; F, Y, I or L at residue #3; F, Y, I or L at residue #4; F or Y at residue #5; E, D, or V at residue #7; and T or N at residue #8"

(xi) SEQUENCE DESCRIPTION: SEQ ID NO:99:

Val Xaa Xaa Xaa Xaa Arg Xaa Xaa
1                           5

(2) INFORMATION FOR SEQ ID NO:100:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label=SEQ100
            / note= "Xaa denotes F or Y at residue #2; F, Y, I or L at residue #3; F, Y, I or L at residue #4; F or Y at residue #5; R or T at residue #6; E, D, or V at residue #7; and T or N at residue #8"

(xi) SEQUENCE DESCRIPTION: SEQ ID NO:100:

Val Xaa Xaa Xaa Xaa Xaa Xaa Xaa
1                           5

SEMAPHORIN GENE FAMILY

The research carried out in the subject application was supported in part by grants from the National Institutes of Health. The government may have rights in any patent issuing on this application.

INTRODUCTION

1. Technical Field

The technical field of this invention concerns peptides, polypeptides, and polynucleotides involved in nerve cell growth.

1. Background

The specificity of the wiring of the nervous system—the complex pattern of specific synaptic connections—begins to unfold during development as the growing tips of neurons—the growth cones—traverse long distances to find their correct targets. Along their journey, they are confronted by and correctly navigate a series of choice points in a remarkably unerring way to ultimately contact and recognize their correct target.

The identification of growth cone guidance cues is to a large extent, the holy grail of neurobiology. These are the compounds that tell neurons when to grow, where to grow, and when to stop growing. The medical applications of such compounds and their antagonists are enormous and include modulating neuronal growth regenerative capacity, treating neurodegenerative disease, and mapping (e.g. diagnosing) genetic neurological defects.

Over decades of concentrated research, various hypotheses of chemo-attractants and repellant, labeled pathways, cell adhesion molecules, etc. have been evoked to explain guidance. Recently, several recent lines of experiments suggest repulsion may play an important role in neuron guidance and two apparently unrelated factors ("Neurite Growth Inhibitor" and "Collapsin") capable of inhibiting or collapsing growth cones have been reported.

Relevant Literature

For a recent review of much of the literature in this field, see Goodman and Shatz (1993) Cell 72/Neuron 10, 77–98. A description of grasshopper fasciclin IV (now called G-Semaphorin I) appears in Kolodkin et al. (1992) Neuron 9,831–845. Recent reports on Collapsin and Neurite Growth Inhibitor include Raper and Kapfhammer (1990) Neuron 4, 21–29, an abstract presented by Raper at the GIBCO-BRL Symposium on "Genes and Development/Function of Brain" on Jul. 26, 1993 and Schwab and Caroni (1988) J Neurosci 8, 2381 and Schnell and Schwab (1990) Nature 343, 269, respectively.

SUMMARY OF THE INVENTION

A novel class of proteins, semaphorins, nucleic acids encoding semaphorins, and methods of using semaphorins and semaphorin-encoding nucleic acids are disclosed. Semaphorins include the first known family of human proteins which function as growth cone inhibitors and a family of proteins involved in viral, particularly pox viral, pathogenesis and oncogenesis. Families of semaphorin-specific receptors, including receptors found on nerve growth cones and immune cells are also disclosed.

The invention provides agents, including semaphorin peptides, which specifically bind semaphorin receptors and agents, including semaphorin receptor peptides, which specifically bind semaphorins. These agents provide potent modulators of nerve cell growth, immune responsiveness and viral pathogenesis and find use in the treatment and diagnosis of neurological disease and neuro-regeneration, immune modulation including hypersensitivity and graft-rejection, and diagnosis and treatment of viral and oncological infection/diseases.

Semaphorins, semaphorin receptors, semaphorin-encoding nucleic acids, and unique portions thereof also find use variously in screening chemical libraries for regulators of semaphorin or semaphorin receptor-mediated cell activity, in genetic mapping, as probes for related genes, as diagnostic reagents for genetic neurological, immunological and oncological disease and in the production of specific cellular and animal systems for the development of neurological, immunological, oncological and viral disease therapy.

DESCRIPTION OF SPECIFIC EMBODIMENTS

The present invention discloses novel families of proteins important in nerve and immune cell function: the semaphorins and the semaphorin receptors. The invention provides agents, including semaphorin peptides, which specifically bind semaphorin receptors and agents, including semaphorin receptor peptides, which specifically bind semaphorins. These agents find a wide variety of clinical, therapeutic and research uses, especially agents which modulate nerve and/or immune cell function by specifically mimicing or interfering with semaphorin-receptor binding. For example, selected semaphorin peptides shown to act as semaphorin receptor antagonists are effective by competitively inhibiting native semaphorin association with cellular receptors. Thus, depending on the targeted receptor, these agents can be used to block semaphorin mediated neural cell growth cone repulsion or contact inhibition. Such agents find broad clinical application where nerve cell growth is indicated, e.g. traumatic injury to nerve cells, neurodegenerative disease, etc. A wide variety of semaphorin- and semaphorin receptor-specific binding agents and methods for identifying, making and using the same are described below.

Binding agents of particular interest are semaphorin peptides which specifically bind and antagonize a semaphorin receptor and semaphorin receptor peptides which specifically bind a semaphorin and prevent binding to a native receptor. While exemplified primarily with semaphorin peptides, much of the following description applies analogously to semaphorin receptor peptides.

The semaphorin peptides of the invention comprise a unique portion of a semaphorin and have semaphorin binding specificity. A "unique portion" of a semaphorin has an amino acid sequence unique to that disclosed in that it is not found in any previously known protein. Thus a unique portion has an amino acid sequence length at least long enough to define a novel peptide. Unique semaphorin portions are found to vary from about 5 to about 25 residues, preferably from 5 to 10 residues in length, depending on the particular amino acid sequence. Unique semaphorin portions are readily identified by comparing the subject semaphorin portion sequences with known peptide/protein sequence data bases. Preferred unique portions derive from the semaphorin domains (which exclude the Ig-like, intracellular and transmembrane domains as well as the signal sequences) of the disclosed semaphorin sequences, especially regions that bind the semaphorin receptor, especially that of the human varieties. Preferred semaphorin receptor unique portions derive from the semaphorin binding domains, especially regions with residues which contact the semaphorin ligand, especially that of the human varieties. Particular preferred peptides are further described herein.

The subject peptides may be free or coupled to other atoms or molecules. Frequently the peptides are present as a portion of a larger polypeptide comprising the subject peptide where the remainder of the polypeptide need not be semaphorin or semaphorin receptor-derived. Alternatively, the subject peptide may be present as a portion of a "substantially full-length" semaphorin domain or semaphorin receptor sequence which comprises or encodes at least about 200, preferably at least about 250, more preferably at least about 300 amino acids of a disclosed semaphorin/receptor sequence. Thus the invention also provides polypeptides comprising a sequence substantially similar to that of a substantially full-length semaphorin domain or a semaphorin receptor. "Substantially similar" sequences share at least about 40%, more preferably at east about 60%, and most preferably at least about 80% sequence identity. Where the sequences diverge, the differences are generally point insertions/deletions or conservative substitutions, i.e. a cysteine/threonine or serine substitution, an acidic/acidic or hydrophobic/hydrophobic amino acid substitution, etc.

The subject semaphorin peptides/polypeptides are "isolated", meaning unaccompanied by at least some of the material with which they are associated in their natural state. Generally, an isolated peptide/polypeptide constitutes at least about 1%, preferably at least about 10%, and more preferably at least about 50% by weight of the total peptide/protein in a given sample. By pure peptide/polypeptide is intended at least about 90%, preferably at least 95%, and more preferably at least about 99% by weight of total peptide/protein. Included in the subject peptide/polypeptide weight are any atoms, molecules, groups, or polymers covalently coupled to the subject semaphorin/receptor peptide/polypeptide, especially peptides, proteins, detectable labels, glycosylations, phosphorylations, etc.

The subject peptides/polypeptides may be isolated or purified in a variety of ways known to those skilled in the art depending on what other components are present in the sample and to what, if anything, the peptide/polypeptide is covalently linked. Purification methods include electrophoretic, molecular, immunological and chromatographic techniques, especially affinity chromatography and RP-HPLC in the case peptides. For general guidance in suitable purification techniques, see Scopes, R., Protein Purification, Springer-Verlag, N.Y. (1982).

The subject peptides/polypeptides generally comprise naturally occurring amino acids but D-amino acids or amino acid mimetics coupled by peptide bonds or peptide bond mimetics may also be used. Amino acid mimetics are other than naturally occurring amino acids that conformationally mimic the amino acid for the purpose of the requisite semaphorin/receptor binding specificity. Suitable mimetics are known to those of ordinary skill in the art and include β-γ-δ amino and imino acids, cyclohexylalanine, adamantylacetic acid, etc., modifications of the amide nitrogen, the α-carbon, amide carbonyl, backbone modifications, etc. See, generally, Morgan and Gainor (1989) Ann. Repts. Med. Chem 24, 243–252; Spatola (1983) Chemistry and Biochemistry of Amino Acids, Peptides and Proteins, Vol VII (Weinstein) and Cho et. al (1993) Science 261, 1303–1305 for the synthesis and screening of oligocarbamates.

The subject semaphorin peptides/polypeptides have a "semaphorin binding specificity" meaning that the subject peptide/polypeptide retains a molecular conformation specific to one or more of the disclosed semaphorins and specifically recognizable by a semaphorin-specific receptor, antibody, etc. As such, a semaphorin binding specificity may be provided by a semaphorin-specific immunological epitope, lectin binding site, etc., and preferably, a receptor binding site. Analogously, the semaphorin receptor peptides/polypeptides have a "semaphorin receptor binding specificity" meaning that these peptides/polypeptides retain a molecular conformation specific to one or more of the disclosed semaphorin receptors and specifically recognizable by a semaphorin, a receptor-specific antibody, etc.

"Specific binding" is empirically determined by contacting, for example a semaphorin-derived peptide with a mixture of components and identifying those components that preferentially bind the semaphorin. Specific binding is most conveniently shown by competition with labeled ligand using recombinant semaphorin peptide either in vitro or in cellular expression systems as disclosed herein. Generally, specific binding of the subject semaphorin has binding affinity of $10^{-6}$M, preferably $10^{-8}$M, more preferably $10^{-10}$M, under in vitro conditions as exemplified below.

The peptides/polypeptides may be modified or joined to other compounds using physical, chemical, and molecular techniques disclosed or cited herein or otherwise known to those skilled in the relevant art to affect their semaphorin binding specificity or other properties such as solubility, membrane transportability, stability, binding specificity and affinity, chemical reactivity, toxicity, bioavailability, localization, detectability, in vivo half-life, etc. as assayed by methods disclosed herein or otherwise known to those of ordinary skill in the art. For example, point mutations are introduced by site directed mutagenesis of nucleotides in the DNA encoding the disclosed semaphorin polypeptides or in the course of in vitro peptide synthesis.

Other modifications to further modulate binding specificity/affinity include chemical/enzymatic intervention (e.g. fatty acid-acylation, proteolysis, glycosylation) and especially where the peptide/polypeptide is integrated into a larger polypeptide, selection of a particular expression host, etc. In particular, many of the disclosed semaphorin peptides contain serine and threonine residues which are phosphorylated or dephosphorylated. See e.g. methods disclosed in Roberts et al. (1991) Science 253, 1022–1026 and in Wegner et al. (1992) Science 256, 370–373. Amino and/or carboxyl termini may be functionalized e.g., for the amino group, acylation or alkylation, and for the carboxyl group, esterification or amidification, or the like. Many of the disclosed semaphorin peptides/polypeptides also contain glycosylation sites and patterns which may disrupted or modified, e.g. by enzymes like glycosidases or used to purify/identify the receptor, e.g. with lectins. For instance, N or O-linked glycosylation sites of the disclosed semaphorin peptides may be deleted or substituted for by another basic amino acid such as Lys or His for N-linked glycosylation alterations, or deletions or polar substitutions are introduced at Ser and Thr residues for modulating O-linked glycosylation. Glycosylation variants are also produced by selecting appropriate host cells, e.g. yeast, insect, or various mammalian cells, or by in vitro methods such as neuraminidase digestion. Useful expression systems include COS-7, 293, BHK, CHO, TM4, CV1, VERO-76, HELA, MDCK, BRL 3A, W138, Hep G2, MMT 060562, TRI cells, baculovirus systems, for examples. Other covalent modifications of the disclosed semaphorin peptides/polypeptides may be introduced by reacting the targeted amino acid residues with an organic derivatizing (e.g. methyl-3-[(p-azido-phenyl)dithio] propioimidate) or crosslinking agent (e.g. 1,1-bis (diazoacetyl)-2-phenylethane) capable of reacting with selected side chains or termini. For therapeutic and diagnostic localization, semaphorins and peptides thereof may be labeled directly (radioisotopes, fluorescers, etc.) or indirectly with an agent capable of providing a detectable signal, for example, a heart muscle kinase labeling site.

The following are 14 classes of preferred semaphorin peptides where bracketed positions may be occupied by any one of the residues contained in the brackets and "Xaa" signifies that the position may be occupied by any one of the 20 naturally encoded amino acids (see, Table 1). These enumerated peptides maintain highly conserved structures which provide important semaphorin binding specificities;

(a) [AspGlu]Cys[GlnLysArgAlaAsn]Asn[TyrPheVal]Ile (SEQ ID NO:1) Cys[GlnLysArgAlaAsn]Asn[TryrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3) CysGlyThr[AsnGly][AlaSerAsn]XaaXaaPro (SEQ ID NO:4) CysGlyThr[AsnGly]XaaXaaXaaProXaa[CysAsp] (SEQ ID NO:5) CysGlyThrXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7) [CysSer]Pro[PheTyr][AspAsn]Pro[AspGluArgLys][HisLeuAsp] (SEQ ID NO:8) GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10) Leu[PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]ArgGlu (SEQ ID NO:18) [PheTyr]PhePhe[PheTyr]ArgGlu (SEQ ID NO:19) [PheTyr][PheTyr][PheTyr]ArgGlu[ThrAsn]Ala (SEQ ID NO:20) [IleVal][PheTyr]Phe[PheTyr][PheTyr]ArgGlu (SEQ ID NO:21) Asp[LysPheTyr]Val[PheTyr][PheTyrIleLeu][PheTyrIleLeu][PheTyr] (SEQ ID NO:22) [ValIle][PheTyr][PheTyrIleLeu][PheTyrIleLeu]Phe[ArgThr]Xaa[ThrAsn] (SEQ ID NO:23) ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle]CysXaaXaaAsp (SEQ ID NO:28) GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30) [PheTyr]Leu[LysArg][AlaSer]ArgLeu[AsnIle]Cys (SEQ ID NO:31) [AsnIle]CysSer[IleVal][ProSer]Gly (SEQ ID NO:32) Trp[ThrAlaSer][ThrAlaSer][PheTyrLeu]LeuLys[AlaSerValIleLeu]XaaLeu (SEQ ID NO:33) Trp[ThrAlaSer][ThrAlaSer]XaaLeuLysXaaXaaLeuXaaCys (SEQ ID NO:34) TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle]ProXaaPro[ArgAla]ProGlyXaaCys (SEQ ID NO:42) Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51) CysXaaXaaCysXaaXaaAspXaaXaaCysXaaTrpAsp (SEQ ID NO:52)

The following peptides represent particularly preferred members of each class:

(a) AspCysGlnAsnTyrIle (SEQ ID NO:67)

(b) CysGlyThr[AsnGly][AlaSer]XaaXaaPro (SEQ ID NO:68)

(c) GlyXaa[SerCys]ProTyrAspPro (SEQ ID NO:69)

(d) LeuTyrSerGlyThr[ValAsnAla]Ala (SEQ ID NO:70)

(e) LeuAsnAlaProAsnPheVal (SEQ ID NO:71)

(f) [PheTyr]PhePhe[PheTyr]ArgGlu (SEQ ID NO:19)

(g) Glu[PheTyr]IleAsn[CysSer]GlyLys (SEQ ID NO:25)

(h) Arg[ValIle]AlaArgValCysLys (SEQ ID NO:72)

(i) Trp[ThrAla][ThrSer][PheTyr]LeuLys[AlaSer]ArgLeu (SEQ ID NO:73)

(j) ProPheTyrPhe[AsnAsp]GluIleGlnSer (SEQ ID NO:74)

(k) GlySerAlaValCysXaa[PheTyr] (SEQ ID NO:75)

(l) AsnSerAsnTrpLeu[ProAla]Val (SEQ ID NO:76)

(m) Pro[GluAsp]ProArgProGly[ThrGlnSer]Cys (SEQ ID NO:77)

(n) AspProTyrCys[AlaGly]TrpAsp (SEQ ID NO:78)

The following 14 classes are preferred peptides which exclude semaphorin peptides encoded in open reading flames of Varioia major or Vaccinia viruses.

(a) [AspGlu]Cys[GlnLysArgAlaAsn]Asn[TyrPheVal]Ile (SEQ ID NO:01) Cys[GlnLysArgAlaAsn]Asn[TyrPheVal]Ile[ArgLysGlnThr] (SEQ ID NO:02)

(b) CysGlyThr[AsnGly][AlaSer][TyrPheHisGly][LysArgHisAsnGln] (SEQ ID NO:79) CysGlyThr[AsnGly][AlaSerAsn][TyrPheHis][LysArgHisAsnGln] (SEQ ID NO:80) CysGlyThr[AsnGly][AlaSer]XaaXaaPro (SEQ ID NO:81)

(c) [ArgIleGlnVal][GlyAla][LeuValLys][CysSer]Pro[PheTyr][AspAsn] (SEQ ID NO:07) [CysSer]Pro[PheTyr][AspAsn]Pro[AspGluArgLys][HisLeuAsp] (SEQ ID NO:08) GlyXaa[GlyAla]Xaa[CysSer]ProTyr[AspAsn]Pro (SEQ ID NO:09)

(d) Leu[PheTyr]Ser[GlyAla]Thr[ValAsnAla]Ala (SEQ ID NO:10) Leu[PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]

ArgGlu (SEQ ID NO:18) [PheTyr]PhePhe[PheTyr]
ArgGlu (SEQ ID NO:19) [PheTyr][PheTyr][PheTyr]
ArgGlu[ThrAsn]Ala (SEQ ID NO:20) [IleVal][PheTyr]
Phe[PheTyr][PheTyr]ArgGlu (SEQ ID NO:21) Asp
[LysPheTyr]Val[PheTyr][PheTyrLeu][PheTyrIleLeu]
[PheTyr] (SEQ ID NO:22) Asp[LysPheTyr]Val
[PheTyr][PheTyrIleLeu][PheTyrIle][PheTyr] (SEQ ID
NO:82) [ValIle][PheTyr][PheTyrLeu][PheTyrIleLeu]
Phe[ArgThr]Xaa[ThrAsn] (SEQ ID NO:83) [ValIle]
[PheTyr][PheTyrIleLeu][PheTyrIle]Phe[ArgThr]Xaa
[ThrAsn] (SEQ ID NO:84) [ValIle][PheTyr]
[PheTyrIleLeu][PheTyrIleLeu]PheArgXaa[ThrAsn]
(SEQ ID NO:85) [ValIle][PheTyr][PheTyrLeu]
[PheTyrIleLeu][PheTyr][ArgThr][GluAspVal]
[ThrAsn] (SEQ ID NO:86)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly[]ArgGln[ValIle]CysLys (SEQ ID NO:27) Arg[ValIle]Xaa[ArgGln][ValIle] CysXaaXaaAsp (SEQ ID NO:28) GlyLys[ValAlaIle] XaaXaaXaaArg[ValAlaIle]XaaXaaXaaCysLys (SEQ ID NO:29)

(i) [ArgLysAsn]Trp[ThrAla][ThrAlaSer][PheTyrLeu]Leu [LysArg] (SEQ ID NO:87) [PheTyr]Leu[LysArg] [AlaSer]ArgLeu[AsnIle]Cys (SEQ ID NO:31) [AsnIle] CysSer[IleVal][ProSer]Gly (SEQ ID NO:32) Trp [ThrAla][ThrAlaSer][PheTyrLeu]LeuLys [AlaSerValIleLeu]XaaLeu (SEQ ID NO:88) Trp [ThrAlaSer][ThrAlaSer][PheTyrLeu]LeuLys [AlaSerIleLeu]XaaLeu (SEQ ID NO:89) Trp[ThrAla] [ThrAlaSer]XaaLeuLysXaaXaaLeuXaaCys (SEQ ID NO:90)

(j) [PheTyr][PheTyr][AsnAsp]GluIleGlnSer (SEQ ID NO:36) [PheTyr]Pro[PheTyr][PheTyr][PheTyr] [AsnAsp]Glu (SEQ ID NO:37)

(k) GlySerAla[ValIleLeu]CysXaa[PheTyr] (SEQ ID NO:38) SerAla[ValIle]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle] ProXaaProArgProGlyXaaCys (SEQ ID NO:91) Pro [GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51) CysXaaXaaCysXaaXaaAspXaaXaaCysXaaTrpAsp (SEQ ID NO:52)

The following 2 classes are preferred peptides which exclude semaphorin peptides encoded in open reading frames of Variola major or Vaccinia viruses Grasshopper Semaphofin I.

(f) TyrPhePhe[PheTyr]ArgGlu (SEQ ID NO:18) Asp [LysTyr]Val[PheTyr][PheTyrLeu][PheTyrIleLeu] [PheTyr] (SEQ ID NO:92) Asp[LysTyr]Val[PheTyr] [PheTyrIleLeu][PheTyrIle][PheTyr] (SEQ ID NO:93) [ValIle]Tyr[PheTyrLeu][PheTyrIleLeu]Phe[ArgThr] Xaa[ThrAsn] (SEQ ID NO:94) [ValIle]Tyr [PheTyrIleLeu][PheTyrIle]Phe[ArgThr]Xaa[ThrAsn] (SEQ ID NO:95) [ValIle]Tyr[PheTyrIleLeu] [PheTyrIleLeu]PheArgXaa[ThrAsn] (SEQ ID NO:96) Val[PheTyr][PheTyrLeu][PheTyrIleLeu[]PheTyr[] ArgThr[]GluAspVal][ThrAsn] (SEQ ID NO:97) Val [PheTyr][PheTyrIleLeu][PheTyrIle][PheTyr][ArgThr] [GluAspVal][ThrAsn] (SEQ ID NO:98) Val[PheTyr] [PheTyrIleLeu][PheTyrIleLeu][PheTyr]Arg [GluAspVal][ThrAsn] (SEQ ID NO:99)

(n) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaAspXaaXaaCysXaaTrpAsp (SEQ ID NO:51) CysXaaXaaCysXaaXaaAspXaaXaaCysXaaTrpAsp (SEQ ID NO:52)

The following 5 classes include peptides which encompass peptides encoded in open reading frames of Variola major or Vaccinia viruses. Accordingly, in the event that these vital peptides are not novel per se, the present invention discloses a hitherto unforseen and unforseeable utility for these peptides as immunosuppressants and targets of anti-viral therapy.

(b) CysGlyThr[AsnGly][AlaSerAsn][TyrPheHisGly] [LysArgHisAsnGln] (SEQ ID NO:03) CysGlyThr [AsnGly][AlaSerAsn]XaaXaaPro (SEQ ID NO:04) CysGlyThr[AsnGly]XaaXaaXaaProXaa[CysAsp] (SEQ ID NO:05) CysGlyThrXaaXaaXaaXaaProXaa [CysAsp]XaaXaa[TyrIle] (SEQ ID NO:06)

(f) Asp[LysPheTyr]Val[PheTyr][PheTyrIleLeu] [PheTyrIleLeu][PheTyr] (SEQ ID NO:22) [ValIle] [PheTyr][PheTyrIleLeu][PheTyrIleLeu]Phe[ArgThr] Xaa[ThrAsn] (SEQ ID NO:23) Val[PheTyr] [PheTyrIleLeu][PheTyrIleLeu][PheTyr][ArgThr] [GluAspVal][ThrAsn] (SEQ ID NO:100)

(i) [ArgLysAsn]Trp[ThrAlaSer][ThrAlaSer][PheTyrLeu] Leu[LysArg] (SEQ ID NO:30) Trp[ThrAlaSer] [ThrAlaSer][PheTyrLeu]LeuLys[AlaSerValIleLeu] XaaLeu (SEQ ID NO:33) Trp[ThrAlaSer][ThrAlaSer] XaaLeuLysXaaXaaLeuXaaCys (SEQ ID NO:34) TrpXaa[ThrSer]XaaLeuLysXaaXaaLeuXaaCys (SEQ ID NO:35)

(k) SerAla[ValIleLeu]CysXaa[PheTyr]XaaMet (SEQ ID NO:39)

(m) [ValLeuIle]ProXaaPro[ArgAla]ProGlyXaaCys (SEQ ID NO:42)

The disclosed semaphorin sequence data are used to define a wide variety of other semaphorin- and semaphorin receptor-specific binding agents using immunologic, chromatographic or synthetic methods available to those skilled in the art.

Of particular significance are peptides comprising unique portions of semaphorin-specific receptors and polypeptides comprising a sequence substantially similar to that of a substantially full-length semaphorin receptor. Using semaphorin peptides, these receptors are identified by a variety of techniques known to those skilled in the art where a ligand to the target receptor is known, including expression cloning as set out in the exemplification below. For other examples of receptor isolation with known ligand using expression cloning, see, Staunton et al (1989) Nature 339, 61; Davis et al (1991) Science 253, 59; Lin et al (1992) Cell 68, 775; Gearing et al (1989) EMBO 8, 3667; Aruffo and Seed (1987) PNAS 84, 8573 and references therein. Generally, COS cells are transfected to express a cDNA library or PCR product and cells producing peptides/polypeptides which bind a semaphorin/receptor peptide/polypeptide are isolated. For neurosemaphorin receptors, fetal brain cDNA libraries are preferred; for immunosemaphorin receptors, libraries derived from activated lymphoid or myeloid cell lines or tissue derived from sites of inflammation or delayed-type hypersensitivity are preferred; and for semaphorin and semaphorin receptor variants used by tumor cells to evade immune surveillance or suppress an immune response (oncosemaphorins), libraries derived from cancerous tissue or tumor cell lines resistant to the host immune system are preferred. Alternatively, PCR primers based upon known semaphorin/receptor sequences such as those disclosed herein are used to amplify PCR product from such tissues/ cells. Other receptor/ligand isolation methods using immobilized ligand or antibody are known to those skilled in the art.

Semaphorin receptor peptides with receptor binding specificity are identified by a variety of ways including having conserved consensus sequences with other semaphorin receptors, by crosslinking to ligand or receptor-specific antibody, or preferably, by screening such peptides for semaphorin binding or disruption of semaphorin-receptor binding. Methods for identifying semaphorin receptor peptides with the requisite binding activity are described herein or otherwise known to those skilled in the art. By analogous methods, semaphorin receptor peptides are used to define additional semaphorin peptides with semaphorin binding specificity, particularly receptor specificity.

The various semaphorin and semaphorin receptor peptides are used to define functional domains of semaphorins, identify compounds that associate with semaphorins, design compounds capable of modulating semaphorin-mediated nerve and immune cell function, and define additional semaphorin and semaphorin receptor-specific binding agents. For example, semaphorin mutants, including deletion mutants are generated from the disclosed semaphorin sequences and used to identify regions important for specific protein-ligand or protein-protein interactions, for example, by assaying for the ability to mediate repulsion or preclude aggregation in cell-based assays as described herein. Further, x-ray crystallographic data of the disclosed protein are used to rationally design binding molecules of determined structure or complementarity for modulating growth cone growth and guidance.

Additional semaphorin- and receptor-specific agents include specific antibodies that can be modified to a monovalent form, such as Fab, Fab', or Fv, specifically binding oligopeptides or oligonucleotides and most preferably, small molecular weight organic receptor antagonists. For example, the disclosed semaphorin and receptor peptides are used as immunogens to generate semaphorin- and receptor-specific polyclonal or monoclonal antibodies. See, Harlow and Lane (1988) Antibodies, A Laboratory Manual, Cold Spring Harbor Laboratory, for general methods. Anti-idiotypic antibody, especially internal imaging anti-ids are also prepared using the disclosures herein.

In addition to semaphorin and semaphorin-receptor derived polypeptides and peptides, other prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful agents are identified with a range of assays employing a compound comprising the subject peptides or encoding nucleic acids. A wide variety of in vitro, cell-free binding assays, especially assays for specific binding to immobilized compounds comprising semaphorin or semaphorin receptor peptide find convenient use. While less preferred, cell-based assays may be used to determine specific effects of prospective agents on semaphorin-receptor binding may be assayed. Optionally, the intracellular C-terminal domain is substituted with a sequence encoding a oligopeptide or polypeptide domain that provides a detectable intracellular signal upon ligand binding different from the natural receptor. Useful intracellular domains include those of the human insulin receptor and the TCR, especially domains with kinase activity and domains capable of triggering calcium influx which is conveniently detected by fluorimetry by preloading the host cells with Fura-2. More preferred assays involve simple cell-free in vitro binding of candidate agents to immobilized semaphorin or receptor peptides, or vice versa. See, e.g. Fodor et al (1991) Science 251, 767 for light directed parallel synthesis method. Such assays are amenable to scale-up, high throughput usage suitable for volume drug screening.

Useful agents are typically those that bind to a semaphorin or disrupt the association of a semaphorin with its receptor. Preferred agents are semaphorin-specific and do not cross react with other neural or lymphoid cell membrane proteins. Useful agents may be found within numerous chemical classes, though typically they are organic compounds; preferably small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways as described above, e.g. to enhance their proteolytic stability. Other methods of stabilization may include encapsulation, for example, in liposomes, etc.

The subject binding agents may be prepared in a variety of ways known to those skilled in the art. For example, peptides under about 60 amino acids can be readily synthesized today using conventional commercially available automatic synthesizers. Alternatively, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. If desired, the open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

For therapeutic uses, the compositions and agents disclosed herein may be administered by any convenient way, preferably parenterally, conveniently in a pharmaceutically or physiologically acceptable carrier, e.g., phosphate buffered saline, saline, deionized water, or the like. Typically, the compositions are added to a retained physiological fluid such as blood or synovial fluid. For CNS administration, a variety of techniques are available for promoting transfer of the therapeutic across the blood brain barrier including disruption by surgery or injection, drugs which transciently open adhesion contact between CNS vasculature endothelial cells, and compounds which fascilitate translocation through such cells. As examples, many of the disclosed therapeutics are amenable to directly injected or infused, contained within implants e.g. osmotic pumps, grafts comprising appropriately transformed cells. Generally, the amount administered will be empirically determined, typically in the range of about 10 to 1000 μg/kg of the recipient. For peptide agents, the concentration will generally be in the range of about 50 to 500 μg/ml in the dose administered. Other additives may be included, such as stabilizers, bactericides, etc. These additives will be present in conventional amounts.

The invention provides isolated nucleic acid sequences encoding the disclosed semaphorin and semaphorin receptor peptides and polypeptides, including sequences substantially identical to sequences encoding such polypeptides. An "isolated" nucleic acid sequence is present as other than a naturally occurring chromosome or transcript in its natural state and typically is removed from at least some of the nucleotide sequences with which it is normally associated with on a natural chromosome. A complementary sequence hybridizes to a unique portion of the disclosed semaphorin sequence under low stringency conditions, for example, at 50° C. and SSC (0.9M saline/0.09M sodium citrate) and that remains bound when subject to washing at 55° C. with SSC. Regions of non-identity of complementary nucleic acids are preferably or in the case of homologous nucleic acids, a nucleotide change providing a redundant codon. A partially pure nucleotide sequence constitutes at least about 5%, preferably at least about 30%, and more preferably at least about 90% by weight of total nucleic acid present in a given fraction.

Unique portions of the disclosed nucleic acid sequence are of length sufficient to distinguish previously known nucleic acid sequences. Thus, a unique portion has a nucleotide sequence at least long enough to define a novel oligonucleotide. Preferred nucleic acid portions encode a unique semaphorin peptide. The nucleic acids of the invention and portions thereof, other than those used as PCR primers, are usually at least about 60 bp and usually less than about 60 kb in length. PCR primers are generally between about 15 and 100 nucleotides in length.

Nucleotide (cDNA) sequences encoding several full length semaphorins are disclosed herein. The invention also provides for the disclosed sequences modified by transitions, transversions, deletions, insertions, or other modifications such as alternative splicing and also provides for genomic semaphorin sequences, and gene flanking sequences, including regulatory sequences; included are DNA and RNA sequences, sense and antisense. Preferred DNA sequence portions include portions encoding the preferred amino acid sequence portions disclosed above. For antisense applications where the inhibition of semaphorin expression is indicated, especially useful oligonucleotides are between about 10 and 30 nucleotides in length and include sequences surrounding the disclosed ATG start site, especially the oligonucleotides defined by the disclosed sequence beginning about 5 nucleotides before the start site and ending about 10 nucleotides after the disclosed start site. Other especially useful semaphorin routants involve deletion or substitution modifications of the disclosed cytoplasmic C-termini of transmembrane semaphorins. Accordingly, semaphorin routants with semaphorin binding affinities but with altered intracellular signal transduction capacities are produced.

For modified semaphorin-encoding sequences or related sequences encoding proteins with semaphorin-like functions, there will generally be substantial sequence identity between at least a segment thereof and a segment encoding at least a portion of the disclosed semaphorin sequence, preferably at least about 60%, more preferably at least 80%, most preferably at least 90% identity. Homologous segments are particularly within semaphorin domain-encoding regions and regions encoding protein domains involved in protein-protein, particularly semaphorin-receptor interactions and differences within such segments are particularly conservative substitutions.

Typically, the invention's semaphorin peptide encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein. According to a particular embodiment of the invention, portions of the semaphorin encoding sequence are spliced with heterologous sequences to produce soluble, secreted fusion proteins, using appropriate signal sequences and optionally, a fusion partner such as β-Gal.

The disclosed sequences are also used to identify and isolate other natural semaphorins and analogs. In particular, the disclosed nucleic acid sequences are used as hybridization probes under low-stringency or PCR primers, e.g. oligonucleotides encoding functional semaphorin domains are $^{32}$P-labeled and used to screen λcDNA libraries at low stringency to identify similar cDNAs that encode proteins with related functional domains. Additionally, nucleic acids encoding at least a portion of the disclosed semaphorin are used to characterize tissue specific expression of semaphorin as well as changes of expression over time, particularly during organismal development or cellular differentiation.

The semaphorin encoding nucleic acids can be subject to alternative purification, synthesis, modification, sequencing, expression, transfection, administration or other use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y. 1992) or that are otherwise known in the art. For example, the nucleic acids can be modified to alter stability, solubility, binding affinity and specificity, etc. semaphorin-encoding sequences can be selectively methylated, etc. The nucleic acid sequences of the present invention may also be modified with a label capable of providing a detectable signal, either directly or indirectly. Exemplary labels include radioisotopes, fluorescers, biotinylation, etc.

The invention also provides vectors comprising nucleic acids encoding semaphorin peptides, polypeptides or analogs. A large number of vectors, including plasmid and viral vectors, have been described for expression in a variety of eukaryotic and prokaryotic hosts. Advantageously, vectors may also include a promotor operably linked to the semaphorin-encoding portion. Vectors will often include one or more replication systems for cloning or expression, one or more markers for selection in the host, e.g. antibiotic resistance. The inserted semaphorin coding sequences may be synthesized, isolated from natural sources, prepared as hybrids, etc. Suitable host cells may be transformed/transfected/infected by any suitable method including electroporation, CaCl$^2$ mediated DNA uptake, viral infection, microinjection, microprojectile, or other methods.

Appropriate host cells include bacteria, archebacteria, fungi, especially yeast, and plant and animal cells, especially mammalian cells. Of particular interest are *E. coli, B. subtilis, Saccharomyces cerevisiae*, SF9 cells, C129 cells, 293 cells, Neurospora, and CHO, COS, HeLa cells, immortalized mammalian myeloid and lymphoid cell lines, and pluripotent cells, especially mammalian ES cells and zygotes. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced semaphorins or analogs.

For the production of stably transformed cells and transgenic animals, nucleic acids encoding the disclosed semaphorins may be integrated into a host genome by recombination events. For example, such a sequence can be microinjected into a cell, and thereby effect homologous recombination at the site of an endogenous gene, an analog or pseudogene thereof, or a sequence with substantial identity to an semaphorin-encoding gene. Other recombination-based methods such as nonhomologous recombinations, deletion of endogenous gene by homologous recombination, especially in pluripotent cells, etc., provide additional applications. Preferred transgenics and stable transformants overexpress the disclosed receptor gene and find use in drug development and as a disease model. Alternatively, knockout cells and animals find use in development and functional studies. Methods for making transgenic animals, usually rodents, from ES cells or zygotes are known to those skilled in the art.

The compositions and methods disclosed herein may be used to effect gene therapy. See, e.g. Zhu et al. (1993) Science 261, 209–211; Gutierrez et al. (1992) Lancet 339, 715–721. For example, cells are transfected with semaphorin sequences operably linked to gene regulatory sequences capable of effecting altered semaphorin expression or regulation. To modulate semaphorin translation, cells may be transfected with complementary antisense polynucleotides. For gene therapy involving the transfusion of semaphorin transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The following examples are offered by way of illustration and not by way of limitation.

EXAMPLES

I. Isolation and characterization of Grasshopper Semaphorin I (SEQ ID NOS:57 and 58:) (previously referred to as Fasciclin IV)

In order to identify cell surface molecules that function in selective fasciculation, a series of monoclonal antibody (MAb) screens was conducted. The immunogen used for most of these screens was membranes from the longitudinal connectives (the collection of longitudinal axons) between adjacent segmental ganglia of the nervous system of the larval grasshopper. From these screens, MAb 3B11 and 8C6 were used to purify and characterize two surface glycoproteins, fasciclin I and fasciclin II, see, Bastiani et al., 1987; the genes encoding both were subsequently cloned, see, Snow et al. 1989, Zinn et al. 1988, and Harrelson and Goodman, 1988.

Another MAb isolated during these screens, MAb 6F8, was chosen for the present study because, just as with fasciclin I and fasciclin II, the antigen recognized by this MAb is expressed on a different but overlapping subset of axon pathways in the developing CNS. The 6F8 antigen appears to be localized on the outside of cell surfaces, as indicated by MAb binding when incubated both in live preparations, and in fixed preparations in which no detergents have been added. Because the 6F8 antigen is a surface glycoprotein expressed on a subset of axon fasciclin (see below), we call it fasciclin IV.

Fasciclin IV expression begins early in embryonic development before axonogenesis. At 29% of development, expression is seen on the surface of the midline roesectodermal cells and around 5–7 neuroblasts and associated ectodermal cells per hemisegment. This expression is reminiscent of the mesectodermal and neuroblast-associated expression observed with both fasciclin I and fasciclin II; however, in each case, the pattern resolves into a different subset of neuroblasts and associated ectodermal cells.

At 32% of development, shortly after the onset of axonogenesis in the CNS, fasciclin IV expression is seen on the surface of the axons and cell bodies of the three pairs of MP4, MP5, and MP6 midline progeny, the three U motoneurons, and on several unidentified neurons in close proximity to the U's. This is in contrast to fasciclin II, which at this stage is expressed on the MP1 and dMP2 neurons, and fasciclin I, which is expressed on the U neurons but not on any midline precursor progeny.

The expression of fasciclin IV on a subset of axon pathways is best observed around 40% of development, after the establishment of the first longitudinal and commissural axon pathways. At this stage, the protein is expressed on two longitudinal axon fasciclin, a subset of commissural axon fasciclin, a tract extending anteriorly along the midline, and a subset of fasciclin in the segmental nerve (SN) and intersegmental nerve (ISN) roots.

Specifically, fasciclin IV is expressed on the U fascicle, a longitudinal pathway (between adjacent segmental neuromeres) pioneered in part by the U neurons, and on the A/P longitudinal fascicle (in part an extension of the U fascicle within each segmental neuromere). In addition, fasciclin IV is also expressed on a second narrower, medial, and more ventral longitudinal pathway. The U axons turn and exit the CNS as they pioneer the ISN; the U's and many other axons within the ISN express fasciclin IV. The continuation of the U fascicle posterior to the ISN junction is also fasciclin IV-positive. The specificity of fasciclin IV for distinct subsets of longitudinal pathways can be seen by comparing fasciclin IV and fasciclin II expression in the same embryo; fasciclin IV is expressed on the U and A/P pathways whereas fasciclin II is expressed on the MP1 pathway.

The axons in the median fiber tract (MFT) also express fasciclin IV. The MFT is pioneered by the three pairs of progeny of the midline precursors MP4, MP5, and MP6. The MFT actually contains three separate fasciclin. The axons of the two MP4 progeny pioneer the dorsal MFT fascicle and then bifurcate at the posterior end of the anterior commissure; whereas the axons of the two MP6 progeny pioneer the ventral MFT fascicle and then bifurcate at the anterior end of the posterior commissure. Fasciclin IV is expressed on the cell bodies of the six MP4, MP5, and MP6 neurons, and on their growth cones and axons as they extend anteriorly in the MFT and bifurcate in one of the two commissures. However, this expression is regional in that once these axons bifurcate and begin to extend laterally across the longitudinal pathways and towards the peripheral nerve roots, their expression of fasciclin IV greatly decreases. Thus, fasciclin IV is a label for the axons in the MFT and their initial bifurcations in both the anterior and posterior commissures. It appears to be expressed on other commissural fasciclin as well. However, the commissural expression of fasciclin IV is distinct from the transient expression of fasciclin II along the posterior edge of the posterior commissure, or the expression of fasciclin I on several different commissural axon fasciclin in both the anterior and posterior commissure (Bastiani et al., 1987; Harrelson and Goodman, 1988).

Fasciclin IV is also expressed on a subset of motor axons exiting the CNS in the SN. The SN splits into two major branches, one anterior and the other posterior, as it exits the CNS. Two large bundles of motoneuron axons in the anterior branch express fasciclin IV at high levels; one narrow bundle of motoneuron axons in the posterior branch expresses the protein at much lower levels. Fasciclin IV is also expressed on many of the axons in the ISN.

The CNS and nerve root expression patterns of fasciclin IV, fasciclin I, and fasciclin II at around 40% of embryonic development are summarized in. Although there is some overlap in their patterns (e.g., both fasciclin IV and fasciclin I label the U axons), these three surface glycoproteins label distinct subsets of axon pathways in the developing CNS. Fasciclin IV is expressed on epithelial bands in the developing limb bud Fasciclin IV is expressed on the developing limb bud epithelium in circumferential bands; at 34.5% of development these bands can be localized with respect to constrictions in the epithelium that mark presumptive segment boundaries. In addition to a band just distal to the trochanter/coxa segment boundary, bands are also found in the tibia, femur, coxa, and later in development a fifth band is found in the tarsus. Fasciclin IV is also expressed in the nascent chordotonal organ in the dorsal aspect of the femur. The bands in the tibia, trochanter, and coxa completely encircle the limb. However, the femoral band is incomplete, containing a gap on the anterior epithelia of this segment.

The position of the Ti1 axon pathway with respect to these bands of fasciclin IV-positive epithelia suggests a potential role for fasciclin IV in guiding the Ti1 growth cones. First, the band of fasciclin IV expression in the trochanter, which is approximately three epithelial cell diameters in width when encountered by the Ti1 growth cones, is the axial location where the growth cones reorient from proximal migration to circumferential branch extension. The Tr1 cell, which marks the location of the turn, lies within this band, usually over the central or the proximal cell tier. Secondly, although there is a more distal fasciclin IV expressing band in the femur, where a change in Ti1 growth is not observed, there exists a gap in this band such that fasciclin IV expressing cells are not traversed by the Ti1 growth cones. The Ti1 axons also may encounter a fasciclin IV expressing region within the coxa, where interactions between the growth cones, the epithelial cells, and the Cx1 guidepost cells have not yet been investigated.

In addition to its expression over the surface of bands of epithelial cells, fasciclin IV protein, as visualized with MAb 6F8, is also found on the basal surface of these cells in a punctate pattern. This punctate staining is not an artifact of the HRP immunocytochemistry since fluorescent visualization of MAb 6F8 is also punctate. The non-neuronal expression of fasciclin IV is not restricted to limb buds. Circumferential epithelial bands of fasciclin IV expression are also seen on subesophageal mandibular structures and on the developing antennae.

MAb directed against fasciclin IV can alter the formation of the Ti1 axon pathway in the limb bud The expression of fasciclin IV on an epithelial band at a key choice point in the formation of the Ti1 axon pathway led us to ask whether this protein is involved in growth cone guidance at this location. To answer this question, we cultured embryos, or epithelial fillets (e.g., O'Connor et al., 1990), during the 5% of development necessary for normal pathway formation, either in the presence or absence of MAb 6F8 or 6F8 Fab fragments. Under the culture conditions used for these experiments, defective Ti1 pathways are observed in 14% of limbs (Chang et al., 1992); this defines the baseline of abnormalities observed using these conditions. For controls we used other MAbs and their Fab fragments that either bind to the surfaces of these neurons and epithelial cells (MAb 3B11 against the surface protein fasciclin I) or do not (MAb 4D9 against the nuclear protein engrailed; Patel et al., 1989). To assess the impact of MAb 6F8 on Ti1 pathway formation, we compared the percentage of aberrant pathways observed following treatment with MAb 6F8 to that observed with MAbs 3B11 and 4D9. Our cultures began at 32% of development when the Ti1 growth cones have not yet reached the epithelium just distal to the trochanter/coxa boundary and therefore have not encountered epithelial cells expressing fasciclin IV. Following approximately 30 hours in culture (~4% of development), embryos were fixed and immunostained with antibodies to HRP in order to visualize the Ti1 axons and other neurons in the limb bud. Criteria for scoring the Ti1 pathway, and the definition of "aberrant", are described in detail in the Experimental Procedures.

Although MAb 6F8 does not arrest pathway formation, several types of distinctive, abnormal pathways are observed. These defects generally begin where growth cones first contact the fasciclin IV expressing cells in the trochanter. Normally, the Ti1 neurons each have a single axon, and the axons of the two cells are fasciculated in that portion of the pathway within the trochanter. Following treatment with MAb 6F8, multiple long axon branches are observed within, and proximal to, the trochanter. Two major classes of pathways are taken by these branches; in 36% of aberrant limbs, multiple, long axon branches extend ventrally in the region distal to the Cx1 cells which contains the band of fasciclin IV expressing epithelial cells. In the ventral region of the trochanter, these branches often independently turn proximally to contact the Cx1 cells, and thus complete the pathway in this region.

In the second major class of pathway defect, seen in 47% of aberrant limbs, axon branches leave the trochanter at abnormal, dorsal locations, and extend proximally across the trochanter/coxa boundary. These axons then veer ventrally, often contacting the Cx1 neurons. The remaining 17% of defects include defasciculation distal to the trochanter, axon branches that fail to turn proximally in the ventral trochanter and continue into the posterior compartment of the limb, and axon branches which cross the trochanter/coxa boundary and continue to extend proximally without a ventral turn.

When cultured in the presence of MAb 6F8, 43% of limbs exhibited malformed Ti1 pathways (n=381) as compared to 11% with MAb 3B11 (n=230) and 5% with MAb 4D9 (n=20). These percentages are pooled from treatments with MAbs concentrated from hybridoma supernatant, IgGs isolated from these supernatants, and Fab fragments isolated from these IgG preparations (see Experimental Procedures). The frequency of realformed Ti1 pathways and the types of defects observed showed no significant variation regardless of the method of antibody preparation or type of antibody used. Since Fabs show similar results as IgGs, the effects of MAb 6F8 are not due to cross linking by the bivalent IgG.

In summary, following treatment with MAb 6F8, the Ti1 pathway typically exhibits abnormal morphology beginning just distal to the trochanter and at the site of fasciclin IV expression. The two most common types of Ti1 pathway defects described above occur in 36% of experimental limbs (treated with MAb 6F8), but are seen in only 4% of control limbs (treated with MAbs 3 B11 and 4D9).

Fasciclin IV cDNAs encode a novel integral membrane protein

Grasshopper fasciclin IV was purified by passing crude embryonic grasshopper lysates over a MAb 6F8 column. After affinity purification, the protein was eluted, precipitated, denatured, modified at cysteines, and digested with either trypsin or Lys-C. Individual peptides were resolved by reverse phase HPLC and microsequenced using standard methods.

The amino acid sequences derived from these proteolytic fragments were used to generate oligonucleotide probes for PCR experiments, resulting in products that were used to isolate cDNA clones from the Zinn embryonic grasshopper cDNA library (Snow et al., 1988). Sequence analysis of these cDNAs reveals a single open reading frame (ORF) encoding a protein with two potential hydrophobic stretches of amino acids: an amino-terminal signal sequence of 20 residues and (beginning at amino acid 627) a potential transmembrane domain of 25 amino acids. Thus, the deduced protein has an extracellular domain of 605 amino acids, a transmembrane domain, and a cytoplasmic domain of 78 amino acids. The calculated molecular mass of the mature fasciclin IV protein is 80 kd and is confirmed by Western blot analysis of the affinity purified and endogenous protein as described below. The extracellular domain of the protein includes 16 cysteine residues that fall into three loose clusters but do not constitute a repeated domain and are not similar to other known motifs with cysteine repeats. There are also six potential sites for N-linked glycosylation in the extracellular domain. Treatment of affinity purified fasciclin IV with N-Glycanase demonstrates that fasciclin IV does indeed contain N-linked oligosaccharides. Fasciclin IV shows no sequence similarity when compared with other proteins in the PIR data base using BLASTP (Altschul et al., 1990), and is therefore a novel type I integral membrane protein.

A polyclonal antiserum directed against the cytoplasmic domain of the protein encoded by the fasciclin IV cDNA was used to stain grasshopper embryos at 40% of development. The observed staining pattern was identical to that seen with MAb 6F8. On Western blots, this antiserum recognizes the protein we affinity purified using MAb 6F8 and then subjected to microsequence analysis. Additionally, the polyclonal serum recognizes a protein of similar molecular mass from grasshopper embryonic membranes. Taken together these data indicate that the sequence we have obtained is indeed fasciclin IV.

Four other cell surface proteins that label subsets of axon pathways in the insect nervous system (fasciclin I, fasciclin II, fasciclin III, and neuroglian) are capable of mediating homophilic cell adhesion when transfected into S2 cells in vitro (Snow et al., 1989; Elkins et al., 1990b; Grenningloh et al., 1990). To ask whether fasciclin IV can function as a homophilic cell adhesion molecule, the fasciclin IV cDNA with the complete ORF was placed under the control of the inducible metallothionein promoter (Bunch et al., 1988), transfected into S2 cells, and assayed for its ability to promote adhesion in normally non-adhesive S2 cells. Following induction with copper, fasciclin IV was synthesized in these S2 cells as shown by Western blot analysis and cell surface staining of induced S2 cells with the polyclonal antiserum described above.

We observed no evidence for aggregation upon induction of fasciclin IV expression, thus suggesting that, in contrast to the other four proteins, fasciclin IV does not function as a homophilic cell adhesion molecule. Alternatively, fasciclin IV-mediated aggregation might require some further post-translational modification, or co-factor, not supplied by the S2 cells, but clearly this protein acts differently in the S2 cell assay than the other four axonal glycoproteins previously tested. This is consistent with the pattern of fasciclin IV expression in the embryonic limb since only the epithelial cells and not the Ti1 growth cones express fasciclin IV, and yet antibody blocking experiments indicate that fasciclin IV functions in the epithelial guidance of these growth cones. Such results suggest that fasciclin IV functions in a heterophilic adhesion or signaling system.

Discussion

Fasciclin IV is expressed on groups of axons that fasciculate in the CNS, suggesting that, much like other insect axonal glycoproteins, it functions as a homophilic cell adhesion molecule binding these axons together. Yet, in the limb bud, fasciclin IV is expressed on a band of epithelium but not on the growth cones that reorient along this band, suggesting a heterophilic function. That fasciclin IV functions in a heterophilic rather than homophilic fashion is supported by the lack of homophilic adhesion in S2 cell aggregation assays. In contrast, fasciclin I, fasciclin II, fasciclin III, and neuroglian all can function as homophilic cell adhesion molecules (Snow et al., 1989; Elkins et al., 1990b; Grenningloh et al., 1990).

cDNA sequence analysis indicates that fasciclin IV is an integral membrane protein with a novel sequence not related to any protein in the present data base. Thus, fasciclin IV represents a new type of protein that functions in the epithelial guidance of pioneer growth cones in the developing limb bud. Given its expression on a subset of axon pathways in the developing CNS, fasciclin IV functions in the guidance of CNS growth cones as well.

The results from the MAb blocking experiments illuminate several issues in Ti1 growth cone guidance and axon morphogenesis in the limb. First, the most striking change in growth cone behavior in the limb is the cessation of proximal growth and initiation of circumferential extension of processes upon encountering the trochanter/coxa boundary region (Bentley and Caudy, 1983; Caudy and Bentley, 1987). This could be because the band of epithelial cells within the trochanter promotes circumferential growth, or because the cells comprising the trochanter/coxa boundary and the region just proximal to it are non-permissive or aversive for growth cone migration, or both. The extension of many axon branches across the trochanter/coxa boundary following treatment with MAb 6F8 suggests that the trochanter/coxa boundary cells, which do not express fasciclin IV, are not aversive or non-permissive. Thus the change in behavior at the boundary appears to be due to the ability of fasciclin IV expressing epithelial cells to promote circumferential extension of processes from the Ti1 growth cones.

Secondly, treatment with MAb 6F8 results in frequent defasciculation of the axons of the two Ti1 neurons, and also formation of abnormal multiple axon branches, within the trochanter over fasciclin IV-expressing epithelial cells. Previous studies have shown that treatment with antibodies against ligands expressed on non-neural substrates (Landmesser et al., 1988), or putative competitive inhibitors of substrate ligands (Wang and Denburg, 1992) can promote defasciculation and increased axonal branching. Our results suggest that Ti1 axon:axon fasciculation and axon branching also are strongly influenced by interactions with substrate ligands, and that fasciclin IV appears to be a component of this interaction within the trochanter.

Thirdly, despite the effects of MAb 6F8 on axon branching, and on crossing the trochanter/coxa boundary, there remains a pronounced tendency for branches to grow ventrally both within the trochanter and within the distal region of the coxa. Consequently, all signals which can promote ventral migration of the growth cones have not been blocked by MAb 6F8 treatment. Antibody treatment may have a threshold effect in which ventral growth directing properties of fasciclin IV are more robust, and less incapacitated by treatment, than other features; alternatively, guidance information promoting ventral migration may be independent of fasciclin IV. Time lapse video experiments to determine how the abnormal pathways we observe actually form can resolve these issues.

These results demonstrate that fasciclin IV functions as a guidance cue for the Ti1 growth cones just distal to the trochanter/coxa boundary, is required for these growth cones to stop proximal growth and spread circumferentially, and that the function of fasciclin IV in Ti1 pathway formation result from interactions between a receptor/ligand on the Ti1 growth cones and fasciclin IV on the surface of the band of epithelial cells results in changes in growth cone morphology and subsequent reorientation. Fasciclin IV appears to elicit this change in growth cone morphology and orientation via regulation of adhesion, a signal transduction function, or a combination of the two.

Experimental Procedures

Immunocytochemistry

Grasshopper embryos were obtained from a colony maintained at the U. C. Berkeley and staged by percentage of total embryonic development (Bentley et al., 1979). Embryos were dissected in PBS, fixed for 40 min in PEM-FA [0.1M PIPES (pH6.95), 2.0 mM EGTA, 1.0 mM MgSO$_4$, 3.7% formaldehyde], washed for 1 hr with three changes in PBT (1× PBS, 0.5% Triton X-100, 0.2% BSA), blocked for 30 min in PBT with 5% normal goat serum, and incubated overnight at 4° C. in primary antibody. PBSap (1× PBS, 0.1% Saponin, 0.2% BSA) was used in place of PBT with MAb 8G7. Antibody dilutions were as follows: MAb 6F8 1:1, polyclonal antisera directed against a fasciclin IV bacterial fusion protein (#98-3) 1:400; MAb 8G7 1:4; MAb 8C6 1:1. The embryos were washed for one hour in PBT with three changes, blocked for 30 min, and incubated in secondary antibody for at least 2 hr at room temperature. The secondary antibodies were HRP-conjugated goat anti-mouse and anti-rat IgG (Jackson Immunoresearch Lab), and were diluted 1:300. Embryos were washed in PBT for one hour with three changes and then reacted in 0.5% diaminobenzidine (DAB) in PBT. The reaction was stopped with several washes in PBS and the embryos were cleared in a glycerol series (50%, 70%, 90%), mounted and viewed under Nomarski or bright field optics. For double-labelled preparations the first HRP reaction was done in PBT containing 0.06% NiCl, followed by washing, blocking, and incubation overnight in the second primary antibody. The second antibody was visualized with a DAB reaction as described above. Embryos cultured in the presence of monoclonal antibodies were fixed and incubated overnight in goat anti-HRP (Jackson Immunoresearch Labs) conjugated to RITC (Molecular Probes), washed for one hour in PBT with three changes, mounted in 90% glycerol, 2.5% DABCO (Polysciences), and viewed under epifluorescence. S2 cells were stained with polyclonal sera #98-3 diluted 1:400 and processed as described previously (Snow et al., 1989).

Monoclonal Antibody Blocking Experiments

In order to test for functional blocking, monoclonal antibody reagents were prepared as follows. Hybridoma supernatant was brought to 20% with H$_2$O-saturated (NH$_4$)$_2$SO$_4$, incubated in ice 1 hr, and spun at 15,000 g at 4° C. for 20 min. The supernatant was brought to 56% with H$_2$O-saturated (NH$_4$)$_2$SO$_4$, incubated overnight at 4° C., spun as above. The pellet was resuspended in PBS using approximately 1/40 volume of the original hybridoma supernatant (often remaining a slurry) and dialyzed against 1× PBS overnight at 4° C. with two changes. This reagent is referred to as "concentrated hybridoma supernatant". Purified IgG was obtained by using Immunopure Plus Immobilized Protein A IgG Purification Kit (Pierce) to isolate IgG from the concentrated hybridoma supernatant. Fab fragments were obtained using the ImmunoPure Fab Preparation Kit (Pierce) from the previously isolated IgGs. For blocking experiments each reagent was diluted into freshly made supplemented RPMI culture media (O'Connor et al., 1990) and dialyzed overnight at 4° C. against 10 volumes of the same culture media. Dilutions were as follows: concentrated hybridoma supernatant 1:4; purified IgG 150 mg/ml; Fab 75 mg/ml.

Embryos for culture experiments were carefully staged to between 31 and 32% of development. As embryos in each clutch typically differ by less that 1% of embryonic development from each other, the growth cones of the Ti1 neurons at the beginning of the culture period were located approximately in the mid-femur, well distal to the trochanter/coxa segment boundary. From each clutch at least two limbs were filleted and the Ti1 neurons labelled with the lipophillic dye Di I (Molecular Probes) as described (O'Connor et al., 1990) in order to confirm the precise location of the Ti1 growth cones. Prior to culturing, embryos were sterilized and dissected (Chang et al., 1992). The entire amnion and dorsal membrane was removed from the embryo to insure access of the reagents during culturing. Embryos were randomly divided into groups and cultured in one of the blocking reagents described above. Cultures were incubated with occasional agitation at 30° C. for 30 hrs. At the end of the culture period embryos were fixed and processed for analysis as described above in immunocytochemistry.

For each culture experiment, the scoring of the Ti1 pathway in each limb was confirmed independently by a second observer. There was no statistically significant variation between the two observers. Limbs from MAb cultured embryos were compared to representative normal limbs from non-MAb cultured embryos and were scored as abnormal if any major deviation from the normal Ti1 pathway was observed. The Ti1 pathway was scored as abnormal for one or more of the following observed characteristics: (1) defasciculation for a minimum distance of approximately 25 mm anywhere along the pathway, (2) multiple axon branches that extended ventrally within the trochanter, (3) presence of one or more axon branches that crossed the trochanter/coxa boundary dorsal to the Cx1 cells, but then turned ventrally in the coxa and contacted the Cx1 cells, (4) the presence of axon branches that crossed the trochanter/coxa segment boundary, did not turn ventrally, but continued proximally toward the CNS, and (5) failure of ventrally extended axons within the trochanter to contact and reorient proximally to the Cx1 cells. For each MAb tested, the data are presented as a percentage of the abnormal Ti1 pathways observed.

Protein Affinity Purification and Microsequencing

Grasshopper fasciclin IV was purified by passing crude embryonic grasshopper lysate (Bastiani et al., 1987) over an Affi-Gel 15 column (Bio Rad) conjugated with the monoclonal antibody 6F8. Protein was eluted with 50 mM DEA (pH 11.5), 0.1% Lauryldimethylamine oxide (Cal Bio Chem), and 1 mM EDTA. Protein was then precipitated, denatured, modified at cysteines, and digested with either trypsin or Lys-C (Boehringer-Mannheim). Individual peptides were resolved by RP-HPLC and microsequenced (Applied Biosystems 4771 Microsequencer) using standard chemistry.

PCR Methods

DNA complementary to poly(A)+ RNA from 45%–50% grasshopper embryos was prepared (Sambrook et al., 1989). PCR was performed using Perkin Elmer Taq polymeruse (Saiki et al., 1988), and partially degenerate (based on grasshopper codon bias) oligonucleotides in both orientations corresponding to a portion of the protein sequence of several fasciclin IV peptides as determined by microsequencing. These oligonucleotides were designed so as not to include all of the peptide-derived DNA sequence, leaving a remaining 9–12 base pairs that could be used to confirm the correct identity of amplified products. All possible combinations of these sequences were tried. 40 cycles were performed, the parameters of each cycle as follows: 96° for one min; a sequentially decreasing annealing temperature (2° C./cycle, starting at 65° C. and ending at 55° C. for remaining 35 cycles) for 1 min; and at 72° C. for one min. Reaction products were cloned into the Sma site of M13 mp10 and sequenced. Two products, 1074 bp and 288 bp in length, contained DNA 3' to the oligonucleotide sequences encoded the additional amino acid sequence of the fasciclin IV peptide from which the oligonuceotides were derived.

cDNA Isolation and Sequence Analysis

Both PCR products were used to screen 1×10$^6$ clones from a grasshopper embryonic cDNA library (Snow et al., 1988). 21 clones that hybridized to both fragments were recovered, and one 2600 bp clone was sequenced using the dideoxy chain termination method (Sanger et al., 1977) and Sequenase (US Biochemical Corp.). Templates were made from M13 mp10 vectors containing inserts generated by sonication of plasmid clones. One cDNA was completely sequenced on both strands using Oligonucleotides and double strand sequencing of plasmid DNA (Sambrook et al., 1989) to fill gaps. Two additional cDNAs were analyzed by double strand sequencing to obtain the 3' 402 bp of the transcript. All three cDNAs were used to construct a plasmid containing the entire transcript. The complete transcript sequence is 2860 bp in length with 452 bp of 5' and 217 bp of 3' untranslated sequences containing stop codons in all reading frames. The predicted protein sequence was analyzed using the FASTDB and BLASTP programs (Intelligenetics). The fasciclin IV ORF unambiguously contains 10 of the 11 peptide sequences determined by microsequencing the fasciclin IV trypsin and Lys-C peptides.

Generation of Polyclonal Antibodies From Bacterial Fusion Proteins

Bacterial trpE fusion proteins were constructed using pATH (Koerner et al., 1991) vectors, three restriction fragments encoding extracellular sequences, and one fragment (770 bp HindIII/Eco R1, which includes amino acids 476–730) encoding both extracellular and intracellular sequences (designated #98-3) Fusion proteins were isolated by making an extract of purified inclusion bodies (Spindler et al., 1984), and rats were immunized with ~70 mg of protein emulsified in RIBI adjuvant (Immunochem Research). Rats were injected at two week intervals and serum was collected 7 days following each injection. Sera were tested histologically on grasshopper embryos at 45% of development. Construct #98 -3 showed a strong response and exhibited a staining pattern identical to that of MAb 6F8. Two of the extracellular constructs responded weakly but also showed the fasciclin IV staining pattern. All preimmune sera failed to stain grasshopper embryos.

S2 Cell Transfections, Aggregation Assays, and Western Analysis

A restriction fragment containing the full length fasciclin IV cDNA was cloned into pRmHa-3 (Bunch et al, 1988) and co-transformed into Drosophila S2 cells (Schneider, 1972) with the plasmid pPC4 (Jokerst et al., 1989), which confers a-amanitin resistance. S2 cells were transformed using the Lipofectin Reagent and recommended protocol (BRL) with minor modifications. All other S2 cell manipulations are essentially as described (Snow et al.,1989), including adhesion assays. Fasciclin IV expression in transformed cell lines was induced for adhesion assays and histology by adding CuSO$_4$ to 0.7 mM and incubating for at least 48 hrs. Northern analysis confirmed transcription of fasciclin IV and surface-associated staining of the S2 cells with polyclonal serum #98-3 strongly suggests fasciclin IV is being transported to the cell surface. Preparation of membranes from S2 cells and from grasshopper embryos, PAGE, and Western blot were performed as previously described (Elkins et al., 1990b) except that signal was detected using the enhanced chemiluminescence immunodetection system kit (Amersham). Amount of protein per lane in each sample loaded: fasciclin IV protein, ~5 ng; S2 cell membranes, 40 mg; grasshopper membranes 80 mg. Amounts of protein loaded were verified by Ponceau S staining of the blot prior to incubation with the antibody.

REFERENCE CITED IN EXAMPLE I

Altschul, S. F., Gish, W., Miller, W., Myers, E. W., and Lipman, D. J. (1990). Basic local alignment search tool. J. Mol. Biol. 215, 403–410.

Bastiani, M. J., de Couet, H. G., Quinn, J. M. A., Karlstrom, R. O., Kotrla, K., Goodman, C. S., and Ball, E. E. (1992). Position-specific expression of the annulin protein during grasshopper embryogenesis. Dev. Biol., in press.

Bastiani, M. J., du Lac, S., and Goodman, C. S. (1986). Guidance of neuronal growth cones in the grasshopper embryo. I. Recognition of a specific axonal pathway by the pCC neuron. J. Neurosci. 6, 3518–3531.

Bastiani, M. J., and Goodman, C. S. (1986). Guidance of neuronal growth cones in the grasshopper embryo: III. Recognition of specific glial pathways. J. Neurosci. 6, 3542–3551.

Bastiani, M. J., Harrelson, A. L., Snow, P. M., and Goodman, C. S. (1987). Expression of fasciclin I and II glycoproteins on subsets of axon pathways during neuronal development in the grasshopper. Cell 48, 745–755.

Bastiani, M. J., Raper, J. A., and Goodman, C. S. (1984). Pathfinding by neuronal growth cones in grasshopper embryos. III. Selective affinity of the G growth cone for the P cells within the A/P fascicle. J. Neurosci. 4, 2311–2328.

Bentley, D., and Caudy, M. (1983). Pioneer axons lose directed growth after selective killing of guidepost cells. Nature. 304, 62–65.

Bentley, D., Keshishian, H., Shankland, M., and Toroian-Raymond, A. (1979). Quantitative staging of embryonic development of the grasshopper, Schistocerca nitens. J. Embryol. Exp. Morph. 54, 47–74.

Bentley, D., and O'Connor, T. P. (1992). Guidance and steering of peripheral pioneer growth cones in grasshopper embryos. In The Nerve Growth Cone, P. C. Letourneau, S. B. Kater, and E. R. Macagno eds. (New York: Raven Press, Ltd.), pp. 265–282.

Bunch, T. A., Grinblat, Y., and Goldstein, L. S. B. (1988). Characterization and use of the Drosophila metallothionein promoter in cultured Drosophila melanogaster cells. Nucleic Acids Res. 16, 1043–1061.

Chang, W. S., Serikawa, K., Allen, K., and Bentley, D. (1992). Disruption of pioneer growth cone guidance in vivo by removal of glycosyl-phosphatidylinositol-anchored cell surface proteins. Development. 114, 507–519.

Caudy, M., and Bentley, D. (1987). Pioneer growth cone behavior at a differentiating limb segment boundary in the grasshopper embryo. Dev. Biol. 119, 454–465.

Chou, P. Y., and Fasman, G. D. (1974). Prediction of protein conformation. Biochemistry. 13, 222–245.

Elkins, T., Zinn, K., McAllister, L., Hoffmann, F. M., and Goodman, C. S. (1990a). Genetic analysis of a Drosophila neural cell adhesion molecule: Interaction of fasciclin I and abelson tyrosine kinase mutations. Cell. 60, 565–575.

Elkins, T., Hortsch, M., Bieber, A. J., Snow, P. M., and Goodman, C. S. (1990b). Drosophila fasciclin I is a novel homophilic adhesion molecule that along with fasciclin III can mediate cell sorting. J. Cell Biol. 110, 1825–1832.

Goodman, C. S., Bate, C. M., and Spitzer, N. C. (1981). Embryonic development of identified neurons: Origin and transformation of the H cell. J. Neurosci. 1, 94–102.

Grenningloh, G., Bieber, A., Rehm, J., Snow, P. M., Traquina, Z., Hortsch, M., Patel, N. H., and Goodman, C. S. (1990). Molecular genetics of neuronal recognition in Drosophila: Evolution and function of immunoglobulin superfamily cell adhesion molecules. Cold Spring Harbor Symp. Quant. Biol. 55, 327–340.

Grenningloh, G., Rehm, E. J., and Goodman, C. S. (1991). Genetic analysis of growth cone guidance in Drosophila: Fasciclin II functions as a neuronal recognition molecule. Cell. 67, 45–57.

Harrelson, A. L., and Goodman, C. S. (1988). Growth cone guidance in insects: Fasciclin II is a member of the immunoglobulin superfamily. Science. 242, 700–708.

Jacobs, J. R., and Goodman, C. S. (1989). Embryonic development of axon pathways in the Drosophila CNS. I. A glial scaffold appears before the first growth cones. J. Neurosci. 7, 2402–2411.

Jay, D. J., and Keshishian, H. (1990). Laser inactivation of fasciclin I disrupts axon adhesion of grasshopper pioneer neurons. Nature. 348, 548–551.

Jokerst, R. S., Weeks, J. R. Zehring, W. A., and Greenleaf, A. L. (1989). Analysis of the gene encoding the largest subunit of RNA polymerase II in Drosophila. Mol. Gen. Genet. 215, 266–275.

Koerner, T. J., Hill, J. E., Myers, A. M., and Tzagoloff, A. (1991). High-expression vectors with multiple cloning sites for construction of trpE-fusion genes: pATH vectors. Methods Enzymol. 194, 477–490.

Landmesser, L., Dahm L., Schultz, K., and Ritishauser, U. (1988). Distinct roles for adhesion molecules during innervation of embryonic chick muscle. Dev. Biol. 130, 645–670.

Lefcort, F., and Bentley, D. (1987). Pathfinding by pioneer neurons in isolated, opened and mesoderm-free limb buds of embryonic grasshoppers. Dev. Biol. 119, 466–480.

Lefcort, F., and Bentley, D. (1989). Organization of cytoskeletal elements and organelles preceding growth cone emergence from an identified neuron in situ. J. Cell. Biol. 108, 1737–1749.

O'Connor, T. P., Duerr, J. S., and Bentley, D. (1990). Pioneer growth cone steering decisions mediated by single filopodial contacts in situ. J. Neurosci. 10, 3935–3946.

Patel, N. H., Martin-Blanco, E., Coleman, K. G., Poole, S. J., Ellis, M. C., Kornberg, T. B., and Goodman, C. S. (1989). Expression of engrailed proteins in arthropods, annelids, and chordates. Cell. 58, 955–968.

Patel, N. H., Snow, P. M., and Goodman, C. S. (1987). Characterization and cloning of fasciclin III: A glycoprotein expressed on a subset of neurons and axon pathways in Drosophila. Cell. 48, 975–988.

Raper, J. A., Bastiani, M. J., and Goodman, C. S. (1984). Pathfinding by neuronal growth cones in grasshopper embryos. IV. The effects of ablating the A and P axons upon the behavior of the G growth cone. J. Neurosci. 4, 2329–2345.

Saiki, R. K., Gelfand, D. H., Stoffel, S., Scharf, S. J., Higuchi, R., Horn, G. T., Mullis, K. B., and Ehrlich, H. A. (1988). Primer-directed enzymatic amplification of DNA with a thermostable DNA polymerase. Science 239, 487–494.

Sambrook, J., Fritsch, E. F., and Maniatis, T. (1989). Molecular Cloning: A Laboratory Manual (Cold Spring Harbor, N.Y.: Cold Spring Harbor Laboratory).

Sanger, F., Nicklen, S., and Coulson, A. R. (1977). DNA sequencing with chain-terminating inhibitors. Proc. Natl. Acad. Sci. U.S.A. 74, 5463–5467.

Schneider, I. (1972). Cell lines derived from late embryonic stages of Drosophila melanogaster. J. Embryol. Exp. Morphol. 27, 353–365.

Snow, P. M., Bieber, A. J., and Goodman, C. S. (1989). Fasciclin III: a novel homophilic adhesion molecule in Drosophila. Cell. 59, 313–323.

Snow, P. M., Zinn, K., Harrelson, A. L., McAllister, L., Schilling, J., Bastiani, M. J., Makk, G., and Goodman, C. S. (1988). Characterization and cloning of fasciclin I and fasciclin II glycoproteins in the grasshopper. Proc. Natl. Acad. Sci. U.S.A. 85, 5291–5295.

Spindler, K. R., Rosser, D. S., and Berk, A. J. (1984). Analysis of adenovirus transforming proteins from early regions 1A and 1B with antisera to inducible fusion antigens produced in *Escherichia coli*. J. Virol. 49, 132–141.

Wang, L., and Denburg, J. L. (1992). A role for proteoglycans in the guidance of a subset of pioneer axons in cultured embryos of the cockroach. (1992). Neuron. 8, 701–714.

Wang, L. S., Feng, Y., and Denburg, J. L. (1992). A multifunctional cell surface developmental stage-specific antigen in the cockroach embryo: involvement in pathfinding by CNS pioneer axons. J. Cell Biol. 118, 163–176.

Zinn, K., McAllister, L., and Goodman, C. S. (1988). Sequence analysis and neuronal expression of fasciclin I in grasshopper and Drosophila. Cell. 53, 577–587.

Genbank Accession Number:

The accession number for the sequence reported in this paper is L00709.

II. Isolation and characterization of Tribolium (SEQ ID NOS:63 and 64) and Drosophila SEQ ID NOS:59 and 60:) Semaphorin I, Drosophila Semaphorin II (SEQ ID NOS:61 and 62:). Human Semaphorin III (SEQ ID NOS:53 and 54:) and Vaccinia Virus Semaphorin IV (SEQ ID NOS:55 and 56) and Vadola Major (smallpox) Virus Semaphorin V (SEQ ID NOS:67 and 68:).

We used our G-Semaphorin I cDNA in standard low stringency screening methods (of both cDNA and genomic libraries) in an attempt to isolate a potential Semaphorin I homologue from Drosophila. We were unsuccessful in these screens. Since the sequence was novel and shared no similarity to anything else in the data base, we then attempted to see if we could identify a Semaphorin I homologue in other, more closely related insects. If possible, we would then compare these sequences to find the most conserved regions, and then to use probes (i.e., oligonucleotide primers for PCR) based on these conserved regions to find a Drosophila homologue.

In the process, we used the G-Semaphorin I cDNA in low stringency screens to clone Semaphorin I cDNAs from libraries made from locust *Locusta migratoria* embryonic RNA and from a cDNA embryonic library from the cricket Acheta domestica. We used PCR to clone genomic fragments from genomic DNA in the beetle Tribolium, and from the moth Manduca. We then used the Tribolium genomic DNA fragment to isolate cDNA clones and ultimately sequenced the complete ORF for the Tribolium cDNA.

In the meantime, we used the partial Tribolium and Manduca sequences in combination with the complete grasshopper sequence to identify conserved regions that allowed us to design primers for PCR in an attempt to clone a Drosophila Semaphorin I homologue. Several pairs of primers generated several different bands, which were subcloned and sequenced and several of the bands gave partial sequences of the Drosophila Semaphorin homologue. One of the bands gave a partial sequence of what was clearly a different, more divergent gene, which we call D-Semaphorin II.

Based on the sequence of PCR products, we knew we had identified two different Drosophila genes, one of which appeared to be the Semaphorin I homologue, and the other a second related gene. The complete ORF sequence of the D-Semaphorin I homologue revealed an overall structure identical to G-Semaphorin I: a signal sequence, an extracellular domain of around 550 amino acids containing 16 cysteines, a transmembrane domain of 25 amino acids, and a cytoplasmic domain of 117 amino acids. When we had finished the sequence for D-Semaphorin II, we were able to begin to run homology searches in the data base, which revealed some of its structural features further described herein. The Semaphorin II sequence revealed a different structure: a signal sequence of 16 amino acids, a ~525 amino acid domain containing 16 cysteines, with a single immunoglobulin (Ig) domain of 66 amino acids, followed by a short unique region of 73 amino acids. There is no evidence for either a transmembrane domain or a potential phospholipid linkage in the C-terminus of this protein. Thus, it appears that the D-Semaphorin II protein is secreted from the cells that produce it. The grasshopper, Tribolium, and Drosophila Semaphorin I cDNA sequences, as well as the sequence of the D-Semaphorin II cDNA, are shown herein. In addition, we used this same technique to identify Semaphorin I genes in a moth, *Manduca sexta*, a locust, *Locusta migratoria*, and a cricket, *Acheta domestica*.

With this large family of insect Semaphorin genes, we identified a number of good stretches of the right amino acids (with the least degeneracy based on their codons) with strong homology for designing primers for PCR to look for human genes. We designed a set of oligonucleotide primers, and plated out several human cDNA libraries: a fetal brain library (Stratagene), and an adult hippocampus library. We ultimately obtained a human cDNA PCR bands of the right size that did not autoprime and thus were good candidates to be bonafide Semaphorin-like cDNAs from humans. These bands were purified, subcloned, and sequenced.

Whole-mount in situ hybridization experiments showed that D-Semaphorin I and II are expressed by different subsets of neurons in the embryonic CNS. D-Semaphorin I is expressed by certain cells along the midline as well as by other neurons, whereas D-Semaphorin II is not expressed at the midline, but is expressed by a different subset of neurons. In addition, D-Semaphorin II is expressed by a subset of muscles prior to and during the period of innervation by specific motoneuron. On the polytene chromosomes, the D-Semaphorin I gene maps to (gene-band-chromosome) 29E1-22L and that of D-Semaphorin II to 53C9-102R. We have identified loss of function mutations in the D-Semaphorin I gene and a pair of P-element transposon insertions in the D-Semaphorin II gene which appear to cause severe phenotypes.

When we lined up the G-Semaphorin I, T-Semaphorin I, D-Semaphorin I, and D-Semaphorin II sequences and ran the sequences through a sequence data base in search of other sequences with significant similarity, we discovered a curious finding: these Semaphorins share sequence similarity with the A39R open reading frame (ORF) from Vaccinia virus and the A43R ORF from *Variola Major* (smallpox) virus and we discovered that the amino acids shared with the virus ORF were in the same regions where the insect proteins shared their greatest similarity. The viral ORF began with a putative signal sequence, continued for several hundred amino acids with sequence similarity to the Semaphorin genes, and then ended without any membrane linkage signal (suggesting that the protein as made by the infected cell would likely be secreted).

We reasoned that the virus semaphorins were appropriated host proteins advantageously exploited by the viruses, which would have host counterparts that most likely function in the immune system to inhibit or decrease an immune response, just as in the nervous system they appear to function by inhibiting growth cone extension. Analogous to situations where viruses are thought to encode a secreted form of a host cellular receptor, here the virus may cause the infected cell to make a lot of the secreted ligand to mimic an inhibitory signal and thus help decrease the immune response.

III. Isolation and characterization of Murine CNS Semaphorin III Receptor using Epitope Tagged Human Semaphorin III (hSIII)

mRNA was isolated from murine fetal brain tissue and used to construct a cDNA library in a mammalian expression vector, pCMX, essentially as in Davis et al. (1991) Science 253, 59.

The transfection and screening procedure is modified from Lin et al (1992) Cell 68, 775. COS cells grown on glass slide flaskettes are transfected with pools of the cDNA clones, allowed to bind radioiodinated hSIII truncated at the C-terminus end of the semaphorin domain. In parallel, similarly treated COS cells are allowed to bind unlabelled human semaphorin III truncated at the C-terminus end of the semaphorin domain and there joined to a 10-amino acid extension derived from the human c-myc proto-oncogene product. This modified hSIII allows the identification of hSIII receptors with the use of the tagged ligand as a bridge between the receptor and a murine monoclonal antibody which is specific for an epitope in the c-myc tag. Accordingly, after binding unlabelled hSIII the cells are exposed to the monoclonal which may be labeled directly or subsequently decorated with a secondary anti-mouse labeled antibody for enhanced signal amplification.

Cells are then fixed and screened using dark-field microscopy essentially as in Lin et al. (supra). Positive clones are identified and sequence analysis of murine CNS Semphorin III receptor cDNA clones by the dideoxy chain termination method is used to construct full-length receptor coding sequences.

It is evident from the above results that one can use the methods and compositions disclosed herein for making and identifying diagnostic probes and therapeutic drugs. It will also be clear to one skilled in the art from a reading of this disclosure that advantage can be taken to effect alterations of semaphorin responsiveness in a host.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

Deduced amino-acid sequence of semaphorin gene family.

Approximate position of enumerated peptide classes are indicated by parenthetical (a) through (o); semaphorin domains are bounded by arrows; G: grasshopper semaphorin I (SEQ ID NO:58), T: Tribolium semaphorin I (SEQ ID NO:64), D1: Drosophila semaphorin I (SEQ ID NO:60), D2: Drosophila semaphorin II (SEQ ID NO:62), H3: Human semaphorin I (SEQ ID NO:54), V4: Vaccinia virus semaphorin IV (SEQ ID NO:56), V5: Variola virus (human small pox) semaphorin IV (SEQ ID NO:66); small case residues: conserved residues; underline: signal sequence; solid bar: transmembrane domain; double dashes: immunoglobulin domain.

```
G                                   MR AAL VAVAALL WVVAL HAAA WVNDVSPKMYVQFGEERVQR
T                                      MVVKI LVWSI CLI ALCHAWMPDSSSKLI NHFKSVESKS
D1
D2    MSLL OLSPLLALLLLLCS SVSETAADYENT WNF YYERPCCTGNDQGNNNYGKHGADHVRE
H3                   MGWLTRI VCLF WGVLLTARANYQNGKNNVPRLKLSYKEMLESNNVI T
V4                                                   MMVLLHAVYSI VFVDVI I IKVQRYI NDI

↓
G     f -Lg --nESHKDHf KLLe KDHNSl Lvga --r NI ---VYnI SLRDLTEFTEQRi EwHSs GAHRELcY
T     f T-g --nATFPDHf I VLNQDETSI Lvg G--r NR---VYnLSI FDLSERKGGRi DwPSs DAHGQLcI
D1
D2    f NCg KLY---YRTf HMNe DRDT-l Yvg a MDr VF ---RVnLQNI SSSNCNRDAi NLEPTRDDVVSc V
H3    f N-gLAnSSSYHTf LLDe ERSR-l Yvg a KDHI FSFDLVnI -------KDFQKi VwPVs YTRRDEcK
V4    LTLDI FYLFKKMI PLLFI LFYFANGI EWHKFETSEEI I STYLLDDV------LYTGVNGAVYTFSN A
                F                              V
        DDCQN-YI R(a)                          I CGTN(b)
G     LkgkS-Eddcqn-yir --Vl AKI DDDr VLI cgt na YKpLcRHy ALKd -----GDy VVe KEYEgRg ----
T     lkgkT-Dddcqn-yir --i l YSSEPGKl VI cgt nSYKpLcRTy AFKE-----GKy LVe KEVEgI g ----
D1           Eddcqn-yir --i MVVPSPGr l Fvcgt nSFRpMc NTyI I Sd -----SNy TLe ATKNg QA----
D2    SkgkSQI Fdc KnHVi q --SMDQGD--r l Yvcgt na HNpKDYVi YANL-----THLPRSEYVI gVgLGI A
H3    WAgkDI LKEc An-Fi K--Vl KAYNQTHl YAcgt GaFHpI c TYi EI GHPEDNI FKLENEHFENgRg ----
V4    NkLNKTGLTNNn-yi TTSi KVEDADKDTLvcgt nNGNpKc WKi DGSd ---------------------

S  F                                    A
       CPYDP(c)                                TVADFSG(d)
G     LcpFdpDh---------nst AI TS Eg Q-------lys At vadfsgTdPLiyr Gpl ------------
T     LcpyNpEh---------nsts VSYNg Q-------l Fs At vadfsgGdpLiyr EpQ------------
D1    VcpydpRh---------nsts VLADNE-------lysgt vadfsgSdpI iyr Epl ------------
D2    KcpydpLD---------nst AI YVENGNPGGLPGl ysgt Na Ef TKAdTVi Fr TDl YNTSAKRLEYKF
H3    KSpydpKL---------LTAs LLI Dg E-------lysgt Aadf MgRdFAi Fr T-l GHHHPI RTEQHD
V4    ----dpKh RGRGYAPYQns KVTI I SHNGc YLSDI NI s KEGI KRWRRFDGPc GYDl ------------
V5                                                             MI Yl ------------
```

TABLE 1-continued

Deduced amino-acid sequence of semaphorin gene family.

```
                    LNAPNFV(e)              (fFFRETA EYI NCGK(g)                                                    (h)DKGG
G    -rteRSdLkQ-lnapnfv--NTMEyNdFHFIFffretaveyincgkaiysrvarvckHdkgg
T    -rteLsdLkQ-lnapnfv-Ns VAygdYI FfYretaveyMncgkViYsrvarvckDdkgg
D1   -QteQYdSLS-lnapnfv--Ss Ft QgdFvyffretaveFincgkaiysrvarvckWdkgg
D2   KrtLKYdskW-lDKpnfy-GsFDI gEYvyfffretaveyincgkaVysriarvckKd Vgg
H3   -SRWLNdpkF-ISaHLISEsdNPEDdkvyfffreNaIDGEHSgkaTHArIGQIcknd Fgg
V4   YTADNVIpkDGlRGA-fvDKdGty-dkvyILfTDtIG-SKRIVkIPy---iaQMcLndEgg
V5   YTADNVIpkDGlQGA-fvDKdGty-dkvyILfTVIG-SKRIVkIPy---iaQMcLndECg PH               S  S Y(i)                                      V
                    WTTFLKAR  NCSIPG(j)
G    phQF-GDrwtsflkSrlncsVpgDypfyf---neiqs-----tsdIlegNyGGQVEkliygv
T    phQ--SRDrwtsflkarlncsipgEypfyf---Deiqs-----tsdIvegRyNsDDskIiygI
D1   phRF-RNrwtsflkSrlncsipgDypfyf---neiqs---AsNLvegQyGsMSs Kliygv
D2   KNLi-AhNwAtYlkarlncsisGgEFpfyf-----------VYQL--PsDKsRF-FAT
H3   -hRsLVNKwttflkarIlcsVpgPNGIDTHf-Delq------dVFLMNFKDPKNPVVygv
V4   pssisShrwStflkVEIEcDiDgRsYRQIIHsRTi KTDNDtILvF-FDsPYsk------
V5   pssisShrwStLlkVEIEcDiDgRsYSYSQINHsKTi KQIMIRYYMYSLI VLFQVRIMYLFY GSAVC(k)                                     V
                                        NSNWLPV(l)                     PRPGTCVND(m)
G    fttpVnSiGgsavcafsmKSiLESfDgPfkeqETMnsnwlAvPSLKvpeprpgQcvndsr
T    LttpVnAiGgsaIcayQmAdiLRVFgSfkHqETInsnwlPvPQNLvpeprpgQcvRdsr
D1   fNtpSnsiPgsavcayALQdiADTfEgdQfkeqTGInsnwlPvNNAKvpDprpgScHndsr
D2   fttSTnGLIgsavcSfHINEiQAAfNgKfkeqSSSnsAwlpvLNSRvpeprpgTcvndTS
H3   fttSsniFKgsavcMysmSdVRRvfLgPYAHRDGPnYQwVp-YQGRvpYprpgTc--PsK
V4   --VvpHTTFEViEKYNVIDdIIKp-LSnQpiFEGPSGVKWFDIKEKENEHREYRIYFIKENS
V5   EYH                              ---sa LcTysmNTi KQSfSTSKLeg----------YTKQLpSpApgIcLPAGK DPYCAWD(n)
G    ----------TlpdVSVnfV--kShTlmdEAvpaFfTRpiIIrIsIQyrftKiAvdQqvRtPDgKAYdvLf
T    ----------IlpdKNVnfi--kThSlmED-vpaLfGKpVlVrVsIQyrftAiTvdPqvKtINNQYIdvLy
D1   ----------AlpdPTLnfi--kThSlmdENvpaFfSQpilVrTsTIyrftQiAvdAqIKtPGgKTydvIf
D2   ----------NlpdTVLnfi--RShPlmdKAvNHEHnNpVYYKRDlVFTK-LVVDKI RIDI LNQEYI-vYY
H3   TFGGFDSTKDlpdVITfA-rshPAmYNPvFPMNnRpiVIKTDVNyQftQiVvd-RvDAEDgQY-dvMf
V4   VvpHTTFEVIEKYNVIDdIIKp-LSnQpiFEGPSGVKWFDIKEKENEHREYRIYFIKENS G    igtddgkvlkALnSAsFDSSDTvDSvVIeeLQvLPPGVpVKnlYVvr-------------Mdg---d
T    itddgkvLkAvnIPKRHAKALLYRKYRTSVHPHGA--pvKQlKIAP----------------G
D1   VgtdHgkIIkSvnAEsADSADKvTSvVIeeIDvLTKSEpIRnIEIvrTMQYDQPKdgSYd
D2   VgtNLgRIYkIvnGEsLSKLLDIFERvAPNeAIQVMEISQTR--------MELSTK
H3   igtdVgTvLkVvSIPKETWY-DLEEvLLeeMTvFREPTAISA------
V4   iYSFdTkSKQTRSSQVDARLFSvMTSKPLFIADIGIGVGMPQMKKILKM- G    dsklVVvSdDEiLAikIhrcGSdkItNcRecvSlqdPycawdNVELKcTAvgSpDwSAG
T    YGkVVVvGKDEiRLANINHcAS-k--tRcKDcvEIqdpHcawdAKQNLcVSIDTVTSY--
D1   dGkllivTdSQVVAiQlhrcHNdkItScSecvAlqdpycawdKIAGKcRSHgApRw-LE
D2   -KslYiGTdHRiKQiDlAMc-NRRYDNcFRcv--RdpycGwdKEANTcRPY---------
H3   QQQIYiGSTAGVAQLPlhrcDIYG-KAcAecCLARdpycawdS---RYFPTAK
```

TABLE 1-continued

Deduced amino-acid sequence of semaphorin gene family.

```
            ↓
G    Kr RFIqNI SLg EH-KAc GGRPQTEI VASPVPTQPTTKSSGDPVHSIHQAEFEp ei DNEi VI
T    -r FLI q d v VRg DD-NKc Ws PQTDKKTVI KNKPSEVENEITNSI DEKDLDs SdpLi KTGLdD
D    ENYFYq Nv ATg QH-AAc Ps GKI NSk DANAGEGKGFRNDMDLLDSRRQ --s KdQei IDNi dK
D2   ELDDLLqd v ANETS-DI c Ds S VLKKk
H3   Rr TRRqdI RNg DPLTHc SDLHDNHH

G    GVdd SNVI PNTLAEI NHAGSKLPSSQEKI Pi y t aet l Ti a I vTSCLGAl Vv g f I s g FLF S
T    DSdc DPVSENSI GGc AV------RQQl Vi y t aGt l Hi Vv v VVs i VGl FSWLYs g LSVF
D    NFEd D------                    -II NAQy t Ved VMa v LAGs i FSl Lv g f FTg YFCG G    r c RGEDYTDMp Fp d QRHQLNRLTEAGI NADs PYLPPCANn k AAI n l v LNv ------Ppk N
T    AAKFHSd ------SQy p EAPFI EQHNHLERI s ANQTGYLTPRAn k -AVnl v v Kv SSSTPRp k K
D    r c HKdEDDNLp y p d TEYEYFEQRQNVNs FPs SCRI QQEPKLLPQVEEvTYAEPVLLp QP KKTYI (o)
G    An GKNANs S AENKP ----I Qk k t y i *
T    Dn LDVSKDLNI ASDGTLQKI k k t y i *
D    PPPNKMHs PKNTLRKPPMHQMHQGPNSETLFQFHVTATTPSSRI VVATTSEHCVPTR*

D2              ---I VVTy g ---Qs VHl Gc FVk I PEVI KNEQv TwYHHSKDKG
H3              GHSPEERI I y g VENSs TFl Ec SPk SQRAI ------v YwQFQRRNEE
                =============================================

D2   r Ye I RYSPTKYi ETt ERg l VVVs VNEAd Gg Ry Dc h LGGSLLc SYNI TVDAHRc TPPNKSN
H3   r Ke-IRVDDHi I Rt DQg l LLRs LQQKds g Ny Lc h AVEHGFI QTLLKVTLEVI DTEHLEE
     =============================================

D2   DYQKI YSDWc HEFEKYKT AMKS WEKKQGQc STRQNFSc NQHPNEI FRKPNV*
H3   LLHKDDDGDGS KTKEMS NS MTP SQKVWYRDFMQLI NHPNLNTMDEFc EQVWKRDKQRRQ

H3   RPGHTPGNSNKHLQENKKGRNRRTHEFERAPRSV*
```

What is claimed is:

1. An isolated semaphorin protein comprising the amino acid sequence of SEQ ID NO:54, 56, 58, 60, 62 or 64, or a portion of said amino acid sequence, said portion sufficient to provide a semaphorin binding specificity and comprising a peptide sequence selected from the group consisting of SEQ ID NOS:1-52 and 67-100, with the proviso that said protein is other than a natural vaccinia or variola major virus open reading frame translation product.

2. An isolated semaphorin protein according to claim 1, wherein said peptide sequence is selected from the group consisting of:

(a) [AspGlu]Cys[GlnLysArgAlaAsn]Asn[TyrPheVal]Ile (SEQ ID NO:1) Cys[GlnLysArgAlaAsn]Asn [TyrPheVal]Ile[ArgLysGlnThr] (SEQ ID NO:2)

(b) CysGlyThr[AsnGly][AlaSerAsn][TyrPheHisGly] [LysArgHisAsnGln] (SEQ ID NO:3) CysGlyThr [AsnGly][AlaSerAsn]XaaXaaPro (SEQ ID NO:4) CysGlyThr[AsnGly]XaaXaaXaaProXaa[CysAsp] (SEQ ID NO:5) CysGlyThrXaaXaaXaaXaaProXaa [CysAsp]XaaXaa[TyrIle] (SEQ ID NO:6)

(c) [ArgIleGlnVal][GlyAla][LeuValLys][CysSer]Pro [PheTyr][AspAsn] (SEQ ID NO:7) [CysSer]Pro [PheTyr][AspAsn]Pro[AspGluArgLys][HisLeuAsp] (SEQ ID NO:8) GlyXaa[GlyAla]Xaa[CysSer]ProTyr [AspAsn]Pro (SEQ ID NO:9)

(d) Leu[PheTyr]Ser[GlyAla]Thr[ValAsnAla]Ala (SEQ ID NO:10) Leu[PheTyr]SerXaaThrXaaAla[AspGlu] [PheTyr] (SEQ ID NO:11) [PheTyr]Ser[GlyAla]Thr [ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr] ArgGlu[ThrAsn] (SEQ ID NO:15) PhePheArgGlu [ThrAsn]Ala (SEQ ID NO:16) Phe[PheTyr]ArgGlu [ThrAsn]Ala (SEQ ID NO:17) TyrPhePhe[PheTyr] ArgGlu (SEQ ID NO:18) [PheTyr]PhePhe[PheTyr] ArgGlu (SEQ ID NO:19) [PheTyr][PheTyr][PheTyr] ArgGlu[ThrAsn]Ala (SEQ ID NO:20) [IleVal][PheTyr] Phe[PheTyr][PheTyr]ArgGlu (SEQ ID NO:21) Asp [LysPheTyr]Val[PheTyr][PheTyrIleLeu] [PheTyrIleLeu][PheTyr] (SEQ ID NO:22) [ValIle] [PheTyr][PheTyrIleLeu][PheTyrIleLeu]Phe[ArgThr] Xaa[ThrAsn] (SEQ ID NO:23) [ValIle][PheTyr] [PheTyrIleLeu][PheTyrIleLeu][PheTyr][ArgThr] [GluAspVal][ThrAsn] (SEQ ID NO:24)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle] CysXaaXaaAsp (SEQ ID NO:28) GlyLys[ValAlaIle] XaaXaaXaaArg[ValAlaIle]XaaXaaXaaCysLys (SEQ ID NO:29)

(i) [ArgLysAsn]Trp[ThrAlaSer][ThrAlaSer][PheTyrLeu] Leu[LysArg] (SEQ ID NO:30) [PheTyr]Leu[LysArg] [AlaSer]ArgLeu[AsnIle]Cys (SEQ ID NO:31) [AsnIle] CysSer[IleVal][ProSer]Gly (SEQ ID NO:32) Trp [ThrAlaSer][ThrAlaSer][PheTyrLeu]LeuLys [AlaSerValIleLeu]XaaLeu (SEQ ID NO:33) Trp

[ThrAlaSer][ThrAlaSer]
XaaLeuLysXaaXaaLeuXaaCys (SEQ ID NO:34)
TrpXaa[ThrSer]XaaLeuLysXaaXaaLeuXaaCys (SEQ
ID NO:35)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle]ProXaaPro[ArgAla]ProGlyXaaCys (SEQ ID NO:42) Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

3. An isolated semaphorin protein according to claim 1, wherein said peptide sequence is selected from the group consisting of:

(a) AspCysGlyAsnTyrIle (SEQ ID NO:67)

(b) CysGlyThr[AsnGly][AlaSer]XaaXaaPro (SEQ ID NO:68)

(c) GlyXaa[SerCys]ProTyrAspPro (SEQ ID NO:69)

(d) LeuTyrSerGlyThr[ValAsnAla]Ala (SEQ ID NO:70)

(e) LeuAsnAlaProAsnPheVal (SEQ ID NO:71)

(f) [PheTyr]PhePhe[PheTyr]ArgGlu (SEQ ID NO:19)

(g) Glu[PheTyr]IleAsn[CysSer]GlyLys (SEQ ID NO:25)

(h) Arg[ValIle]AlaArgValCysLys (SEQ ID NO:72)

(i) Trp[ThrAla][ThrSer][PheTyr]LeuLys[AlaSer]ArgLeu (SEQ ID NO:73)

(j) ProPheTyrPhe[AsnAsp]GluIleGlnSer (SEQ ID NO:74)

(k) GlySerAlaValCysXaa[PheTyr] (SEQ ID NO:75)

(l) AsnSerAsnTrpLeu[ProAla]Val (SEQ ID NO:76)

(m) Pro[GluAsp]ProArgProGly[ThrGlnSer]Cys (SEQ ID NO:77), and (n) AspProTyrCys[AlaGly]TrpAsp (SEQ ID NO:78).

4. An isolated semaphorin protein according to claim 1, wherein said peptide sequence is selected from the group consisting of:

(a) [AspGlu]Cys[GlnLysArgAlaAsn]Asn[TyrPheVal]Ile (SEQ ID NO:01) Cys[GlnLysArgAlaAsn]Asn[TyrPheVal]Ile[ArgLysGlnThr] (SEQ ID NO:02)

(b) CysGlyThr[AsnGly][AlaSer][TyrPheHisGly][LysArgHisAsnGln] (SEQ ID NO:79) CysGlyThr[AsnGly][AlaSerAsn][TyrPheHis][LysArgHisAsnGln] (SEQ ID NO:80) CysGlyThr[AsnGly][AlaSer]XaaXaaPro (SEQ ID NO:81)

(c) [ArgIleGlnVal][GlyAla][LeuValLys][CysSer]Pro[PheTyr][AspAsn] (SEQ ID NO:07) [CysSer]Pro[PheTyr][AspAsn]Pro[AspGluArgLys][HisLeuAsp] (SEQ ID NO:08) GlyXaa[GlyAla]Xaa[CysSer]ProTyr[AspAsn]Pro (SEQ ID NO:09)

(d) Leu[PheTyr]Ser[GlyAla]Thr[ValAsnAla]Ala (SEQ ID NO:10) Leu[PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu [AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]ArgGlu (SEQ ID NO:18) [PheTyr]PhePhe[PheTyr]ArgGlu (SEQ ID NO:19) [PheTyr][PheTyr][PheTyr]ArgGlu[ThrAsn]Ala (SEQ ID NO:20) [IleVal][PheTyr]Phe[PheTyr][PheTyr]ArgGlu (SEQ ID NO:21) Asp[LysPheTyr]Val[PheTyr][PheTyrLeu][PheTyrIleLeu][PheTyr] (SEQ ID NO:22) Asp[LysPheTyr]Val[PheTyr][PheTyrIleLeu][PheTyrIle][PheTyr] (SEQ ID NO:82) [ValIle][PheTyr][PheTyrLeu][PheTyrIleLeu]Phe[ArgThr]Xaa[ThrAsn] (SEQ ID NO:83) [ValIle][PheTyr][PheTyrIleLeu][PheTyrIle]Phe[ArgThr]Xaa[ThrAsn] (SEQ ID NO:84) [ValIle][PheTyr][PheTyrIleLeu][PheTyrIleLeu]PheArgXaa[ThrAsn] (SEQ ID NO:85) [ValIle][PheTyr][PheTyrLeu][PheTyrIleLeu][PheTyr][ArgThr][GluAspVal][ThrAsn] (SEQ ID NO:86)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle]CysXaaXaaAsp (SEQ ID NO:28) GlyLys[ValAlaIle]XaaXaaXaaArg[ValAlaIle]XaaXaaXaaCysLys (SEQ ID NO:29)

(i) [ArgLysAsn]Trp[ThrAla][ThrAlaSer][PheTyrLeu]Leu[LysArg] (SEQ ID NO:87) [PheTyr]Leu [LysArg][AlaSer]ArgLeu[AsnIle]Cys (SEQ ID NO:31) [AsnIle]CysSer[IleVal][ProSer]Gly (SEQ ID NO:32) Trp[ThrAla][ThrAlaSer][PheTyrLeu]LeuLys[AlaSerValIleLeu]XaaLeu (SEQ ID NO:88) Trp[ThrAlaSer][ThrAlaSer][PheTyrLeu]LeuLys[AlaSerIleLeu]XaaLeu (SEQ ID NO:89) Trp[ThrAla][ThrAlaSer]XaaLeuLysXaaXaaLeuXaaCys (SEQ ID NO:90)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIle]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle]ProXaaProArgProGlyXaaCys (SEQ ID NO:91) Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

5. An isolated semaphorin protein according to claim 1, wherein said peptide sequence is selected from the group consisting of:

(f) TyrPhePhe[PheTyr]ArgGlu (SEQ ID NO:18) Asp[LysTyr]Val[PheTyr][PheTyrLeu][PheTyrIleLeu][PheTyr] (SEQ ID NO:92) Asp[LysTyr]Val[PheTyr][PheTyrIleLeu][PheTyrIle][PheTyr] (SEQ ID NO:93) [ValIle]Tyr[PheTyrLeu][PheTyrIleLeu]Phe[ArgThr]Xaa[ThrAsn] (SEQ ID NO:94) [ValIle]Tyr[PheTyrIleLeu][PheTyrIle]Phe[ArgThr]Xaa[ThrAsn] (SEQ ID NO:95) [ValIle]Tyr[pheTyrIleLeu][PheTyrIleLeu]PheArgXaa[ThrAsn] (SEQ ID NO:96) Val[pheTyr][PheTyrLeu][PheTyrIleLeu][PheTyr][ArgThr][GtuAspVal][ThrAsn] (SEQ ID NO:97) Val[PheTyr][PheTyrIleLeu][PheTyrIle][PheTyr][ArgThr][GluAspVal][ThrAsn] (SEQ ID NO:98) Val[PheTyr][PheTyrIleLeu][PheTyrIleLeu][PheTyr]Arg[GluAspVal][ThrAsn] (SEQ ID NO:99)

(n) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

6. An isolated semaphorin protein according to claim 1, wherein said peptide sequence is selected from the group consisting of:

(b) CysGlyThr[AsnGly][AlaSerAsn][TyrPheHisGly][LysArgHisAsnGln] (SEQ ID NO:03) CysGlyThr[AsnGly][AlaSerAsn]XaaXaaPro (SEQ ID NO:04) CysGlyThr[AsnGly]XaaXaaXaaProXaa[CysAsp] (SEQ ID NO:05) CysGlyThrXaaXaaXaaXaaProXaa[CysAsp]XaaXaa[TyrIle] (SEQ ID NO:06)

(f) Asp[LysPheTyr]Val[PheTyr][PheTyrIleLeu][PheTyrIleLeu][PheTyr] (SEQ ID NO:22) [ValIle][PheTyr][PheTyrIleLeu][PheTyrIleLeu]Phe[ArgThr]Xaa[ThrAsn] (SEQ ID NO:23) Val[PheTyr][PheTyrIleLeu][PheTyrIleLeu][PheTyr][ArgThr][GluAspVal][ThrAsn] (SEQ ID NO:100)

(i) [ArgLysAsn]Trp[ThrAlaSer][ThrAlaSer][PheTyrLeu]Leu[LysArg] (SEQ ID NO:30) Trp[ThrAlaSer][ThrAlaSer][PheTyrLeu]LeuLys[AlaSerValIleLeu]XaaLeu (SEQ ID NO:33) Trp[ThrAlaSer][ThrAlaSer]XaaLeuLysXaaXaaLeuXaaCys (SEQ ID NO:34) TrpXaa[ThrSer]XaaLeuLysXaaXaaLeuXaaCys (SEQ ID NO:35)

(k) SerAla[ValIleLeu]CysXaa[PheTyr]XaaMet (SEQ ID NO:39), and (m) [ValLeuIle]ProXaaPro[ArgAla]ProGlyXaaCys (SEQ ID NO:42).

7. An isolated semaphorin protein comprising the amino acid sequence of SEQ ID NO:54, 58, 60, 62, or 64; or a portion of said amino acid sequence, said portion sufficient to provide a semaphorin binding specificity and comprising a peptide sequence selected from the group consisting of SEQ ID NOS: 1–52 and 67–100, and with the proviso that said peptide sequence is contained within neither SEQ ID NO:56 nor 66.

8. An isolated semaphorin protein according to claim 7, wherein said peptide sequence is selected from the group consisting of:

(a) [AspGlu]Cys[GlnLysArgAlaAsn]Asn[TyrPheVal]Ile (SEQ ID NO:1) Cys[GlnLysArgAlaAsn]Asn[TyrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3) CysGlyThr[AsnGly][AlaSerAsn]XaaXaaPro (SEQ ID NO:4) CysGlyThr[AsnGly]XaaXaaXaaProXaa[CysAsp] (SEQ ID NO:5) CysGlyThrXaaXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7) [CysSer]Pro[PheTyr][AspAsn]Pro[AspGluArgLys][HisLeuAsp] (SEQ ID NO:8) GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10) Leu [PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]ArgGlu (SEQ ID NO:18) [PheTyr]PhePhe[PheTyr]ArgGlu (SEQ ID NO:19) [PheTyr][PheTyr][PheTyr]ArgGlu[ThrAsn]Ala (SEQ ID NO:20) [IleVal][PheTyr]Phe[PheTyr][PheTyr]ArgGlu (SEQ ID NO:21) Asp[LysPheTyr]Val[PheTyr][PheTyrIleLeu][PheTyrIleLeu][PheTyr] (SEQ ID NO:22) [ValIle][PheTyr][PheTyrIleLeu][PheTyrIleLeu]Phe[ArgThr]Xaa[ThrAsn] (SEQ ID NO:23) [ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle]CysXaaXaaAsp (SEQ ID NO:28) GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30) [PheTyr]Leu[LysArg][AlaSer]ArgLeu[AsnIle]Cys (SEQ ID NO:31) [AsnIle]CysSer[IleVal][ProSer]Gly (SEQ ID NO:32) Trp[ThrAlaSer][ThrAlaSer][PheTyrLeu]LeuLys[AlaSerValIleLeu]XaaLeu (SEQ ID NO:33) Trp[ThrAlaSer][ThrAlaSer]XaaLeuLysXaaXaaLeuXaaCys (SEQ ID NO:34) TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle]ProXaaPro[ArgAla]ProGlyXaaCys (SEQ ID NO:42) Pro[GluAspTyrSerPhe]ProArgProGly[ThrGlnSer]Cys (SEQ ID NO:43)

(n) AspPro[HisPheTry]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

9. An isolated semaphorin protein according to claim 7, wherein said peptide sequence is selected from the group consisting of:

(a) AspCysGlnAsnTyrIle (SEQ ID NO:67)

(b) CysGlyThr[AsnGly][AlaSer]XaaXaaPro (SEQ ID NO:68)

(c) GlyXaa[SerCys]ProTyrAspPro (SEQ ID NO:69)

(d) LeuTyrSerGlyThr[ValAsnAla]Ala (SEQ ID NO:70)

(e) LeuAsnAlaProAsnPheVal (SEQ ID NO:71)

(f) [PheTyr]PhePhe[PheTyr]ArgGlu (SEQ ID NO:19)

(g) Glu[PheTyr]IleAsn[CysSer]GlyLys (SEQ ID NO:25)

(h) Arg[ValIle]AlaArgValCysLys (SEQ ID NO:72)

(i) Trp[ThrAla][ThrSer][PheTyr]LeuLys[AlaSer]ArgLeu (SEQ ID NO:73)

(j) ProPheTyrPhe[AsnAsp]GluIleGlnSer (SEQ ID NO:74)

(k) GlySerAlaValCysXaa[PheTyr] (SEQ ID NO:75)

(l) AsnSerAsnTrpLeu[ProAla]Val (SEQ ID NO:76)

(m) Pro[GluAsp]ProArgProGly[ThrGlnSer]Cys (SEQ ID NO:77), and (n) AspProTyrCys[AlaGly]TrpAsp (SEQ ID NO:78).

10. An isolated semaphorin protein according to claim 7, wherein said peptide sequence is selected from the group consisting of:

(a) [AspGlu]Cys[GlnLysArgAlaAsn]Asn[TyrPheVal]Ile (SEQ ID NO:01) Cys[GlnLysArgAlaAsn]Asn[TyrPheVal]Ile[ArgLysGlnThr] (SEQ ID NO:02)

(b) CysGlyThr[AsnGly][AlaSer][TyrPheHisGly][LysArgHisAsnGln] (SEQ ID NO:79) CysGlyThr[AsnGly][AlaSerAsn][TyrPheHis][LysArgHisAsnGln] (SEQ ID NO:80) CysGlyThr[AsnGly][AlaSer]XaaXaaPro (SEQ ID NO:81)

(c) [ArgIleGlnVal][GlyAla][LeuValLys][CysSer]Pro[PheTyr][AspAsn] (SEQ ID NO:07) [CysSer]Pro[PheTyr][AspAsn]Pro[AspGluArgLys][HisLeuAsp] (SEQ ID NO:08) GlyXaa[GlyAla]Xaa[CysSer]ProTyr[AspAsn]Pro (SEQ ID NO:09)

(d) Leu[PheTyr]Ser[GlyAla]Thr[ValAsnAla]Ala (SEQ ID NO:10) Leu[PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]ArgGlu (SEQ ID NO:18) [PheTyr]PhePhe[PheTyr]ArgGlu (SEQ ID NO:19) [PheTyr][PheTyr][PheTyr]ArgGlu[ThrAsn]Ala (SEQ ID NO:20) [IleVal][PheTyr]Phe[PheTyr][PheTyr]ArgGlu (SEQ ID NO:21) Asp[LysPheTyr]Val[PheTyr][PheTyrLeu][PheTyrIleLeu][PheTyr] (SEQ ID NO:22) Asp[LysPheTyr]Val[PheTyrIleLeu][PheTyrIle][PheTyr] (SEQ ID NO:82) [ValIle][PheTyr][PheTyrLeu][PheTyrIleLeu]Phe[ArgThr]Xaa[ThrAsn] (SEQ ID NO:83) [ValIle][PheTyr][PheTyrIleLeu][PheTyrIle]Phe[ArgThr]Xaa[ThrAsn] (SEQ ID NO:84) [ValIle][PheTyr][PheTyrIleLeu][PheTyrIleLeu]PheArgXaa[ThrAsn] (SEQ ID NO:85) [ValIle][PheTyr][PheTyrLeu][PheTyrIleLeu][PheTyr][ArgThr][GluAspVal][ThrAsh] (SEQ ID NO:86)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle]CysXaaXaaAsp (SEQ ID NO:28) GlyLys[ValAlaIle]XaaXaaXaaArg[ValAlaIle]XaaXaaXaaCysLys (SEQ ID NO:29)

(i) [ArgLysAsn]Trp[ThrAla][ThrAlaSer][PheTyrLeu]Leu[LysArg] (SEQ ID NO:87) [PheTyr]Leu[LysArg][AlaSer]ArgLeu[AsnIle]Cys (SEQ ID NO:31) [AsnIle]CysSer[IleVal][ProSer]Gly (SEQ ID NO:32) Trp[ThrAla][ThrAlaSer][PheTyrLeu]LeuLys[AlaSerValIleLeu]XaaLeu (SEQ ID NO:88) Trp[ThrAlaSer][ThrAlaSer][PheTyrLeu]LeuLys[AlaSerIleLeu]XaaLeu (SEQ ID NO:89) Trp[ThrAla][ThrAlaSer]XaaLeuLysXaaXaaLeuXaaCys (SEQ ID NO:90)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIle]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle]ProXaaProArgProGlyXaaCys (SEQ ID NO:91) Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

11. An isolated semaphorin protein according to claim 7, wherein said peptide sequence is selected from the group consisting of:

(f) TyrPhePhe[PheTyr]ArgGlu (SEQ ID NO:18) Asp[LysTyr]Val[PheTyr][PheTyrLeu][PheTyrIleLeu][PheTyr](SEQ ID NO:92) Asp[LysTyr]Val[PheTyr][PheTyrIleLeu][PheTyrIle][PheTyr] (SEQ ID NO:93) [ValIle]Tyr[PheTyrLeu][PheTyrIleLeu]Phe[ArgThr]Xaa[ThrAsn] (SEQ ID NO:94) [ValIle]Tyr[PheTyrIleLeu][PheTyrIle]Phe[ArgThr]Xaa[ThrAsn] (SEQ ID NO:95) [ValIle]Tyr[PheTyrIleLeu][PheTyrIleLeu]PheArgXaa[ThrAsn] (SEQ ID NO:96) Val[PheTyr][PheTyrLeu][PheTyrIleLeu][PheTyr][ArgThr][GluAspVal][ThrAsn] (SEQ ID NO:97) Val[PheTyr][PheTyrIleLeu][PheTyrIle][PheTyr][ArgThr][GhAspVal][ThrAsn] (SEQ ID NO:98) Val[PheTyr][PheTyrIleLeu][PheTyrIleLeu][PheTyr]Arg[GluAspVal][ThrAsh] (SEQ ID NO:99)

(n) CysXaaXaaXaaAspProXaaCysXaaTrpAsp (SEQ ID NO:48) CysXaaXaaAspProXaaCysXaaTrpAsp (SEQ

ID NO:49) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

12. An isolated semaphorin protein comprising the amino acid sequence of SEQ ID NO:54, 58, 60, 62, or 64; or a portion of said amino acid sequence, said portion sufficient to provide a semaphorin binding specificity and comprising a peptide sequence selected from the group consisting of SEQ ID NOS: 1–52 and 67–100, and with the proviso that said peptide sequence is other than a sequence occurring in a natural vaccinia or variola major virus open reading frame translation product.

13. An isolated semaphorin protein according to claim 12, wherein said peptide sequence is selected from the group consisting of:

(a) [AspGlu]Cys[GlnLysArgAlaAsn]Asn[TyrPheVal]Ile (SEQ ID NO:1) Cys[GlnLysArgAlaAsn]Asn[TyrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3) CysGlyThr[AsnGly][AlaSerAsn]XaaXaaPro (SEQ ID NO:4) CysGlyThr[AsnGly]XaaXaaXaaProXaa[CysAsp] (SEQ ID NO:5) CysGlyThrXaaXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7) [CysSer]Pro[PheTyr][AspAsn]Pro[AspGluArgLys][HisLeuAsp] (SEQ ID NO:8) GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10) Leu[PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]ArgGlu (SEQ ID NO:18) [PheTyr]PhePhe[PheTyr]ArgGlu (SEQ ID NO:19) [PheTyr][PheTyr][PheTyr]ArgGlu[ThrAsn]Ala (SEQ ID NO:20) [IleVal][PheTyr]Phe[PheTyr][PheTyr]ArgGlu (SEQ ID NO:21) Asp[LysPheTyr]Val[PheTyr][PheTyrIleLeu][PheTyrIleLeu][PheTyr] (SEQ ID NO:22) [ValIle][PheTyr][PheTyrIleLeu][PheTyrIleLeu]Phe[ArgThr]Xaa[ThrAsn] (SEQ ID NO:23) [ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle]CysXaaXaaAsp (SEQ ID NO:28) GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30) [PheTyr]Leu[LysArg][AlaSer]ArgLeu[AsnIle]Cys (SEQ ID NO:31) [AsnIle]CysSer[IleVal][ProSer]Gly (SEQ ID NO:32) Trp[ThrAlaSer][ThrAlaSer][PheTyrLeu]LeuLys[AlaSerValIleLeu]XaaLeu (SEQ ID NO:33) Trp[ThrAlaSer][ThrAlaSer]XaaLeuLysXaaXaaLeuXaaCys (SEQ ID NO:34) TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41) [ValLeuIle]ProXaaPro[ArgAla]ProGlyXaaCys (SEQ ID NO:42) Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaXaaAspXaaXaaCysXaaTrpAsp (SEQ ID NO:50) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

14. An isolated semaphorin protein according to claim 12, wherein said peptide sequence is selected from the group consisting of:

(a) AspCysGlnAsnTyrIle (SEQ ID NO:67)

(b) CysGlyThr[AsnGly][AlaSer]XaaXaaPro (SEQ ID NO:68)

(c) GlyXaa[SerCys]ProTyrAspPro (SEQ ID NO:69)

(d) LeuTyrSerGlyThr[ValAsnAla]Ala (SEQ ID NO:70)

(e) LeuAsnAlaProAsnPheVal (SEQ ID NO:71)

(f) [PheTyr]PhePhe[PheTyr]ArgGlu (SEQ ID NO:19)

(g) Glu[PheTyr]IleAsn[CysSer]GlyLys (SEQ ID NO:25)

(h) Arg[ValIle]AlaArgValCysLys (SEQ ID NO:72)

(i) Trp[ThrAla][ThrSer][PheTyr]LeuLys[AlaSer]ArgLeu (SEQ ID NO:73)

(j) ProPheTyrPhe[AsnAsp]GluIleGlnSer (SEQ ID NO:74)

(k) GlySerAlaValCysXaa[PheTyr] (SEQ ID NO:75)

(l) AsnSerAsnTrpLeu[ProAla]Val (SEQ ID NO:76)

(m) Pro[GluAsp]ProArgProGly[ThrGlnSer]Cys (SEQ ID NO:77), and (n) AspProTyrCys[AlaGly]TrpAsp (SEQ ID NO:78).

15. An isolated semaphorin protein according to claim 12, wherein said peptide sequence is selected from the group consisting of:

(a) [AspGlu]Cys[GlnLysArgAlaAsn]Asn[TyrPheVal]Ile (SEQ ID NO:01) Cys[GlnLysArgAlaAsn]Asn[TyrPheVal]Ile[ArgLysGlnThr] (SEQ ID NO:02)

(b) CysGlyThr[AsnGly][AlaSer][TyrPheHisGly][LysArgHisAsnGln] (SEQ ID NO:79) CysGlyThr[AsnGly][AlaSerAsn][TyrPheHis][LysArgHisAsnGln] (SEQ ID NO:80) CysGlyThr[AsnGly][AlaSer]XaaXaaPro (SEQ ID NO:81)

(c)[ArgIleGlnVal][GlyAla][LeuValLys][CysSer]Pro[PheTyr][AspAsn] (SEQ ID NO:07) [CysSer]Pro[PheTyr][AspAsn]Pro[AspGluArgLys][HisLeuAsp] (SEQ ID NO:08) GlyXaa[GlyAla]Xaa[CysSer]ProTyr[AspAsn]Pro (SEQ ID NO:09)

(d) Leu[PheTyr]Ser[GlyAla]Thr[ValAsnAla]Ala (SEQ ID NO:10) Leu[PheTyr]SerXaaThrXaaAla[AspGlu][PheTyr] (SEQ ID NO:11) [PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14) PhePhe[PheTyr]ArgGlu[ThrAsn] (SEQ ID NO:15) PhePheArgGlu[ThrAsn]Ala (SEQ ID NO:16) Phe[PheTyr]ArgGlu[ThrAsn]Ala (SEQ ID NO:17) TyrPhePhe[PheTyr]ArgGlu (SEQ ID NO:18) [PheTyr]PhePhe[PheTyr]ArgGlu (SEQ ID NO:19) [PheTyr][PheTyr][PheTyr]ArgGlu[ThrAsn]Ala (SEQ ID NO:20) [IleVal][PheTyr]Phe[PheTyr][PheTyr]ArgGlu (SEQ ID NO:21) Asp[LysPheTyr]Val[PheTyr][PheTyrLeu][PheTyrIleLeu][PheTyr] (SEQ ID NO:22) Asp[LysPheTyr]Val[PheTyr][PheTyrIleLeu][PheTyrIle][PheTyr] (SEQ ID NO:82) [ValIle][PheTyr][PheTyrLeu][PheTyrIleLeu]Phe[ArgThr]Xaa[ThrAsn] (SEQ ID NO:83) [ValIle][PheTyr][PheTyrIleLeu][PheTyrIle]Phe[ArgThr]Xaa[ThrAsn] (SEQ ID NO:84) [ValIle][PheTyr][PheTyrIleLeu][PheTyrIleLeu]PheArgXaa[ThrAsn] (SEQ ID NO:85) [ValIle][PheTyr][PheTyrLeu][PheTyrIleLeu][PheTyr][ArgThr][GluAspVal][ThrAsn] (SEQ ID NO:86)

(g) Glu[PheTyr]IleAsn[CysSer]GlyLys (SEQ ID NO:25) [PheTyr]IleAsnCysGlyLys[AlaValIle] (SEQ ID NO:26)

(h) Arg[ValIle][AlaGly][ArgGln][ValIle]CysLys (SEQ ID NO:27) Arg[ValIle]Xaa[ArgGln][ValIle]CysXaaXaaAsp (SEQ ID NO:28) GlyLys[ValAlaIle]XaaXaaXaaArg[ValAlaIle]XaaXaaXaaCysLys (SEQ ID NO:29)

(i) [ArgLysAsn]Trp[ThrAla][ThrAlaSer][PheTyrLeu]Leu[LysArg] (SEQ ID NO:87) [PheTyr]Leu[LysArg][AlaSer]ArgLeu[AsnIle]Cys (SEQ ID NO:31) [AsnIle]CysSer[IleVal][ProSer]Gly (SEQ ID NO:32) Trp[ThrAla][ThrAlaSer][PheTyrLeu]LeuLys[AlaSerValIleLeu]XaaLeu (SEQ ID NO:88) Trp[ThrAlaSer][ThrAlaSer][PheTyrLeu]LeuLys[AlaSerIleLeu]XaaLeu (SEQ ID NO:89) Trp[ThrAla][ThrAlaSer]XaaLeuLysXaaXaaLeuXaaCys (SEQ ID NO:90)

(j) [PheTyr][PheTyr][AsnAsp]GluIleGlnSer (SEQ ID NO:36) [PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38) SerAla[ValIle]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)
[ValLeuIle]ProXaaProArgProGlyXaaCys (SEQ ID NO:91)
Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44) Pro[HisPheTyr]Cys[AlaGly]TrpAsp (SEQ ID NO:45) AspProXaaCys[AlaGly]TrpAsp (SEQ ID NO:46) CysXaaXaaXaaXaaAspProXaaCysXaaTrpAsp (SEQ ID NO:47) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaAspXaaXaaCysXaaTrpAsp (SEQ ID NO:50) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

16. An isolated semaphorin protein according to claim 12, wherein said peptide sequence is selected from the group consisting of:

(f) TyrPhePhe[PheTyr]ArgGlu (SEQ ID NO:18) Asp[LysTyr]Val[PheTyr][PheTyrLeu][PheTyrIleLeu][PheTyr] (SEQ ID NO:92) Asp[LysTyr]Val[PheTyr][PheTyrIleLeu][PheTyrIle][PheTyr] (SEQ ID NO:93) [ValIle]Tyr[PheTyrLeu][PheTyrIleLeu]Phe[ArgThr]Xaa[ThrAsn] (SEQ ID NO:94) [ValIle]Tyr[PheTyrIle][PheTyrIle]Phe[ArgThr]Xaa[ThrAsn] (SEQ ID NO:95) [ValIle]Tyr[PheTyrIleLeu][PheTyrIleLeu]PheArgXaa[ThrAsn] (SEQ ID NO:96) Val[PheTyr][PheTyrLeu][PheTyrIleLeu][PheTyr][ArgThr][GluAspVal][ThrAsn] (SEQ ID NO:97) Val[PheTyr][PheTyrIleLeu][PheTyrIle][PheTyr][ArgThr][GluAspVal][ThrAsn] (SEQ ID NO:98) Val[PheTyr][PheTyrIleLeu][PheTyrIleLeu][PheTyr]Arg[GluAspVal][ThrAsn] (SEQ ID NO:99)

(n) CysXaaXaaXaaAspProXaaCysXaaTrpAsp (SEQ ID NO:48) CysXaaXaaAspProXaaCysXaaTrpAsp (SEQ ID NO:49) CysXaaXaaCysXaaXaaXaaAspXaaXaaCysXaaTrpAsp (SEQ ID NO:51), and CysXaaXaaCysXaaXaaAspXaaXaaCysXaaTrpAsp (SEQ ID NO:52).

17. An isolated semaphorin protein according to claim 1, wherein said protein comprises an amino acid sequence selected from SEQ ID NO:54, 56, 58, 60, 62 and 64.

18. An isolated semaphorin protein according to claim 12, wherein said protein comprises SEQ ID NO:54.

19. An isolated semaphorin protein according to claim 17, wherein said protein comprises SEQ ID NO:56.

20. An isolated semaphorin protein according to claim 12, wherein said protein comprises SEQ ID NO:58.

21. An isolated semaphorin protein according to claim 12, wherein said protein comprises SEQ ID NO:60.

22. An isolated semaphorin protein according to claim 12, wherein said protein comprises SEQ ID NO:62.

23. An isolated semaphorin protein according to claim 12, wherein said protein comprises SEQ ID NO:64.

\* \* \* \* \*